US009394544B2

(12) United States Patent
Kim

(10) Patent No.: US 9,394,544 B2
(45) Date of Patent: Jul. 19, 2016

(54) AMELIORATING OXIDATIVE STRESS IN NEURODEGENERATIVE DISEASE VIA NOX1 TARGETING

(71) Applicant: Yoon-Seong Kim, Orlando, FL (US)

(72) Inventor: Yoon-Seong Kim, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 14/164,003

(22) Filed: Jan. 24, 2014

(65) Prior Publication Data
US 2014/0221457 A1    Aug. 7, 2014

Related U.S. Application Data

(60) Provisional application No. 61/756,416, filed on Jan. 24, 2013.

(51) Int. Cl.
| | | |
|---|---|---|
| *A61K 31/70* | (2006.01) | |
| *C07H 21/02* | (2006.01) | |
| *C07H 21/04* | (2006.01) | |
| *C12N 15/113* | (2010.01) | |
| *A61K 45/06* | (2006.01) | |
| *A61K 31/713* | (2006.01) | |
| *C12Q 1/68* | (2006.01) | |

(52) U.S. Cl.
CPC .......... *C12N 15/1137* (2013.01); *A61K 31/713* (2013.01); *A61K 45/06* (2013.01); *C12Y 106/03* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | | | |
|---|---|---|---|---|
| 2013/0225612 | A1* | 8/2013 | Lambeth | A01N 1/0226 514/266.2 |
| 2014/0357549 | A1* | 12/2014 | Ranayhossaini | C07K 16/2803 514/1.9 |

OTHER PUBLICATIONS

Alam ZI, et al, "A generalised increase in protein carbonyls in the brain in Parkinson's but not incidental Lewy body disease." J Neurochem. 1997; vol. 69: pp. 1326-1329.
Alvarez B, et al, "Kinetics of peroxynitrite reaction with amino acids and human serum albumin." The Journal of biological chemistry. 1999; vol. 274: pp. 842-848.
Beyer K, et al, "Molecular pathology of lewy body diseases." Int J Mol Sci. 2009; vol. 10: pp. 724-745.
Brown TP,et al, "Pesticides and Parkinson's disease—is there a link?" Environ Health Perspect. 2006; vol. 114: pp. 156-164.
Butterfield DA, et al, "Brain protein oxidation in age-related neurodegenerative disorders that are associated with aggregated proteins." Mech Ageing Dev.2001; vol. 122: pp. 945-962.
Chartier-Harlin MC, et al, "Alpha-synuclein locus duplication as a cause of familial Parkinson's disease." Lancet. 2004; vol. 364: pp. 1167-1169.
Choi DH, et al, "NADPH Oxidase 1-Mediated Oxidative Stress Leads to Dopamine Neuron Death in Parkinson's Disease." Antioxidants & redox signaling. vol. 2012.
Choi DH, et al, "Role of matrix metalloproteinase 3-mediated alpha-synuclein cleavage in dopaminergic cell death." The Journal of biological chemistry. 2011; vol. 286: pp. 14168-14177.
Clough RL,et al, "Regulation of alpha-synuclein expression in cultured cortical neurons." J Neurochem. 2011; vol. 117: pp. 275-285.
Clough RL, et al, "Functional dissection of the alpha-synuclein promoter: transcriptional regulation by ZSCAN21 and ZNF219." J Neurochem.2009; vol. 110: pp. 1479-1490.
Clough RL, et al, "A novel pathway for transcriptional regulation of alpha-synuclein." FASEB J. 2007; vol. 21:pp. 596-607.
Cookson MR. "alpha-Synuclein and neuronal cell death." Mol Neurodegener.2009; vol. 4: pp. 9.
Cristovao AC, et al, "The role of NADPH oxidase 1-derived reactive oxygen species in paraquat-mediated dopaminergic cell death." Antioxidants & redox signaling. 2009;vol. 11: pp. 2105-2118.
Dexter DT, et al "Basal lipid peroxidation in substantia nigra is increased in Parkinson's disease." J Neurochem. 1989; vol. 52:pp. 381-389.
Dexter DT, et al, "Increased levels of lipid hydroperoxides in the parkinsonian substantia nigra: an HPLC and ESR study." Mov Disord. 1994; vol. 9:pp. 92-97.
Donato R,et al, "Differential development of neuronal physiological responsiveness in two human neural stem cell lines." BMC neuroscience. 2007;vol. 8: pp. 36.
Gatto NM, et al, "alpha-Synuclein gene may interact with environmental factors in increasing risk of Parkinson's disease." Neuroepidemiology. 2010; vol. 35:pp. 191-195.
Hardy J, et al, "The genetics of Parkinson's syndromes: a critical review." Curr Opin Genet Dev. 2009; vol. 19: pp. 254-265.
Harper SQ, et al, "RNA interference improves motor and neuropathological abnormalities in a Huntington's disease mouse model." Proc Natl Acad Sci U S A.2005; vol. 102: pp. 5820-5825.
Harraz MM, et al, "SOD1 mutations disrupt redox-sensitive Rac regulation of NADPH oxidase in a familial ALS model." J Clin Invest.2008; vol. 118: pp. 659-670.
Hashimoto M, et al, "Oxidative stress induces amyloid-like aggregate formation of NACP/alpha-synuclein in vitro."Neuroreport. 1999; vol. 10: pp. 717-721.
Javoy F, et al, "Specificity of dopaminergic neuronal degeneration induced by intracerebral injection of 6-hydroxydopamine in the nigrostriatal dopamine system." Brain Res. 1976; vol. 102: pp. 201-215.
Krishnan S, et al,"Oxidative dimer formation is the critical rate-limiting step for Parkinson's disease alpha-synuclein fibrillogenesis. " Biochemistry. 2003; vol. 42: pp. 829-837.

(Continued)

*Primary Examiner* — Sean McGarry
(74) *Attorney, Agent, or Firm* — Timothy H. Van Dyke; Beusse, Wolter, Sanks & Maire, PLLC

(57) ABSTRACT

Disclosed herein are methods, compounds and compositions designed for ameliorating oxidative stress in cells. In particular, disclosed are viral vectors that express RNA interfering molecules for inhibiting expression or activity of Nox1 or RAC1. Depending on the location of administration, expression of inhibiting molecules can reduce oxidative stress in neurons associated with a particular neurodegenerative condition.

11 Claims, 16 Drawing Sheets

(56) References Cited

OTHER PUBLICATIONS

Kruger R, et al, "Ala30Pro mutation in the gene encoding alpha-synuclein in Parkinson's disease." Nat Genet. 1998; vol. 18: pp. 106-108.

Manning-Bog AB, et al, "The herbicide paraquat causes up-regulation and aggregation of alpha-synuclein in mice: paraquat and alpha-synuclein." The Journal of biological chemistry. 2002; vol. 277: pp. 1641-1644.

Matsuzaki M, et al, "Histochemical features of stress-induced aggregates in alpha-synuclein overexpressing cells." Brain Res. 2004; vol. 1004: pp. 83-90.

McCormack AL, et al, "Role of oxidative stress in paraquat-induced dopaminergic cell degeneration." J Neurochem.2005; vol. 93: pp. 1030-1037.

Miller RL, Jet al, "Oxidative and inflammatory pathways in Parkinson's disease." Neurochem Res. 2009; vol. 34: pp. 55-65.

Neumann M, et al, "Misfolded proteinase K-resistant hyperphosphorylated alpha-synuclein in aged transgenic mice with locomotor deterioration and in human alpha-synucleinopathies." J Clin Invest. 2002; vol. 110: pp. 1429-1439.

Nuber S, et al, "Neurodegeneration and motor dysfunction in a conditional model of Parkinson's disease." J Neurosci. 2008; vol. 28: pp. 2471-2484.

Polymeropoulos MH, et al, "Mutation in the alpha-synuclein gene identified in families with Parkinson's disease." Science. 1997; vol. 276: pp. 2045-2047.

Singleton AB, et al, "alpha-Synuclein locus triplication causes Parkinson's disease." Science. 2003; vol. 302: pp. 841.

Sofic E, et al, "Reduced and oxidized glutathione in the substantia nigra of patients with Parkinson's disease." Neurosci Lett. 1992; vol. 142: pp. 128-130.

Sorce S, et al, "NOX enzymes in the central nervous system: from signaling to disease." Antioxidants & redox signaling. 2009; vol. 11: pp. 2481-2504.

Souza JM, et al, "Dityrosine cross-linking promotes formation of stable alpha-synuclein polymers. Implication of nitrative and oxidative stress in the pathogenesis of neurodegenerative synucleinopathies." The Journal of biological chemistry. 2000; vol. 275: pp. 18344-18349.

Terzioglu M, et al, "Parkinson's disease: genetic versus toxin-induced rodent models." FEBS J. 2008; vol. 275: pp. 1384-1391.

Turk PW, et al, "DNA adduct 8-hydroxyl-2'-deoxyguanosine (8-hydroxyguanine) affects function of human DNA methyltransferase." Carcinogenesis. 1995; vol. 16: pp. 1253-1255.

Uversky VN,et al, "Pesticides directly accelerate the rate of alpha-synuclein fibril formation: a possible factor in Parkinson's disease." FEBS Lett. 2001; vol. 500: pp. 105-108.

Vekrellis K, et al, "Pathological roles of alpha-synuclein in neurological disorders." Lancet Neurol. 2011; vol. 10: pp. 1015-1025.

Winner B, et al, "In vivo demonstration that alpha-synuclein oligomers are toxic." Proc Natl Acad Sci U S A. 2011; vol. 108: pp. 4194-4199.

Wood-Kaczmar A, et al, "PINK1 is necessary for long term survival and mitochondrial function in human dopaminergic neurons." PLoS one. 2008; vol. 3: pp. e2455.

Zarranz JJ, et al, "The new mutation, E46K, of alpha-synuclein causes Parkinson and Lewy body dementia." Ann Neurol. 2004; vol. 55: pp. 164-173.

Zawia NH, et al, "Epigenetics, oxidative stress, and Alzheimer disease." Free Radic Biol Med. 2009; vol. 46: pp. 1241-1249.

Zhang J, et al, Montine TJ. "Parkinson's disease is associated with oxidative damage to cytoplasmic DNA and RNA in substantia nigra neurons." Am J Pathol. 1999; vol. 154: pp. 1423-1429.

Akbari M., et al "Different organization of base excision repair of uracil in DNA in nuclei and mitochondria and selective upregulation of mitochondrial uracil-DNA glycosylase after oxidative stress", Neuroscience, 2007; vol. 145: pp. 1201-1212.

Alam ZI.et al, "Oxidative DNA damage in the parkinsonian brain: An apparent selective increase in 8-hydroxyguanine levels in substantia nigra." J Neurochem. 1997; vol. 69: pp. 1196-1203.

Anantharam V. et al, "Pharmacological inhibition of neuronal NADPH oxidase protects against 1-methyl-4-phenylpyridinium (MPP+)-induced oxidative stress and apoptosis in mesencephalic dopaminergic neuronal cells." Neurotoxicology. 2007; vol. 28: pp. 988-997.

Banfi B. et al, "Two novel proteins activate superoxide generation by the NADPH oxidase NOX1." J Biol Chem. 2003; vol. 278: pp. 3510-3513.

Bedard K.et al, "The NOX Family of ROS-Generating NADPH Oxidases:" Physiology and pathophysiology. Physiol Rev. 2007; vol. 87: pp. 245-313.

Behrens MM. et al, "Ketamine-induced loss of phenotype of fast-spiking interneurons is mediated by NADPH-oxidase." Science. 2007; vol. 318: pp. 1645-1647.

Bender A. et al, "High levels of mitochondrial DNA deletions in substantia nigra neurons in aging and Parkinson disease." Nat Genet. 2006; vol. 38: pp. 515-517.

Bjorklund A. et al, "Towards a neuroprotective gene therapy for Parkinson's disease: Use of adenovirus, AAV and lentivirus vectors for gene transfer of GDNF to the nigrostriatal system in the rat Parkinson model." Brain Res. 2000; vol. 886:pp. 82-98.

Bokoch GM. et al, "Current molecular models for NADPH oxidase regulation by Rac GTPase." Blood. 2002; vol. 100: pp. 2692-2696.

Chamulitrat W. et al, "Association of gp91phox homolog Nox1 with anchorage-independent growth and MAP kinase-activation of transformed human keratinocytes." Oncogene.2003; vol. 22: pp. 6045-6053.

Cheng G. et al, "Homologs of gp91phox: cloning and tissue expression of Nox3, Nox4, and Nox5." Gene. 2001; vol. 269: pp. 131-140.

Daiber A. "Redox signaling (cross-talk) from and to mitochondria involves mitochondrial pores and reactive oxygen species." Biochim Biophys Acta. 2010;vol. 1797: pp. 897-906.

De Deken X. et al, "Cloning of two human thyroid cDNAs encoding new members of the NADPH oxidase family." J Biol Chem. 2000; vol. 275: pp. 23227-23233.

Desouki MM. et al, "Cross talk between mitochondria and superoxide generating NADPH oxidase in breast and ovarian tumors." Cancer Biol Ther. 2005; vol. 4: pp. 1367-1373.

Edens WA. et al, "Tyrosine cross-linking of extracellular matrix is catalyzed by Duox, a multidomain oxidase/peroxidase with homology to the phagocyte oxidase subunit gp91phox." J Cell Biol. 2001; vol. 154: pp. 879-891.

Fan CY. et al, "PKCdelta mediates up-regulation of NOX1, a catalytic subunit of NADPH oxidase, via transactivation of the EGF receptor: Possible involvement of PKCdelta in vascular hypertrophy." Biochem J. 2005; aol 390: pp. 761-767.

Geiszt M. et al, "NAD(P)H oxidase 1, a product of differentiated colon epithelial cells, can partially replace glycoprotein 91phox in the regulated production of superoxide by phagocytes." J Immunol. 2003; vol. 171: pp. 299-306.

Geiszt M. et al, "Proteins homologous to p47phox and p67phox support superoxide production by NAD(P)H oxidase 1 in colon epithelial cells." J Biol Chem.2003; vol. 278: pp. 20006-20012.

Glinka Y. et al, "Mechanism of 6-hydroxydopamine neurotoxicity. J Neural Transm Suppl." 1997;vol. 50: pp. 55-66.

Gordillo, G et al., "Nox-4-Dependent Nuclear H2O2 Drives DNA Oxidation Resulting in 8-OHdG as Urinary Biomarker and Hemangioendothelioma Formation", Antioxidants & Redox Signaling, 2010, vol. 12, pp. 933-943.

Hilenski LL. et al "Distinct subcellular localizations of Nox1 and Nox4 in vascular smooth muscle cells." Arterioscler Thromb Vasc Biol. 2004; vol. 24: pp. 677-683.

Infanger DW. et al, "NADPH oxidases of the brain: Distribution, regulation, and function. Antioxid Redox Signal." 2006; vol. 8: pp. 1583-1596.

Katsuyama M. et al, "Essential role of ATF-1 in induction of NOX1, a catalytic subunit of NADPH oxidase: Involvement of mitochondrial respiratory chain." Biochem J. 2005; vol. 386: pp. 255-261.

Kawahara T. et al,. "Helicobacter pylori lipopolysaccharide activates Rac1 and transcription of NADPH oxidase Nox1 and its organizer NOXO1 in guinea pig gastric mucosal cells." Am J Physiol Cell Physiol. 2005; vol. 288: pp. C450-C457.

(56) References Cited

OTHER PUBLICATIONS

Kuroda J. et al, "The superoxide-producing NAD(P)H oxidase Nox4 in the nucleus of human vascular endothelial cells." Genes Cells. 2005; vol. 10: pp. 1139-1151.

Lee SB. et al, "Link between mitochondria and NADPH oxidase 1 isozyme for the sustained production of reactive oxygen species and cell death." J Biol Chem. 2006; vol. 281: pp. 36228-36235.

Marden JJ. et al, "Redox modifier genes in amyotrophic lateral sclerosis in mice." J Clin Invest.2007; vol. 117: pp. 2913-2919.

Michaelson D. et al, "Rac1 accumulates in the nucleus during the G2 phase of the cell cycle and promotes cell division." J Cell Biol. 2008; vol. 181: pp. 485-496.

Migliore L. et al, "Oxidative damage and cytogenetic analysis in leukocytes of Parkinson's disease patients." Neurology. 2002; vol. 58: pp. 1809-1815.

Nikolova S. et al, "Rac1-NADPH oxidase-regulated generation of reactive oxygen species mediates glutamate-induced apoptosis in SH-SY5Y human neuroblastoma cells." Free Radic Res. 2005; vol. 39: pp. 1295-1304.

Nakebeppu, Y., et al., "Oxidative Damage in Nucleic Acids and Parkinson's Disease", Journal of Neuroscience Research, 2007, vol. 85, pp. 919-934.

Nouspikel T. "DNA repair in differentiated cells: Some new answers to old questions.Neuroscience." 2007; vol. 145: pp. 1213-1221.

Prasad KN. et al, "Establishment and characterization of immortalized clonal cell lines from fetal rat mesencephalic tissue." In Vitro Cell Dev Biol Anim. 1994; vol. 30A:pp. 596-603.

Qin B. et al, "A key role for the microglial NADPH oxidase in APP-dependent killing of neurons." Neurobiol Aging.2006; vol. 27: pp. 1577-1587.

Rodriguez-Lebron E. et al, "Intrastriatal rAAV-mediated delivery of anti-huntingtin shRNAs induces partial reversal of disease progression in R6/1 Huntington's disease transgenic mice." Mol Ther. 2005; vol. 12: pp. 618-633.

Rodriguez-Pallares J.et al, "Mechanism of 6-hydroxydopamine neurotoxicity: The role of NADPH oxidase and microglial activation in 6-hydroxydopamine-induced degeneration of dopaminergic neurons." J Neurochem. 2007; vol. 103: pp. 145-156.

Rossi F. et al, "Biochemical aspects of phagocytosis in polymorphonuclear leucocytes. NADH and NADPH oxidation by the granules of resting and phagocytizing cells.Experientia." 1964; vol. 20:pp. 21-23.

Schapira AH. et al, "Mitochondrial complex I deficiency in Parkinson's disease." Lancet. 1989; vol. 1:pp. 1269.

Sherer TB. et al, "Oxidative damage in Parkinson's disease." Antioxid Redox Signal. 2005;vol. 7:pp. 627-629.

Silva RM. et al, "Mixed lineage kinase-c-jun N-terminal kinase signaling pathway: A new therapeutic target in Parkinson's disease." Mov Disord.2005; vol. 20:pp. 653-664.

Stolk, J et al., "Characteristics of the Inhibition of NAPDH Oxidase Activation in Neutrophils by Apocynin, a Methoxy-substituted Catechol", American Journal of Respiratory Cell and Molecular Biology, Jul. 1994, vol. 11, pp. 95-102.

West, Mark J et al., "Unbiased Stereological Estimation of the Number of Neurons in the Human Hippocampus", The Journal of Comparative Neurology, 1990, vol. 296, pp. I-22.

Suh YA. et al, "Cell transformation by the superoxide-generating oxidase Mox1." Nature.1999; vol. 401: pp. 79-82.

Ueyama T. et al, "Subcellular localization and function of alternatively spliced Noxo1 isoforms." Free Radic Biol Med. 2007; vol. 42: pp. 180-190.

Van der Perren A. et al, "Efficient and stable transduction of dopaminergic neurons in rat substantia nigra by rAAV 2/1, 2/2, 2/5, 2/6.2, 2/7, 2/8 and 2/9." Gene Ther. 2011; vol. 18: pp. 517-527.

Wosniak JJ. et al, "Cross-talk between mitochondria and NADPH oxidase: Effects of mild mitochondrial dysfunction on angiotensin II mediated increase in Nox isoform expression and activity in vascular smooth muscle cells." Antioxid Redox Signal. 2009; vol. 11: pp. 1265-1278.

Wu DC. et al, "NADPH oxidase mediates oxidative stress in the 1-methyl-4-phenyl-1,2,3,6-tetrahydropyridine model of Parkinson's disease." Proc Natl Acad Sci USA. 2003; vol. 100:pp. 6145-6150.

Zekry D. et al, "A role for NOX NADPH oxidases in Alzheimer's disease and other types of dementia?" IUBMB Life. 2003; vol. 55: pp. 307-313.

\* cited by examiner

SEQUENCE LISTING

```
<160> NUMBER OF SEQ ID NOS: 43

<210> SEQ ID NO 1
<211> LENGTH: 21
<212> TYPE: DNA
<213> ORGANISM: Rattus norvegicus

<400> SEQUENCE: 1
tgacagtgat gtatgcagca t                                              21

<210> SEQ ID NO 2
<211> LENGTH: 21
<212> TYPE: DNA
<213> ORGANISM: Rattus norvegicus

<400> SEQUENCE: 2
cagcttgttg tgtgcacgct g                                              21

<210> SEQ ID NO 3
<211> LENGTH: 22
<212> TYPE: DNA
<213> ORGANISM: Rattus norvegicus

<400> SEQUENCE: 3
actcgaaaac ttcttgggtc ag                                             22

<210> SEQ ID NO 4
<211> LENGTH: 23
<212> TYPE: DNA
<213> ORGANISM: Rattus norvegicus

<400> SEQUENCE: 4
tcctgtgatg ccagccaacc gag                                            23

<210> SEQ ID NO 5
<211> LENGTH: 20
<212> TYPE: DNA
<213> ORGANISM: Rattus norvegicus

<400> SEQUENCE: 5
gccggcggta tggcgctgtc                                                20

<210> SEQ ID NO 6
<211> LENGTH: 23
<212> TYPE: DNA
```

```
<213> ORGANISM: Rattus norvegicus

<400> SEQUENCE: 6
ccaccatgca gacacctgtc agg                                              23

<210> SEQ ID NO 7
<211> LENGTH: 22
<212> TYPE: DNA
<213> ORGANISM: Rattus norvegicus

<400> SEQUENCE: 7 tctagggat cagatacggg ac                                                22

<210> SEQ ID NO 8
<211> LENGTH: 23
<212> TYPE: DNA
<213> ORGANISM: Rattus norvegicus

<400> SEQUENCE: 8
ccaaggaaat ccatgggctc cag                                              23

<210> SEQ ID NO 9
<211> LENGTH: 21
<212> TYPE: DNA
<213> ORGANISM: Rattus norvegicus

<400> SEQUENCE: 9
acccagtatc agcccatgct g                                                21

<210> SEQ ID NO 10
<211> LENGTH: 21
<212> TYPE: DNA
<213> ORGANISM: Rattus norvegicus

<400> SEQUENCE: 10
atggagcatc aggaagcttg g                                                21

<210> SEQ ID NO 11
<211> LENGTH: 23
<212> TYPE: DNA
<213> ORGANISM: Rattus norvegicus

<400> SEQUENCE: 11
gttaaaggag atgttcccca ttg                                              23

<210> SEQ ID NO 12
<211> LENGTH: 23
<212> TYPE: DNA
<213> ORGANISM: Rattus norvegicus

<400> SEQUENCE: 12
ttatgaatga cctcgatggc ttc                                              23

<210> SEQ ID NO 13
<211> LENGTH: 17
<212> TYPE: DNA
<213> ORGANISM: Rattus norvegicus

<400> SEQUENCE: 13
agtaggggat tggggat                                                     17

<210> SEQ ID NO 14
<211> LENGTH: 20
```

```
<212> TYPE: DNA
<213> ORGANISM: Rattus norvegicus

<400> SEQUENCE: 14
tctataagtg gccsctggct                                          20

<210> SEQ ID NO 15
<211> LENGTH: 20
<212> TYPE: DNA
<213> ORGANISM: Rattus norvegicus

<400> SEQUENCE: 15
gacctggatg gaaatggctt                                          20

<210> SEQ ID NO 16
<211> LENGTH: 20
<212> TYPE: DNA
<213> ORGANISM: Rattus norvegicus

<400> SEQUENCE: 16
actcgacagg cattgctttg                                          20

<210> SEQ ID NO 17
<211> LENGTH: 20
<212> TYPE: DNA
<213> ORGANISM: Rattus norvegicus

<400> SEQUENCE: 17
atcaccatct tccaggagcg                                          20

<210> SEQ ID NO 18
<211> LENGTH: 20
<212> TYPE: DNA
<213> ORGANISM: Rattus norvegicus

<400> SEQUENCE: 18
gatggcatgg actgtggtca                                          20

<210> SEQ ID NO 19
<211> LENGTH: 25
<212> TYPE: DNA
<213> ORGANISM: Rattus norvegicus

<400> SEQUENCE: 19
cctttgcttc cttcttgaaa tctat                                    25

<210> SEQ ID NO 20
<211> LENGTH: 20
<212> TYPE: DNA
<213> ORGANISM: Rattus norvegicus

<400> SEQUENCE: 20
gacgtcaata atgacgtatg                                          20

<210> SEQ ID NO 21
<211> LENGTH: 22
<212> TYPE: DNA
<213> ORGANISM: Rattus norvegicus

<400> SEQUENCE: 21
ggtaatagcg atgactaata cg                                       22

<210> SEQ ID NO 22
```

<211> LENGTH: 564
<212> TYPE: PRT
<213> ORGANISM: Homo sapiens

<400> SEQUENCE: 22

Met Gly Asn Trp Val Val Asn His Trp Phe Ser Val Leu Phe Leu Val
1               5                   10                  15

Val Trp Leu Gly Leu Asn Val Phe Leu Phe Val Asp Ala Phe Leu Lys
            20                  25                  30

Tyr Glu Lys Ala Asp Lys Tyr Tyr Tyr Thr Arg Lys Ile Leu Gly Ser
        35                  40                  45

Thr Leu Ala Cys Ala Arg Ala Ser Ala Leu Cys Leu Asn Phe Asn Ser
50                  55                  60

Thr Leu Ile Leu Leu Pro Val Cys Arg Asn Leu Leu Ser Phe Leu Arg
65                  70                  75                  80

Gly Thr Cys Ser Phe Cys Ser Arg Thr Leu Arg Lys Gln Leu Asp His
                85                  90                  95

Asn Leu Thr Phe His Lys Leu Val Ala Tyr Met Ile Cys Leu His Thr
            100                 105                 110

Ala Ile His Ile Ile Ala His Leu Phe Asn Phe Asp Cys Tyr Ser Arg
        115                 120                 125

Ser Arg Gln Ala Thr Asp Gly Ser Leu Ala Ser Ile Leu Ser Ser Leu
130                 135                 140

Ser His Asp Glu Lys Lys Gly Gly Ser Trp Leu Asn Pro Ile Gln Ser
145                 150                 155                 160

Arg Asn Thr Thr Val Glu Tyr Val Thr Phe Thr Ser Ile Ala Gly Leu
                165                 170                 175

Thr Gly Val Ile Met Thr Ile Ala Leu Ile Leu Met Val Thr Ser Ala
            180                 185                 190

Thr Glu Phe Ile Arg Arg Ser Tyr Phe Glu Val Phe Trp Tyr Thr His
        195                 200                 205

His Leu Phe Ile Phe Tyr Ile Leu Gly Leu Gly Ile His Gly Ile Gly
210                 215                 220

Gly Ile Val Arg Gly Gln Thr Glu Glu Ser Met Asn Glu Ser His Pro
225                 230                 235                 240

Arg Lys Cys Ala Glu Ser Phe Glu Met Trp Asp Asp Arg Asp Ser His
                245                 250                 255

Cys Arg Arg Pro Lys Phe Glu Gly His Pro Pro Glu Ser Trp Lys Trp
            260                 265                 270

Ile Leu Ala Pro Val Ile Leu Tyr Ile Cys Glu Arg Ile Leu Arg Phe
        275                 280                 285

Tyr Arg Ser Gln Gln Lys Val Val Ile Thr Lys Val Val Met His Pro
290                 295                 300

Ser Lys Val Leu Glu Leu Gln Met Asn Lys Arg Gly Phe Ser Met Glu
305                 310                 315                 320

Val Gly Gln Tyr Ile Phe Val Asn Cys Pro Ser Ile Ser Leu Leu Glu
                325                 330                 335

Trp His Pro Phe Thr Leu Thr Ser Ala Pro Glu Glu Asp Phe Phe Ser
            340                 345                 350

Ile His Ile Arg Ala Ala Gly Asp Trp Thr Glu Asn Leu Ile Arg Ala
        355                 360                 365

Phe Glu Gln Gln Tyr Ser Pro Ile Pro Arg Ile Glu Val Asp Gly Pro
370                 375                 380

Phe Gly Thr Ala Ser Glu Asp Val Phe Gln Tyr Glu Val Ala Val Leu

```
                385                 390                 395                 400
Val Gly Ala Gly Ile Gly Val Thr Pro Phe Ala Ser Ile Leu Lys Ser
                    405                 410                 415
Ile Trp Tyr Lys Phe Gln Cys Ala Asp His Asn Leu Lys Thr Lys Lys
                    420                 425                 430
Ile Tyr Phe Tyr Trp Ile Cys Arg Glu Thr Gly Ala Phe Ser Trp Phe
                    435                 440                 445
Asn Asn Leu Leu Thr Ser Leu Glu Gln Glu Met Glu Glu Leu Gly Lys
                    450                 455                 460
Val Gly Phe Leu Asn Tyr Arg Leu Phe Leu Thr Gly Trp Asp Ser Asn
465                 470                 475                 480
Ile Val Gly His Ala Ala Leu Asn Phe Asp Lys Ala Thr Asp Ile Val
                    485                 490                 495
Thr Gly Leu Lys Gln Lys Thr Ser Phe Gly Arg Pro Met Trp Asp Asn
                    500                 505                 510
Glu Phe Ser Thr Ile Ala Thr Ser His Pro Lys Ser Val Val Gly Val
                    515                 520                 525
Phe Leu Cys Gly Pro Arg Thr Leu Ala Lys Ser Leu Arg Lys Cys Cys
                    530                 535                 540
His Arg Tyr Ser Ser Leu Asp Pro Arg Lys Val Gln Phe Tyr Phe Asn
545                 550                 555                 560
Lys Glu Asn Phe

<210> SEQ ID NO 23
<211> LENGTH: 515
<212> TYPE: PRT
<213> ORGANISM: Homo sapiens

<400> SEQUENCE: 23

Met Gly Asn Trp Val Asn His Trp Phe Ser Val Leu Phe Leu Val
1                   5                   10                  15

Val Trp Leu Gly Leu Asn Val Phe Leu Phe Val Asp Ala Phe Leu Lys
                    20                  25                  30

Tyr Glu Lys Ala Asp Lys Tyr Tyr Tyr Thr Arg Lys Ile Leu Gly Ser
                    35                  40                  45

Thr Leu Ala Cys Ala Arg Ala Ser Ala Leu Cys Leu Asn Phe Asn Ser
                    50                  55                  60

Thr Leu Ile Leu Leu Pro Val Cys Arg Asn Leu Ser Phe Leu Arg
65                  70                  75                  80

Gly Thr Cys Ser Phe Cys Ser Arg Thr Leu Arg Lys Gln Leu Asp His
                    85                  90                  95

Asn Leu Thr Phe His Lys Leu Val Ala Tyr Met Ile Cys Leu His Thr
                    100                 105                 110

Ala Ile His Ile Ile Ala His Leu Phe Asn Phe Asp Cys Tyr Ser Arg
                    115                 120                 125

Ser Arg Gln Ala Thr Asp Gly Ser Leu Ala Ser Ile Leu Ser Ser Leu
                    130                 135                 140

Ser His Asp Glu Lys Lys Gly Gly Ser Trp Leu Asn Pro Ile Gln Ser
145                 150                 155                 160

Arg Asn Thr Thr Val Glu Tyr Val Thr Phe Thr Ser Ile Ala Gly Leu
                    165                 170                 175

Thr Gly Val Ile Met Thr Ile Ala Leu Ile Leu Met Val Thr Ser Ala
                    180                 185                 190

Thr Glu Phe Ile Arg Arg Ser Tyr Phe Glu Val Phe Trp Tyr Thr His
```

His Leu Phe Ile Phe Tyr Ile Leu Gly Leu Gly Ile His Gly Ile Gly
    210                 215                 220

Gly Ile Val Arg Gly Gln Thr Glu Glu Ser Met Asn Glu Ser His Pro
225                 230                 235                 240

Arg Lys Cys Ala Glu Ser Phe Glu Met Trp Asp Arg Asp Ser His
                    245                 250                 255

Cys Arg Arg Pro Lys Phe Glu Gly His Pro Pro Glu Ser Trp Lys Trp
                260                 265                 270

Ile Leu Ala Pro Val Ile Leu Tyr Ile Cys Glu Arg Ile Leu Arg Phe
            275                 280                 285

Tyr Arg Ser Gln Gln Lys Val Val Ile Thr Lys Val Val Met His Pro
        290                 295                 300

Ser Lys Val Leu Glu Leu Gln Met Asn Lys Arg Gly Phe Ser Met Glu
305                 310                 315                 320

Val Gly Gln Tyr Ile Phe Val Asn Cys Pro Ser Ile Ser Leu Leu Glu
                    325                 330                 335

Trp His Pro Phe Thr Leu Thr Ser Ala Pro Glu Glu Asp Phe Phe Ser
                340                 345                 350

Ile His Ile Arg Ala Ala Gly Asp Trp Thr Glu Asn Leu Ile Arg Ala
            355                 360                 365

Phe Glu Gln Gln Tyr Ser Pro Ile Pro Arg Ile Glu Val Asp Gly Pro
        370                 375                 380

Phe Gly Thr Ala Ser Glu Asp Val Phe Gln Tyr Glu Val Ala Val Leu
385                 390                 395                 400

Val Gly Ala Gly Ile Gly Val Thr Pro Phe Ala Ser Ile Leu Lys Ser
                    405                 410                 415

Ile Trp Tyr Lys Phe Gln Cys Ala Asp His Asn Leu Lys Thr Lys Lys
                420                 425                 430

Val Gly His Ala Ala Leu Asn Phe Asp Lys Ala Thr Asp Ile Val Thr
            435                 440                 445

Gly Leu Lys Gln Lys Thr Ser Phe Gly Arg Pro Met Trp Asp Asn Glu
        450                 455                 460

Phe Ser Thr Ile Ala Thr Ser His Pro Lys Ser Val Val Gly Val Phe
465                 470                 475                 480

Leu Cys Gly Pro Arg Thr Leu Ala Lys Ser Leu Arg Lys Cys Cys His
                    485                 490                 495

Arg Tyr Ser Ser Leu Asp Pro Arg Lys Val Gln Phe Tyr Phe Asn Lys
                500                 505                 510

Glu Asn Phe
        515

<210> SEQ ID NO 24
<211> LENGTH: 527
<212> TYPE: PRT
<213> ORGANISM: Homo sapiens

<400> SEQUENCE: 24

Met Gly Asn Trp Val Val Asn His Trp Phe Ser Val Leu Phe Leu Val
1               5                   10                  15

Val Trp Leu Gly Leu Asn Val Phe Leu Phe Val Asp Ala Phe Leu Lys
            20                  25                  30

Tyr Glu Lys Ala Asp Lys Tyr Tyr Tyr Thr Arg Lys Ile Leu Gly Phe
        35                  40                  45

```
Cys Ser Arg Thr Leu Arg Lys Gln Leu Asp His Asn Leu Thr Phe His
         50                  55                  60

Lys Leu Val Ala Tyr Met Ile Cys Leu His Thr Ala Ile His Ile Ile
 65                  70                  75                  80

Ala His Leu Phe Asn Phe Asp Cys Tyr Ser Arg Ser Arg Gln Ala Thr
                     85                  90                  95

Asp Gly Ser Leu Ala Ser Ile Leu Ser Ser Leu Ser His Asp Glu Lys
                100                 105                 110

Lys Gly Gly Ser Trp Leu Asn Pro Ile Gln Ser Arg Asn Thr Thr Val
            115                 120                 125

Glu Tyr Val Thr Phe Thr Ser Ile Ala Gly Leu Thr Gly Val Ile Met
    130                 135                 140

Thr Ile Ala Leu Ile Leu Met Val Thr Ser Ala Thr Glu Phe Ile Arg
145                 150                 155                 160

Arg Ser Tyr Phe Glu Val Phe Trp Tyr Thr His His Leu Phe Ile Phe
                165                 170                 175

Tyr Ile Leu Gly Leu Gly Ile His Gly Ile Gly Gly Ile Val Arg Gly
                180                 185                 190

Gln Thr Glu Glu Ser Met Asn Glu Ser His Pro Arg Lys Cys Ala Glu
            195                 200                 205

Ser Phe Glu Met Trp Asp Asp Arg Asp Ser His Cys Arg Arg Pro Lys
    210                 215                 220

Phe Glu Gly His Pro Pro Glu Ser Trp Lys Trp Ile Leu Ala Pro Val
225                 230                 235                 240

Ile Leu Tyr Ile Cys Glu Arg Ile Leu Arg Phe Tyr Arg Ser Gln Gln
                245                 250                 255

Lys Val Val Ile Thr Lys Val Val Met His Pro Ser Lys Val Leu Glu
                260                 265                 270

Leu Gln Met Asn Lys Arg Gly Phe Ser Met Glu Val Gly Gln Tyr Ile
            275                 280                 285

Phe Val Asn Cys Pro Ser Ile Ser Leu Leu Glu Trp His Pro Phe Thr
    290                 295                 300

Leu Thr Ser Ala Pro Glu Glu Asp Phe Phe Ser Ile His Ile Arg Ala
305                 310                 315                 320

Ala Gly Asp Trp Thr Glu Asn Leu Ile Arg Ala Phe Glu Gln Gln Tyr
                325                 330                 335

Ser Pro Ile Pro Arg Ile Glu Val Asp Gly Pro Phe Gly Thr Ala Ser
                340                 345                 350

Glu Asp Val Phe Gln Tyr Glu Val Ala Val Leu Val Gly Ala Gly Ile
            355                 360                 365

Gly Val Thr Pro Phe Ala Ser Ile Leu Lys Ser Ile Trp Tyr Lys Phe
    370                 375                 380

Gln Cys Ala Asp His Asn Leu Lys Thr Lys Lys Ile Tyr Phe Tyr Trp
385                 390                 395                 400

Ile Cys Arg Glu Thr Gly Ala Phe Ser Trp Phe Asn Asn Leu Leu Thr
                405                 410                 415

Ser Leu Glu Gln Glu Met Glu Glu Leu Gly Lys Val Gly Phe Leu Asn
                420                 425                 430

Tyr Arg Leu Phe Leu Thr Gly Trp Asp Ser Asn Ile Val Gly His Ala
            435                 440                 445

Ala Leu Asn Phe Asp Lys Ala Thr Asp Ile Val Thr Gly Leu Lys Gln
    450                 455                 460

Lys Thr Ser Phe Gly Arg Pro Met Trp Asp Asn Glu Phe Ser Thr Ile
```

```
                   465                 470                 475                 480
                Ala Thr Ser His Pro Lys Ser Val Val Gly Val Phe Leu Cys Gly Pro
                                485                 490                 495

Arg Thr Leu Ala Lys Ser Leu Arg Lys Cys Cys His Arg Tyr Ser Ser
                                500                 505                 510

Leu Asp Pro Arg Lys Val Gln Phe Tyr Phe Asn Lys Glu Asn Phe
                                515                 520                 525

<210> SEQ ID NO 25
<211> LENGTH: 563
<212> TYPE: PRT
<213> ORGANISM: Mus musculus

<400> SEQUENCE: 25

Met Gly Asn Trp Leu Val Asn His Trp Leu Ser Val Leu Phe Leu Val
1               5                   10                  15

Ser Trp Leu Gly Leu Asn Ile Phe Leu Phe Val Tyr Ala Phe Leu Asn
                20                  25                  30

Tyr Glu Lys Ser Asp Lys Tyr Tyr Thr Arg Glu Ile Leu Gly Thr
            35                  40                  45

Ala Leu Ala Leu Ala Arg Ala Ser Ala Leu Cys Leu Asn Phe Asn Ser
        50                  55                  60

Met Met Ile Leu Ile Pro Val Cys Arg Asn Leu Leu Ser Phe Leu Arg
65                  70                  75                  80

Gly Thr Cys Ser Phe Cys Asn Arg Thr Leu Arg Lys Pro Leu Asp His
                85                  90                  95

Asn Leu Thr Phe His Lys Leu Val Ala Tyr Met Ile Cys Ile Phe Thr
            100                 105                 110

Val Ile His Ile Ile Ala His Leu Phe Asn Phe Glu Arg Tyr Arg Arg
        115                 120                 125

Ser Gln Gln Ala Met Asp Gly Ser Leu Ala Ser Val Leu Ser Ser Leu
    130                 135                 140

Ser His Pro Glu Lys Glu Asp Ser Trp Leu Asn Pro Ile Gln Ser Pro
145                 150                 155                 160

Asn Met Thr Val Met Tyr Ala Ala Phe Thr Ser Ile Ala Gly Leu Thr
                165                 170                 175

Gly Val Ile Ala Thr Val Ala Leu Val Leu Met Val Thr Ser Ala Met
            180                 185                 190

Glu Phe Ile Arg Arg Asn Tyr Phe Glu Leu Phe Trp Tyr Thr His His
        195                 200                 205

Leu Phe Ile Val Tyr Ile Ile Cys Leu Gly Ile His Gly Leu Gly Gly
    210                 215                 220

Ile Val Arg Gly Gln Thr Glu Glu Ser Leu Gly Glu Ser His Pro His
225                 230                 235                 240

Asn Cys Ser His Ser Phe His Glu Trp Asp Asp His Lys Gly Ser Cys
                245                 250                 255

Arg His Pro His Phe Ala Gly His Pro Pro Glu Ser Trp Lys Trp Ile
            260                 265                 270

Leu Ala Pro Ile Ala Phe Tyr Ile Phe Glu Arg Ile Leu Arg Phe Tyr
        275                 280                 285

Arg Ser Gln Gln Lys Val Val Ile Thr Lys Val Val Met His Pro Ser
    290                 295                 300

Asn Val Leu Glu Leu Gln Met Arg Lys Arg Gly Phe Ser Met Glu Val
305                 310                 315                 320
```

Gly Gln Tyr Ile Phe Val Asn Cys Pro Ser Ile Ser Phe Leu Glu Trp
                325                 330                 335

His Pro Phe Thr Leu Thr Ser Ala Pro Glu Glu Phe Ser Val
            340                 345                 350

His Ile Arg Ala Ala Gly Asp Trp Thr Arg Asn Leu Ile Arg Thr Phe
            355                 360                 365

Glu Gln Gln His Ser Pro Met Pro Arg Ile Glu Val Asp Gly Pro Phe
370                 375                 380

Gly Thr Val Ser Glu Asp Val Phe Gln Tyr Glu Val Ala Val Leu Val
385                 390                 395                 400

Gly Ala Gly Ile Gly Val Thr Pro Phe Ala Ser Ile Leu Lys Ser Ile
                405                 410                 415

Trp Tyr Lys Phe Gln Arg Ala Asp Asn Lys Leu Lys Thr Gln Lys Ile
                420                 425                 430

Tyr Phe Tyr Trp Ile Cys Arg Glu Thr Gly Ala Phe Ala Trp Phe Asn
            435                 440                 445

Asn Leu Leu Asn Ser Leu Glu Gln Glu Met Glu Leu Gly Lys Met
    450                 455                 460

Asp Phe Leu Asn Tyr Arg Leu Phe Leu Thr Gly Trp Asp Ser Asn Ile
465                 470                 475                 480

Ala Gly His Ala Ala Leu Asn Phe Asp Arg Ala Thr Asp Ile Leu Thr
                485                 490                 495

Gly Leu Lys Gln Lys Thr Ser Phe Gly Arg Pro Met Trp Asp Asn Glu
                500                 505                 510

Phe Ser Arg Ile Ala Thr Ala His Pro Lys Ser Ala Val Gly Val Phe
            515                 520                 525

Leu Cys Gly Pro Arg Thr Leu Ala Lys Ser Leu Arg Lys Arg Cys Gln
            530                 535                 540

Arg Tyr Ser Ser Leu Asp Pro Arg Lys Val Gln Phe Tyr Phe Asn Lys
545                 550                 555                 560

Glu Thr Phe

<210> SEQ ID NO 26
<211> LENGTH: 563
<212> TYPE: PRT
<213> ORGANISM: Rattus norvegicus

<400> SEQUENCE: 26

Met Gly Asn Trp Leu Val Asn His Trp Leu Ser Val Leu Phe Leu Val
1               5                   10                  15

Ser Trp Leu Gly Leu Asn Ile Phe Leu Phe Val Tyr Val Phe Leu Asn
                20                  25                  30

Tyr Glu Lys Ser Asp Lys Tyr Tyr Tyr Thr Arg Glu Ile Leu Gly Thr
            35                  40                  45

Ala Leu Ala Leu Ala Arg Ala Ser Ala Leu Cys Leu Asn Phe Asn Ser
        50                  55                  60

Met Val Ile Leu Ile Pro Val Cys Arg Asn Leu Leu Ser Phe Leu Arg
65                  70                  75                  80

Gly Thr Cys Ser Phe Cys Asn His Thr Leu Arg Lys Pro Leu Asp His
                85                  90                  95

Asn Leu Thr Phe His Lys Leu Val Ala Tyr Met Ile Cys Ile Phe Thr
            100                 105                 110

Ala Ile His Ile Ile Ala His Leu Phe Asn Phe Glu Arg Tyr Ser Arg
        115                 120                 125

-continued

```
Ser Gln Gln Ala Met Asp Gly Ser Leu Ala Ser Val Leu Ser Ser Leu
    130                 135                 140
Phe His Pro Glu Lys Glu Asp Ser Trp Leu Asn Pro Ile Gln Ser Pro
145                 150                 155                 160
Asn Val Thr Val Met Tyr Ala Ala Phe Thr Ser Ile Ala Gly Leu Thr
                    165                 170                 175
Gly Val Val Ala Thr Val Ala Leu Val Leu Met Val Thr Ser Ala Met
                180                 185                 190
Glu Phe Ile Arg Arg Asn Tyr Phe Glu Leu Phe Trp Tyr Thr His His
                195                 200                 205
Leu Phe Ile Ile Tyr Ile Ile Cys Leu Gly Ile His Gly Leu Gly Gly
    210                 215                 220
Ile Val Arg Gly Gln Thr Glu Glu Ser Met Ser Glu Ser His Pro Arg
225                 230                 235                 240
Asn Cys Ser Tyr Ser Phe His Glu Trp Asp Lys Tyr Glu Arg Ser Cys
                    245                 250                 255
Arg Ser Pro His Phe Val Gly Gln Pro Pro Glu Ser Trp Lys Trp Ile
                260                 265                 270
Leu Ala Pro Ile Ala Phe Tyr Ile Phe Glu Arg Ile Leu Arg Phe Tyr
    275                 280                 285
Arg Ser Arg Gln Lys Val Val Ile Thr Lys Val Val Met His Pro Cys
290                 295                 300
Lys Val Leu Glu Leu Gln Met Arg Lys Arg Gly Phe Thr Met Gly Ile
305                 310                 315                 320
Gly Gln Tyr Ile Phe Val Asn Cys Pro Ser Ile Ser Phe Leu Glu Trp
                    325                 330                 335
His Pro Phe Thr Leu Thr Ser Ala Pro Glu Glu Glu Phe Phe Ser Ile
                340                 345                 350
His Ile Arg Ala Ala Gly Asp Trp Thr Glu Asn Leu Ile Arg Thr Phe
    355                 360                 365
Glu Gln Gln His Ser Pro Met Pro Arg Ile Glu Val Asp Gly Pro Phe
370                 375                 380
Gly Thr Val Ser Glu Asp Val Phe Gln Tyr Glu Val Ala Val Leu Val
385                 390                 395                 400
Gly Ala Gly Ile Gly Val Thr Pro Phe Ala Ser Phe Leu Lys Ser Ile
                    405                 410                 415
Trp Tyr Lys Phe Gln Arg Ala His Asn Lys Leu Lys Thr Gln Lys Ile
                420                 425                 430
Tyr Phe Tyr Trp Ile Cys Arg Glu Thr Gly Ala Phe Ala Trp Phe Asn
    435                 440                 445
Asn Leu Leu Asn Ser Leu Glu Gln Glu Met Asp Glu Leu Gly Lys Pro
450                 455                 460
Asp Phe Leu Asn Tyr Arg Leu Phe Leu Thr Gly Trp Asp Ser Asn Ile
465                 470                 475                 480
Ala Gly His Ala Ala Leu Asn Phe Asp Arg Ala Thr Asp Val Leu Thr
                    485                 490                 495
Gly Leu Lys Gln Lys Thr Ser Phe Gly Arg Pro Met Trp Asp Asn Glu
                500                 505                 510
Phe Ser Arg Ile Ala Thr Ala His Pro Lys Ser Val Val Gly Val Phe
    515                 520                 525
Leu Cys Gly Pro Pro Thr Leu Ala Lys Ser Leu Arg Lys Cys Cys Arg
530                 535                 540
Arg Tyr Ser Ser Leu Asp Pro Arg Lys Val Gln Phe Tyr Phe Asn Lys
```

```
545            550            555            560
Glu Thr Phe

<210> SEQ ID NO 27
<211> LENGTH: 29
<212> TYPE: DNA
<213> ORGANISM: Homo sapiens

<400> SEQUENCE: 27
tgaatgagag tcatcctcgc aagtgtgca                                   29

<210> SEQ ID NO 28
<211> LENGTH: 29
<212> TYPE: DNA
<213> ORGANISM: Homo sapiens

<400> SEQUENCE: 28
tgaatgagag tcatcctcgc aagtgtgca                                   29

<210> SEQ ID NO 29
<211> LENGTH: 29
<212> TYPE: DNA
<213> ORGANISM: Homo sapiens

<400> SEQUENCE: 29
tgaagtggct gtgctggttg gagcaggaa                                   29

<210> SEQ ID NO 30
<211> LENGTH: 29
<212> TYPE: DNA
<213> ORGANISM: Homo sapiens

<400> SEQUENCE: 30
acagtggagt atgtgacatt caccagcat                                   29

<210> SEQ ID NO 31
<211> LENGTH: 29
<212> TYPE: DNA
<213> ORGANISM: Rattus norvegicus

<400> SEQUENCE: 31
caaccacacg ctgagaaagc cattggatc                                   29

<210> SEQ ID NO 32
<211> LENGTH: 29
<212> TYPE: DNA
<213> ORGANISM: Rattus norvegicus

<400> SEQUENCE: 32
ccgcaactgt tcatactctt tccacgagt                                   29

<210> SEQ ID NO 33
<211> LENGTH: 29
<212> TYPE: DNA
<213> ORGANISM: Rattus norvegicus

<400> SEQUENCE: 33
ttggcacagt cagtgaggat gtcttccag                                   29

<210> SEQ ID NO 34
<211> LENGTH: 29
<212> TYPE: DNA
<213> ORGANISM: Rattus norvegicus
```

```
<400> SEQUENCE: 34
cctaaactac cgactcttcc tcactggct                                            29

<210> SEQ ID NO 35
<211> LENGTH: 25
<212> TYPE: DNA
<213> ORGANISM: Rattus norvegicus

<400> SEQUENCE: 35
cctttgcttc cttcttgaaa tctat                                                25

<210> SEQ ID NO 36
<211> LENGTH: 29
<212> TYPE: DNA
<213> ORGANISM: Mus musculus

<400> SEQUENCE: 36
gccttactgg agtgattgcc actgtagct                                            29

<210> SEQ ID NO 37
<211> LENGTH: 29
<212> TYPE: DNA
<213> ORGANISM: Mus musculus

<400> SEQUENCE: 37
ttctgtttgt gtatgccttc ctgaattat                                            29

<210> SEQ ID NO 38
<211> LENGTH: 29
<212> TYPE: DNA
<213> ORGANISM: Mus musculus

<400> SEQUENCE: 38
tctaaactac cgtctcttcc tcactggct                                            29

<210> SEQ ID NO 39
<211> LENGTH: 29
<212> TYPE: DNA
<213> ORGANISM: Mus musculus

<400> SEQUENCE: 39
ggtcgtgatt accaaggttg tcatgcacc                                            29

<210> SEQ ID NO 40
<211> LENGTH: 29
<212> TYPE: DNA
<213> ORGANISM: Homo sapiens

<400> SEQUENCE: 40
aatgtccgtg caaagtggta tcctgaggt                                            29

<210> SEQ ID NO 41
<211> LENGTH: 29
<212> TYPE: DNA
<213> ORGANISM: Homo sapiens

<400> SEQUENCE: 41
gatgtgagtg gagcggccat ttcctgttt                                            29

<210> SEQ ID NO 42
<211> LENGTH: 29
<212> TYPE: DNA
```

```
<213> ORGANISM: Homo sapiens

<400> SEQUENCE: 42
gatgtgagtg gagcggccat ttcctgttt                                29

<210> SEQ ID NO 43
<211> LENGTH: 29
<212> TYPE: DNA
<213> ORGANISM: Homo sapiens

<400> SEQUENCE: 43
gcgttgccat tgaactcacc agtgagtta                                29
```

AMELIORATING OXIDATIVE STRESS IN NEURODEGENERATIVE DISEASE VIA NOX1 TARGETING

CROSS-REFERENCE TO RELATED APPLICATIONS

This application is related to U.S. Provisional Application No. 61/756,416 filed Jan. 24, 2013 to which priority is claimed under 35 USC 119, and incorporated in its entirety by this reference.

STATEMENT OF GOVERNMENT SUPPORT

The invention was made with government support under R01 NS062827 awarded by the National Institutes of Health. The government has certain rights in the invention.

BACKGROUND

Oxidative damage to specific neurons in the central nervous system (CNS) is a commonly observed pathophysiologic feature of neurodegenerative diseases such as Parkinson's disease (PD) and Alzheimer's disease (AD). A wide range of oxidative damage to cellular macromolecules in nigrostriatal dopaminergic neurons, including lipids, proteins, and nucleotides, has been observed in postmortem brains of PD patients. The molecular mechanism underlying selective susceptibility of the nigrostriatal pathway to oxidative stress remains unresolved. Mitochondrial dysfunctions, including selective decrease in respiratory complex I activity and mitochondrial DNA abnormality (Bender et al. 2006, Schapira et al. 1989), are implicated in the pathogenesis of PD partly through an increase in the production of the reactive oxygen species (ROS). Moreover, a significant increase in oxidative damage to DNA in both nucleus and mitochondria has been observed in dopaminergic neurons in the substantia nigra (SN) of PD patients (Alam et al. 1997, Migliore et al. 2002, Sherer et al. 2005). However, the mechanisms of DNA damage, especially nuclear DNA damage, are obscure.

DETAILED DESCRIPTION

Figure 1:
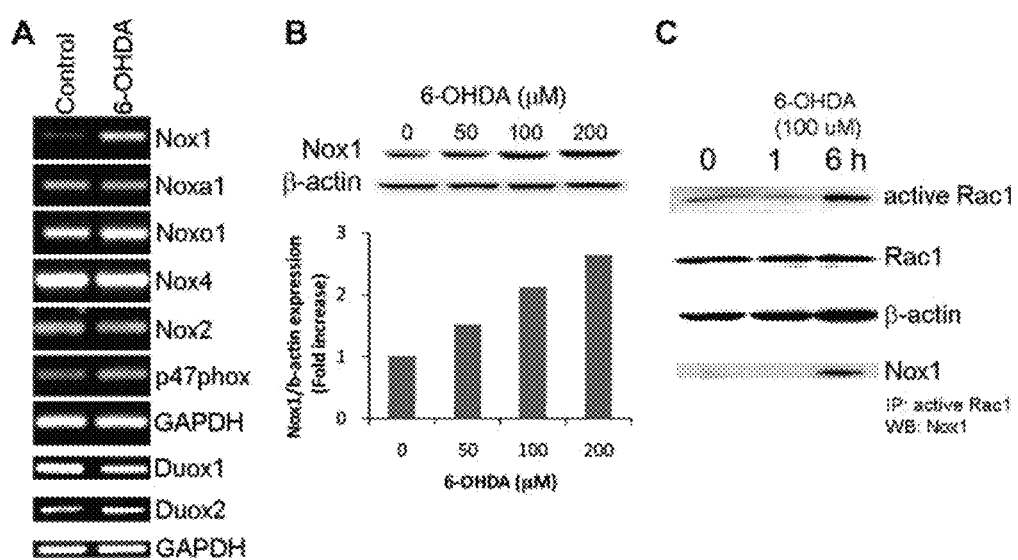
FIG. 1 Dopaminergic cells contain NADPH oxidase components and 6-ohda leads to Nox1 induction and Rac1 activation. (A) mRna of Nox isoforms and subunits were detected using RT-PCR in N27 cells treated with 6-OHDA (100 μM) for 6 h. GAPDH, internal control; control, vehicle treated. (B) 24 h 6-OHDA treatment increased Nox1 expression in a dose-dependent manner as examined by immunoblot analysis. Signal intensity was measured by Quantity One software and shown as fold increase. β-actin, internal control. (C) GTP-bound active Rac1 was increased by 6-OHDA treatment for various durations (1 h and 6 h) as determined by the active GTPase pull-down assay. Nox1, coprecipitated with active Rac1, was detected in the same blot using Western blot analysis. Total Rac1 and β-actin were demonstrated as internal controls. Images are representative of three independent experiments.

In the present disclosure, it has been shown that Nox1/Rac1 is activated in dopaminergic neurons under stress conditions, causing oxidative stress and consequential neuronal death. Nuclear localization of Nox1 and oxidative DNA damage were observed in both rodent PD model and postmortem human PD brain tissue. AAV-mediated targeting against Nox1/Rac1 protects dopaminergic neurons under 6-OHDA toxicity, demonstrating Nox1 and Rac1 as novel molecular targets for therapeutic intervention in PD.

Disclosed are methods of ameliorating, preventing, delaying the onset or improving an unwanted condition, disease or symptom of a patient associated with oxidative stress. In particular, the method involves the modulating Nox1 activity in neurons in a subject in need thereof, such as a subject under oxidative stress in response to Nox1 or experiencing symptoms of Parkinson's disease or other neurodegenerative diseases.

In a particular embodiment, provided is a method for treating Parkinson's Disease in a subject, comprising administering to the subject a therapeutically effective amount of a composition that inhibits the expression or action of NADPH oxidase 1 (Nox1) in the subject.

As used herein and in the appended claims, the singular forms "a", "an", and "the" include plural reference unless the context clearly dictates otherwise. Thus, for example, reference to an "compound" is a reference to one or more compounds and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic to a patient whereby the therapeutic positively impacts the tissue to which it is targeted. The compounds described herein can be administered either alone or in combination (concurrently or serially) with other pharmaceuticals. For example, the compounds can be administered in combination with other antioxidants or agents known to treat the target condition. In some embodiments, the compounds described herein can also be administered in combination with (i.e., as a combined formulation or as separate formulations) with antibiotics.

The terms "animal," "patient," or "subject" are used interchangeably, and include, but are not limited to, humans and non-human vertebrates such as wild, domestic and farm animals. Typically, the term refers to humans.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, prevent or improve an unwanted condition, disease or symptom of a patient.

A "therapeutically effective amount" or "effective amount" of a composition is a predetermined amount calculated to achieve the desired effect, i.e., to ameliorate, prevent or improve an unwanted condition, disease or symptom of a patient. In a specific example, a therapeutically effective amount is one that reduces the adverse cellular effects of oxidants such as reactive oxygen species (ROS) or free radicals, including those associated with Nox1 activity in neurons. The activity contemplated by the present methods includes both therapeutic and/or prophylactic treatment, as appropriate. The specific dose of the compounds or the compounds administered according to this invention to obtain therapeutic and/or prophylactic effects will, of course, be determined by the particular circumstances surrounding the case, including, for example, the compounds administered, the route of administration, and the condition being treated. The effective amount administered may be determined by a physician in the light of the relevant circumstances including the condition to be treated, the choice of compounds to be administered, and the chosen route of administration. A therapeutically effective amount of the compound/compound of this invention is typically an amount such that when it is administered in a physiologically tolerable excipient composition, it is sufficient to achieve an effective systemic concentration or local concentration in the target tissue.

Generally speaking, the term "tissue" refers to any aggregation of similarly specialized cells which are united in the performance of a particular function.

Parkinson's disease (PD) is a progressive neurodegenerative disease characterized by resting tremors, bradykinesia, muscular rigidity, and postural instability. PD typically develops after the age of 60, though 15% of diagnosed patients are under the age of 50. Family history of PD is an etiological factor for 5-10% of patients diagnosed with the disease, yet only 1% of cases have been shown to be clearly familial. It is estimated that 1.5 million Americans are currently living with PD. In an alternative embodiment, Nox1 or Rac1 inhibiting compound is administered to a subject exhibiting symptoms of PD. Symptoms of PD include resting tremor, bradykinesia, muscle rigidity, postural instability, freezing of gait, micrographia, "mask-face", or uncontrolled accelerative movements.

Alzheimer's disease (AD) is a progressive neurodegenerative disorder characterized by cognitive decline, irreversible memory loss, disorientation, and language impairment. AD affects 10% of the population aged greater than 65 and at least 50% of the population aged greater than 85 years. AD has been reported in patients as young as 40-50 years of age, but because the presence of the disease is difficult to detect without histopathological examination of brain tissue, the time of onset in living subjects is unknown. Several etiological factors have been implicated in the pathogenesis of Alzheimer's disease. These factors lead to the activation of a cascade process that brings about neuronal death and serious decline in cognitive function. These bed-ridden patients ultimately succumb to death due to inter-current infections related to aspiration, decubitus and stagnation of urine. In one embodiment, a Nox1 or Rac1 inhibiting compound is administered to a subject exhibiting symptoms of AD, including for example decrease cognitive function.

Dementia with Lewy Bodies (DLB) is a progressive brain disease having symptoms that fluctuate between various degrees of manifestation. These symptoms include progressive dementia, Parkinsonian movement difficulties, hallucinations, and increased sensitivity to neuroleptic drugs. As with AD, advanced age is considered to be the greatest risk factor for DLB, with average onset usually between the ages of 50-85. Further, 20% of all dementia cases are caused by DLB and over 50% of PD patients develop "Parkinson's Disease Dementia" (PDD), a type of DLB. It is possible for DLB to occur alone, or in conjunction with other brain abnormalities, including those involved in AD and PD, as mentioned above. In a further embodiment, a Nox1 or Rac1 inhibiting compound is administered to a subject exhibiting symptoms of DLB.

In a specific embodiment, disclosed is an adeno-associated virus serotype 2 (AAV2)-mediated overexpression or knockdown system and an effective method for the genetic intervention of Nox1 and Rac1, specifically in SN dopaminergic neurons in vivo. Further presented is the critical evidence that accumulation of the Nox1/Rac1 complex and ROS in the nucleus of SN dopaminergic neurons is directly responsible for nuclear DNA damage which leads to dopaminergic neurodegeneration. Also the genetic intervention to Nox1 and Rac1 and the chemical inhibition of Nox1, protect nuclear DNA from damage and thus are neuroprotective.

Target Sequences

The NADPH oxidase is a multi-subunit enzyme that consists of the catalytic subunits (Nox isoforms) together with the regulatory subunits including p22phox, p47phox, p40phox, p67phox, Nox organizer 1 (Noxo1), Nox activator 1 (Noxa1), and small GTPase Rac1. A non-limiting list of target sequences for inhibition of NADPH oxidase are set forth in the Examples and on Appendix A.

The GenBank database provides the nucleic acid sequences for Nox1 and variants as accession nos. NM_001271815, NM_007052, NM_013954, NM_013955, NM_053683 (rat) and NM_172203 (mouse) and provides nucleic acid sequences for Rac 1 as NM_018890.3, NM_006908.4, NM_134366 (rat) and NM_009007.2 (mouse). Appendix A sets forth various sequences of polypeptides encoded by Nox1 genes in human, mouse and rat, as well as target sequences for purposes of RNA interference gene expression reduction strategies or other expression reduction strategies. As used herein, a cognate is a NOX1

AND RAC1 mRNA from another mammalian species that is homologous to the cited human form (i.e., an ortholog).

Compounds

Compounds of the present disclosure pertain to those able to modulate expression, RNA processing, translation or activity of NADPH oxidase related enzyme or components thereof. Such compounds are also referred to herein as NOI (NADPH oxidase inhibiting) compounds. The NOI compounds may be a RNA interfering molecule, antibody, antisense molecule, PMO, ribozyme or small molecule. Compounds or NOI compounds as used herein include not only refer to the inhibitor but also refer to a delivery vehicle for providing the inhibitor. For example, reference to NOI compound or compound may refer to RNA interfering molecule or to a viral vector or delivery vector including a sequence to express the RNA interfering molecule.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-related cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

The term "siRNA" as used herein refers to a double-stranded interfering RNA unless otherwise noted. Typically, an siRNA of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). The phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules can interact with RISC and silence gene expression. Examples of other interfering RNA molecules that can interact with RISC include short hairpin RNAs (shRNAs), single-stranded siRNAs, microRNAs (miRNAs), and dicer-substrate 27-mer duplexes. Examples of RNA-like molecules that can interact with RISC include siRNA, single-stranded siRNA, microRNA, and shRNA molecules containing one or more chemically modified nucleotides, one or more non-nucleotides, one or more deoxyribonucleotides, and/or one or more non-phosphodiester linkages. All RNA or RNA-like molecules that can interact with RISC and participate in RISC-related changes in gene expression are referred to herein as "interfering RNAs" or "interfering RNA molecules." SiRNAs, single-stranded siRNAs, shRNAs, miRNAs, and dicer-substrate 27-mer duplexes are, therefore, subsets of "interfering RNAs" or "interfering RNA molecules."

Single-stranded interfering RNA has been found to effect mRNA silencing, albeit less efficiently than double-stranded RNA. Therefore, embodiments of the present invention also provide for administration of a single-stranded interfering RNA that has a region of at least near-perfect contiguous complementarity with a portion of the NOX1 or RAC1 mRNA. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

In certain embodiments, interfering RNA target sequences (e.g., si RNA target sequences) within a target mRNA sequence are selected using available design tools. Interfering RNAs corresponding to a NOX1 or RAC1 target sequence are then tested in vitro by transfection of cells expressing the target mRNA followed by assessment of knockdown as described herein. The interfering RNAs can be further evaluated in vivo using animal models as described herein.

Techniques for selecting target sequences for si RNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and si RNA lengths between 19 and 27 nucleotides. The target sequence may be located in the coding region or in the 5' or 3' untranslated regions of the mRNA. The target sequences can be used to derive interfering RNA molecules, such as those described herein.

In certain embodiments, silencing of human NOX1 or RAC1 genes may be based on the sequences provided in Appendix A.

Many of the embodiments of the subject invention make reference to particular methods of inhibiting or disruption of genetic expression. Based on the teachings herein, methods of inhibiting expression include but are not limited to siRNA; ribozyme(s); antibody(ies); antisense/oligonucleotide(s); morpholino oligomers; microRNA; or shRNA that target expression of the HK alpha-2 protein. The subject invention is not to be limited to any of the particular related methods described. One such method includes sRNA (small interfering/short interfering/silencing RNA). SiRNA most often is involved in the RNA interference pathway where it interferes with the expression of a specific gene. In addition to its role in the RNA interference pathway, sRNA also act in RNA interference-related pathways, e.g., as an antiviral mechanism or in shaping the chromatin structure of a genome.

Another method by which to inhibit expression and to inhibit the expression of Nox1 or Rac1 in particular is shRNA. ShRNA (short hairpin or small hairpin RNA) refers to a sequence of RNA that makes a tight hairpin turn and is used to silence gene expression via RNA interference. It uses a vector introduced into cells and a U6 or H1 promoter to ensure that the shRNA is always expressed. The shRNA hairpin structure is cleaved by cellular machinery into sRNA which is then bound to the RNA-induced silencing complex. This complex binds to and cleaves mRNAs which match the sRNA that is bound to it.

Nox1 or Rac1 can also be blocked by subjecting procured cells to an antibody specific to Nox1 or Rac1. An antisense nucleotide may also be used to block or inhibit expression, in particular, the expression of Nox1 or Rac1. Expression may also be inhibited with the use of a morpholino oligomer or phosphorodiamidate morpholino oligomer (PMO). PMOs are an antisense technology used to block access of other molecules to specific sequences within nucleic acid. PMOs are often used as a research tool for reverse genetics, and function by knocking down gene function. This is achieved by preventing cells from making a targeted protein or by modifying splicing of pre-mRNA. One embodiment of the subject disclosure pertains to a method of treating neurons under oxidative stress by expressing an RNA interfering molecule, antisense molecule or PMO in a subject in need thereof.

Vectors

In some embodiments, viral vectors are used to transfect cells with a NOI. In a particular embodiment, adeno-associated viral vectors are used. Other vectors of the invention used in vitro, in vivo, and ex vivo include viral vectors, such as retroviruses (including lentiviruses), herpes viruses, alphavirus, adenovirus, vaccinia virus, papillomavirus, or Epstein Barr virus (EBV).

Methods for constructing and using viral vectors are known in the art (see, e.g., Miller and Rosman, BioTechniques 1992, 7:980-990). In accordance with the present invention there may be employed conventional molecular biology, microbiology, and recombinant DNA techniques within the skill of the art. Such techniques are well-known and are explained fully in the literature. See, e.g., Sambrook, Fritsch and Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors) and Origene (Rockville, Md.).

In certain embodiments, the viral vectors of the invention are replication defective, that is, they are unable to replicate autonomously in the target cell. Preferably, the replication defective virus is a minimal virus, i.e., it retains only the sequences of its genome which are necessary for target cell recognition and encapsidating the viral genome. Replication defective virus is not infective after introduction into a cell. Use of replication defective viral vectors allows for administration to cells in a specific, localized area, without concern that the vector can infect other cells. Thus, a specific tissue can be specifically targeted. Examples of particular vectors include, but are not limited to, defective herpes virus vectors (see, e.g., Kaplitt et al., Molec. Cell. Neurosci. 1991, 2:320-330; Patent Publication RD 371005 A; PCT Publications No. WO 94/21807 and WO 92/05263), defective adenovirus vectors (see, e.g., Stratford-Perricaudet et al., J. Clin. Invest. 1992, 90:626-630; La Salle et al., Science 1993, 259:988-990; PCT Publications No. WO 94/26914, WO 95/02697, WO 94/28938, WO 94/28152, WO 94/12649, WO 95/02697, and WO 96/22378), and defective adeno-associated virus vectors (Samulski et al., J. Virol. 1987, 61:3096-3101; Samulski et al., J. Virol. 1989, 63:3822-3828; Lebkowski et al., Mol. Cell. Biol. 1988, 8:3988-3996; PCT Publications No. WO 91/18088 and WO 93/09239; U.S. Pat. Nos. 4,797,368 and 5,139,941; European Publication No. EP 488 528).

Adeno-Associated Virus-Based Vectors. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see PCT Publications No. WO 91/18088 and WO 93/09239; U.S. Pat. Nos. 4,797, 368 and 5,139,941; EP Publication No. 488 528). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (e.g., an adenovirus). The AAV recombinants which are produced are then purified by standard techniques.

Adenovirus-Based Vectors. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see PCT Publication No. WO94/26914). Those adenoviruses of animal origin which can be used within the scope of the present invention include adenoviruses of canine, bovine, murine (e.g., Mav1 [Beard et al., Virology, 1990, 75:81]), ovine, porcine, avian, and simian (e.g., SAV) origin. Preferably, the adenovirus of animal origin is a canine adenovirus, more preferably a CAV2 adenovirus (e.g., Manhattan or A26/61 strain [ATCC Accession No. VR-800]). Various replication defective adenovirus and minimum adenovirus vectors have been described (PCT Publications No. WO94/26914, WO95/02697, WO94/28938, WO94/28152, WO94/12649, WO95/02697, WO96/22378). The replication defective recombinant adenoviruses according to the invention can be prepared by any technique known to the person skilled in the art (Levrero et al., Gene, 1991, 101:195; EP Publication No. 185 573; Graham, EMBO J., 1984, 3:2917; Graham et al., J. Gen. Virol., 1977, 36:59). Recombinant adenoviruses are recovered and purified using standard molecular biological techniques, which are well known to one of ordinary skill in the art.

Retroviral Vectors. In another embodiment, the invention provides retroviral vectors, e.g., as described in Mann et al., Cell 1983, 33:153; U.S. Pat. Nos. 4,650,764, 4,980,289, 5,124,263, and 5,399,346; Markowitz et al., J. Virol. 1988, 62:1120; EP Publications No. 453 242 and 178 220; Bernstein et al. Genet. Eng. 1985, 7:235; McCormick, BioTechnology 1985, 3:689; and Kuo et al., 1993, Blood, 82:845. The retroviruses are integrating viruses which infect dividing cells. The retrovirus genome includes two LTRs, an encapsidation sequence and three coding regions (gag, pol and env). Replication defective non-infectious retroviral vectors are manipulated to destroy the viral packaging signal, but retain the structural genes required to package the co-introduced virus engineered to contain the heterologous gene and the packaging signals. Thus, in recombinant replication defective retroviral vectors, the gag, pol and env genes are generally deleted, in whole or in part, and replaced with a heterologous nucleic acid sequence of interest. These vectors can be constructed from different types of retroviruses, such as HIV (human immuno-deficiency virus), MoMuLV (murine Moloney leukaemia virus), MSV (murine Moloney sarcoma virus), HaSV (Harvey sarcoma virus), SNV (spleen necrosis virus), RSV (Rous sarcoma virus), and Friend virus. Suitable packaging cell lines have been described in the prior art, in particular, the cell line PA317 (U.S. Pat. No. 4,861,719); the PsiCRIP cell line (PCT Publication No. WO 90/02806) and the GP+envAm-12 cell line (PCT Publication No. WO 89/07150). In addition, recombinant retroviral vectors can contain modifications within the LTRs for suppressing transcriptional activity as well as extensive encapsidation sequences which may include a part of the gag gene (Bender et al., J. Virol. 1987, 61:1639). Recombinant retroviral vectors are purified by standard techniques known to those having ordinary skill in the art.

Retrovirus vectors can also be introduced by DNA viruses, which permits one cycle of retroviral replication and amplifies transfection efficiency (see PCT Publications No. WO 95/22617, WO 95/26411, WO 96/39036, WO 97/19182).

In a specific embodiment of the invention, lentiviral vectors can be used as agents for the direct delivery and sustained expression of a transgene in several tissue types, including brain, retina, muscle, liver, and blood. This subtype of retroviral vectors can efficiently transduce dividing and nondividing cells in these tissues, and maintain long-term expression of the gene of interest (for a review, see, Naldini, Curr. Opin. Biotechnol. 1998, 9:457-63; Zufferey, et al., J. Virol. 1998, 72:9873-80). Lentiviral packaging cell lines are available and known generally in the art (see, e.g., Kafri, et al., J. Virol., 1999, 73: 576-584).

Non-Viral Vectors. In another embodiment, the invention provides non-viral vectors that can be introduced in vivo, provided that these vectors contain a targeting peptide, protein, antibody, etc. that specifically binds HALR. For example, compositions of synthetic cationic lipids, which can be used to prepare liposomes for in vivo transfection of a vector carrying an anti-tumor therapeutic gene, are described in Feigner et. al., Proc. Natl. Acad. Sci. USA 1987, 84:7413-7417; Feigner and Ringold, Science 1989, 337:387-388; Mackey, et al., Proc. Natl. Acad. Sci. USA 1988, 85:8027-8031; and Ulmer et al, Science 1993, 259:1745-1748. Useful lipid compounds and compositions for transfer of nucleic acids are described, e.g., in PCT Publications No. WO 95/18863 and WO96/17823, and in U.S. Pat. No. 5,459,127. Targeting peptides, e.g., laminin or HALR-binding laminin peptides, and proteins such as anti-HALR antibodies, or non-peptide molecules can be coupled to liposomes covalently (e.g., by conjugation of the peptide to a phospholipid or cholesterol; see also Mackey et al., supra) or non-covaientiy (e.g., by insertion via a membrane binding domain or moiety into the bilayer membrane).

Alphaviruses are well known in the art, and include without limitation Equine Encephalitis viruses, Semliki Forest virus and related species, Sindbis virus, and recombinant or ungrouped species (see Strauss and Strauss, Microbiol. Rev. 1994, 58:491-562, Table 1, p. 493).

As used herein the term "replication deficient virus" has its ordinary meaning, i.e., a virus that is propagation incompetent as a result of modifications to its genome. Thus, once such recombinant virus infects a cell, the only course it can follow is to express any viral and heterologous protein contained in its genome. In a specific embodiment, the replication defective vectors of the invention may contain genes encoding nonstructural proteins, and are self-sufficient for RNA transcription and gene expression. However, these vectors lack genes encoding structural proteins, so that a helper genome is needed to allow them to be packaged into infectious particles. In addition to providing therapeutically safe vectors, the removal of the structural proteins increases the capacity of these vectors to incorporate more than 6 kb of heterologous sequences. In another embodiment, propagation incompetence of the adenovirus vectors of the invention is achieved indirectly, e.g., by removing the packaging signal which allows the structural proteins to be packaged in virions being released from the packaging cell line. As discussed above, viral vectors used to transfect cells and express Nox1 or Rac1 inhibitors may be used, and in a specific embodiment, the viral vectors involve a replication deficient virus.

Other Delivery Vehicles

Many nonviral techniques for the delivery of a nucleic acid sequence into a cell can be used, including direct naked DNA uptake (e.g., Wolff et al., Science 247: 1465-1468, 1990), receptor-mediated DNA uptake, e.g., using DNA coupled to asialoorosomucoid which is taken up by the asialoglycoprotein receptor in the liver (Wu and Wu, J. Biol. Chem. 262: 4429-4432, 1987; Wu et al., J. Biol. Chem. 266: 14338-14342, 1991), and liposome-mediated delivery (e.g., Kaneda et al., Expt. Cell Res. 173: 56-69, 1987; Kaneda et al., Science 243: 375-378, 1989; Zhu et al., Science 261: 209-211, 1993). Many of these physical methods can be combined with one another and with viral techniques; enhancement of receptor-mediated DNA uptake can be effected, for example, by combining its use with adenovirus (Curie) et al., Proc. Natl. Acad. Sci. USA 88: 8850-8854, 1991; Cristiano et al., Proc. Natl. Acad. Sci. USA 90: 2122-2126, 1993). Other examples include stem cells such as mesenchymal stem cells, hematopoietic stem cells, cardiac stem cells or neural stem cells, embryonic stem cells that have been engineered to express a sequence of interest.

Pharmaceutical Compositions

Pharmaceutical compositions of the disclosure can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

In addition to the active ingredients, these pharmaceutical compositions can contain suitable pharmaceutically acceptable carriers comprising excipients and auxiliaries which facilitate processing of the active compounds into preparations which can be used pharmaceutically.

Pharmaceutical compositions comprising a NOI compound of the present invention in free form or in a pharmaceutically acceptable salt form in association with at least one pharmaceutically acceptable carrier or diluent may be manufactured in a conventional manner by mixing, granulating or coating methods. For example, oral compositions may be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragacanth, methylcellulose, sodium carboxymethylcellulose and/or polyvinylpyrrolidone; and if desired, d) disintegrants, e.g., starches, agar, alginic acid or its sodium salt, or effervescent mixtures; and/or e) absorbents, colorants, flavors and sweeteners. Injectable compositions may be aqueous isotonic solutions or suspensions, and suppositories may be prepared from fatty emulsions or suspensions.

Further, the compounds (e.g. protein or delivery vehicle) for use in the method of the invention can be formulated in a sustained release preparation. For example, the compounds can be formulated with a suitable polymer or hydrophobic material which provides sustained and/or controlled release properties to the active agent compound. As such, the compounds for use the method of the invention can be administered in the form of microparticles for example, by injection or in the form of wafers or discs by implantation.

In additional embodiments, the composition comprises sRNA or miRNA specific for Nox1 or Rac1, an antisense nucleotide specific for Nox1 or Rac1, and/or shRNA specific for Nox1 or Rac1 or a delivery vehicle expressing the preceding NOI compounds. In an alternative embodiment, the composition comprises an antibody specific to Nox1 or Rac1.

In another embodiment, administering a therapeutically effective amount of a composition includes a composition comprising: a composition that inhibits the expression or action of Nox1 or Rac1, and a pharmaceutically acceptable excipient.

In further embodiments, the composition includes a Nox1 or Rac1 siRNA, an Nox1 or Rac1 shRNA, an antibody specific to Nox1 or Rac 1, and/or an antisense nucleotide specific for Nox1 or Rac1, or delivery vehicles designed for provision of the same.

Many of the embodiments of the subject invention make reference to particular methods of inhibiting expression. The subject invention is not to be limited to any of the particular methods described. One such method includes siRNA (small interfering/short interfering/silencing RNA). SiRNA most often is involved in the RNA interference pathway where it interferes with the expression of a specific gene. In addition to its role in the RNA interference pathway, siRNA also act in RNA interference-related pathways, e.g., as an antiviral mechanism or in shaping the chromatin structure of a genome.

Another method by which to inhibit expression and to inhibit the expression of Nox1 or Rac1 in particular is shRNA. ShRNA (short hairpin or small hairpin RNA) refers to a sequence of RNA that makes a tight hairpin turn and is used to silence gene expression via RNA interference. It uses a vector introduced into cells and a U6 or H1 promoter to ensure that the shRNA is always expressed. The shRNA hairpin structure is cleaved by cellular machinery into siRNA which is then bound to the RNA-induced silencing complex. This complex binds to and cleaves mRNAs which match the siRNA that is bound to it.

Nox1 or Rac1 can also be blocked by subjecting procured cells to an antibody specific to Nox1 or Rac1. An antisense nucleotide may also be used to block or inhibit expression, in particular, the expression of Nox1 or Rac1. Expression may also be inhibited with the use of a morpholino oligomer or phosphorodiamidate morpholino oligomer (PMO). PMOs are an antisense technology used to block access of other molecules to specific sequences within nucleic acid. PMOs are often used as a research tool for reverse genetics, and function by knocking down gene function. This is achieved by preventing cells from making a targeted protein or by modifying splicing of pre-m RNA.

Example 1

Increasing evidence has suggested that the family of NADPH oxidases (NOX), the enzyme complex that transports electrons across the plasma membrane and generates superoxide, plays a major role in generating ROS in cells (Bedard et al. 2007). NOX was first discovered in neutrophils (Rossi et al. 1964), and seven homologues including NOX1, NOX2, NOX3, NOX4, NOX5, DUOX1, and DUOX2 have been identified in various tissues (Cheng et al. 2001, De Deken et al. 2000, Edens et al. 2001, Suh et al. 1999). ROS at moderate concentrations are necessary for biological processes such as development, memory, neuronal signaling, and cardiovascular homeostasis. However, ROS at higher concentrations in cells have deleterious effects on cellular homeodynamics that include damage to cellular components, such as DNA in both nucleus and mitochondria. Nox is a dedicated superoxide generating enzyme complex and probably a candidate for the production of high concentrations of ROS. Nox homologues are found in the CNS (Sorce et al. 2009), and are linked to pathologic conditions of the same Behrens et al. 2007, Marden et al. 2007, Zekry et al. 2003). Nox1 is the inducible enzyme in the family and Rac1 is an essential subunit for the activation of Nox1.

It has been previously shown that Nox1 expression is increased in dopaminergic neurons in the SN of mice in response to an environmental toxin, paraquat, and that it was responsible for neurodegeneration (Cristovao et al. 2009). Since paraquat induces selective degeneration of SN dopaminergic neurons, it is used to generate a rat model of PD, accumulation of Nox1 in SN dopaminergic neurons of paraquat-treated rats may imply that it happens in the brain of idiopathic PD patients. Lines of evidence suggest that there is cross talk between mitochondria and transcriptional activation of Nox1 (Daiber 2010, Katsuyama et al. 2005, Lee et al. 2006), and a role of mitochondria in neurodegeneration has to be considered along with Nox1 expression in neurons. Of particular interest, the finding that Nox isoforms localize to specific subcellular organelles, including mitochondria and the nucleus (Chamulitrat et al. 2003, Desouki et al. 2005, Kuroda et al. 2005), may cause ROS accumulation and damage to their contents such as DNA.

Results

The NADPH oxidase is a multi-subunit enzyme that consists of the catalytic subunits (Nox isoforms) together with the regulatory subunits including p22phox, p47phox, p40phox, p67phox, Nox organizer 1 (Noxo1), Nox activator 1 (Noxa1), and small GTPase Rac1. In order to test whether dopaminergic (DA) cells are equipped with the NOX components, N27, a well-established rat DA cell line was examined (Prasad et al. 1994). The mRNAs encoding each Nox isoform and regulatory subunits were detected using RT-PCR. Since transcriptional induction of Nox1 and Nox4 has already been reported in several tissues under a variety of stimuli, transcripts were determined in both nontreated and 6-hydroxydopamine (6-OHDA), a DA neurodegenerative compound, treated DA cells. ROS generation as induced by 6-OHDA (100 µM) and subsequent cell death was observed. All Nox isoforms (Nox1, Nox2, Nox4, Duox1 and Duox2) except Nox3 and Nox5 were detected (FIG. 1A). While other variants were expressed constitutively, Nox1 was robustly induced by 100 µM 6-OHDA treatment for 6 h (FIG. 1A). Mitochondria, which have long been considered as a major source of ROS, play a key role in Nox1-mediated superoxide generation (Desouki et al. 2005). Mitochondrial respiratory complex inhibitors which increased mitochondrial ROS also induced Nox1 in N27 cells, suggesting a role of mitochondrial ROS in Nox1 induction. Cytoplasmic regulatory subunits including p47phox, Noxa1, and Noxo1 were constitutively expressed in DA cells as well (FIG. 1A). Noxa1 and Noxo1 are homologues of p67phox and p47phox, respectively. They are involved in Nox1-mediated superoxide generation (Banfi et al. 2003, Geiszt et al. 2003). Treatment with 6-OHDA induced Nox1 expression in a dose-dependent manner was shown by the immunoblot analysis (FIG. 1B). The activation of a small GTPase Rac1 is indispensable for Nox1 and Nox2 activation (Bokoch 2002). GTP-bound active Rac1 was measured in DA cells treated with 6-OHDA for various duration from 1 h to 6 h. Rac1 activation was observed at 6 h post 6-OHDA administration and Nox1 was co-precipitated with active Rac1 (FIG. 1C).

The NADPH Oxidase System Plays a Pivotal Role in 6-OHDA-Mediated ROS Generation

Figure 2:
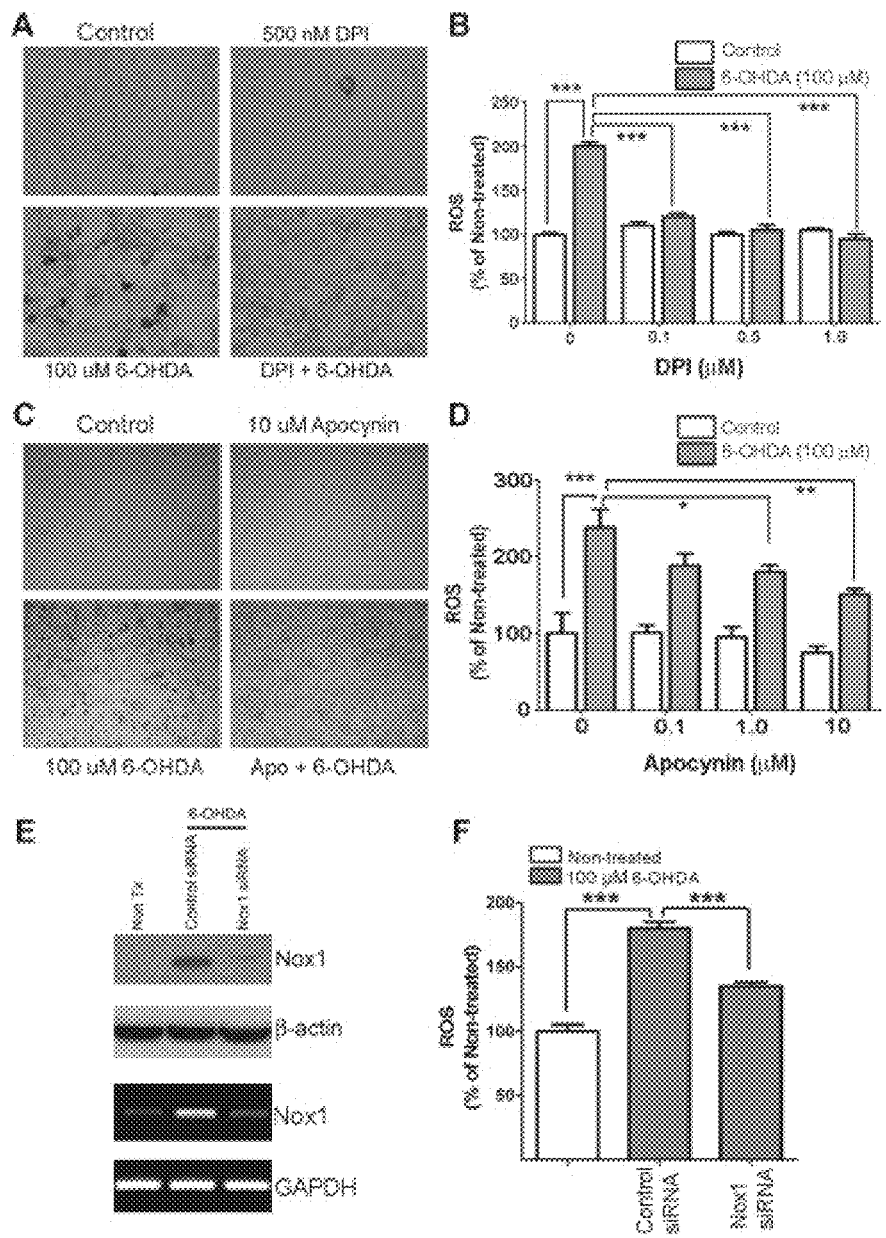
FIG. 2. NADPH oxidase is responsible for 6-OHDA-mediated ROS generation in dopaminergic cells. (A and B) ROS generation was measured using the NBT staining in N27 dopaminergic cells treated with post 6-OHDA (100 lM) for 6 h. DPI significantly reduced 6-OHDA-mediated ROS generation. Representative photomicrograph of the blue formazan staining (A) and spectrophotometric quantitation of formazan showing ROS levels in various DPI concentrations under 6-OHDA treatment (B). (C and D) Apocynin reduced ROS generation as determined the NBT assay at 6 h post 6-OHDA (100 lM). Representative photomicrograph of the blue formazan staining (C) and spectrophotometric quantitation of formazan showing ROS levels in various apocynin concentrations under 6-OHDA treatment (D). Results are presented as the mean+SEM; n=6. The whole experiment has been repeated four times with similar results. *p<0.05; p<0.01; *p<0.001. (E and F) RNAi mediated Nox1 knockdown also significantly reduced 6-OHDA-induced ROS generation. (E) RNAi-mediated Nox1 knockdown efficiency was verified using both immunoblot analysis (upper two panels) and RT-PCR (lower two panels) in N27 cells transiently transfected with rat Nox1 siRNA or control siRNA for 36 h, followed by 6-OHDA exposure for 6 h. b-Actin and GAPDH were visualized as internal controls for immunoblot and RT-PCR, respectively. (F) ROS level was measured using the NBT assay; spectrophotometric quantitation of formazan between groups. Results are presented as the mean+SEM. n=6. The whole experiment has been repeated four times with similar results. ***p<0.001.

To evaluate whether NADPH oxidase system is responsible for 6-OHDA-induced superoxide generation, two widely used chemical inhibitors, diphenyleneiodonium (DPI) and apocynin were tested. N27 cells were pre-treated with various concentrations of DPI (0.1, 0.5, and 1.0 µM) for 30 min and then 6-OHDA (100 µM) was added. Superoxide was measured using the nitroblue tetrazolium (NBT) assay at 6 h post 6-OHDA. DPI significantly reduced 6-OHDA-mediated ROS generation at concentration as low as 0.1 µM (FIGS. 2A and 2B). Due to the nonspecific inhibitory action of DPI on other flavin-dependent enzymes, apocynin, a potent intracellular inhibitor of the assembly of NADPH oxidase, was tested (Stolk et al. 1994). Pre-treatment of DA cells for 30 min with various concentrations of apocynin (0.1, 1.0, 10, 100 µM) also significantly diminished ROS production by 6-OHDA (FIGS. 2C and 2D). To selectively inhibit Nox1, Nox1 knockdown was achieved by RNAi. Nox1 knockdown efficiency of siRNA nucleotide sequence was assessed by both RT-PCR and immunoblotting at 36 h post transfection (FIG. 2E). Transfection efficiency of siRNA nucleotide sequence into N27 cells was tested using fluorescent-tagged siRNA, showing about 37% fluorescence positive cells after 36 h post transfection. In parallel with the transfection rate, 6-OHDA-mediated ROS generation was decreased (FIG. 2F).

Expression of Nox1 in Nigrostriatal DA Neurons of PD Animal Model

Figure 3:
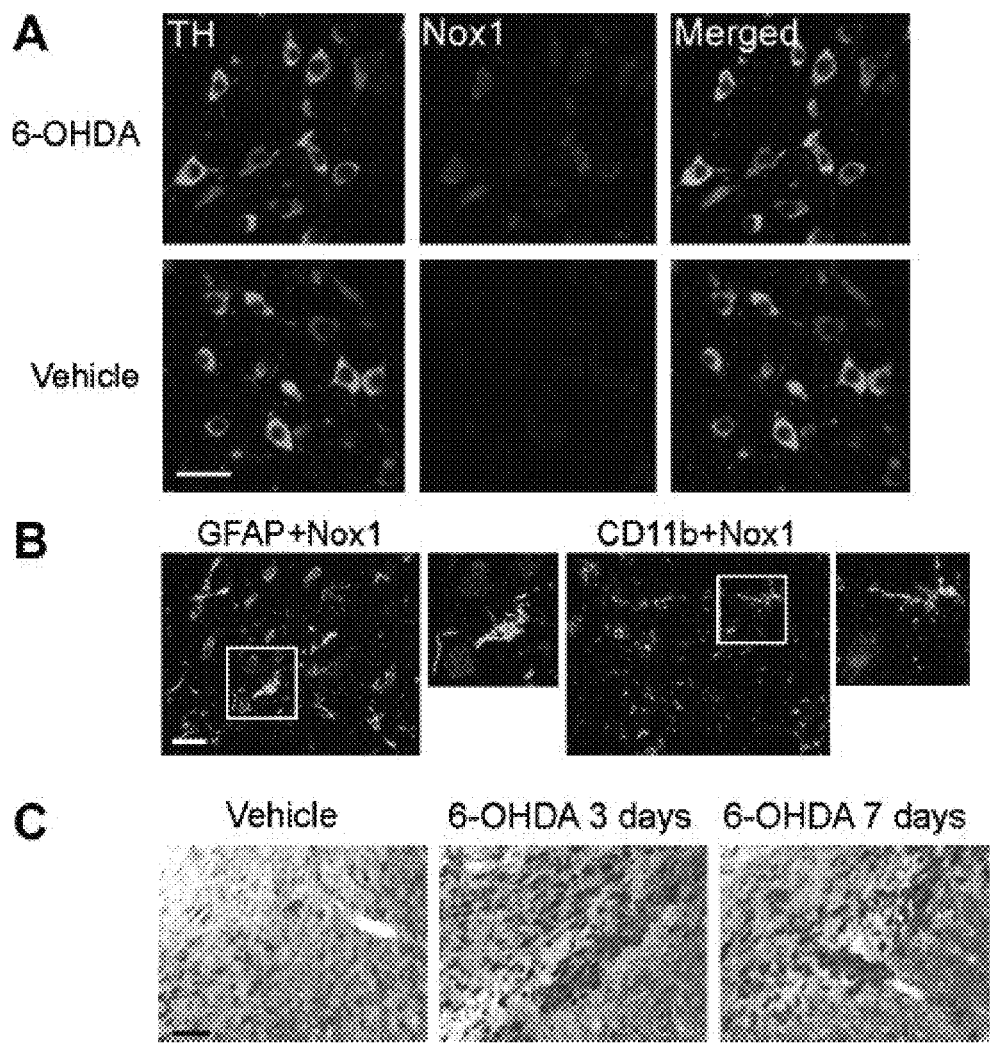
FIG. 3. Striatal administration of 6-OHDA robustly increased Nox1 expression in dopaminergic neurons in the SN. (A) Nox1 expression was increased in the rat SNDA neurons after 6-OHDA administration. TH (green) and Nox1 (red) were visualized in the rat SN at 3 days post-striatal injection of 6-OHDA (upper panels) or vehicle (lower panels). Nox1 expression in TH+DA neurons is demonstrated as yellow staining after merging green (TH) and red (Nox1) images. Scale bars=50 lm. (B) Nox1 (red) expression was observed neither in astrocytes nor in microglia. GFAP (green) and CD11b (green) were stained as markers for astrocytes and microglia, respectively. Boxed area is enlarged in the right panel of each staining. Scale bars=30 lm. (C) Increased Nox1 mRNA level in the SN was detected by nonradioactive in situ hybridization at 3 days and 7 days post 6-OHDA administration. Scale bar=150 lm.
Figure 4:
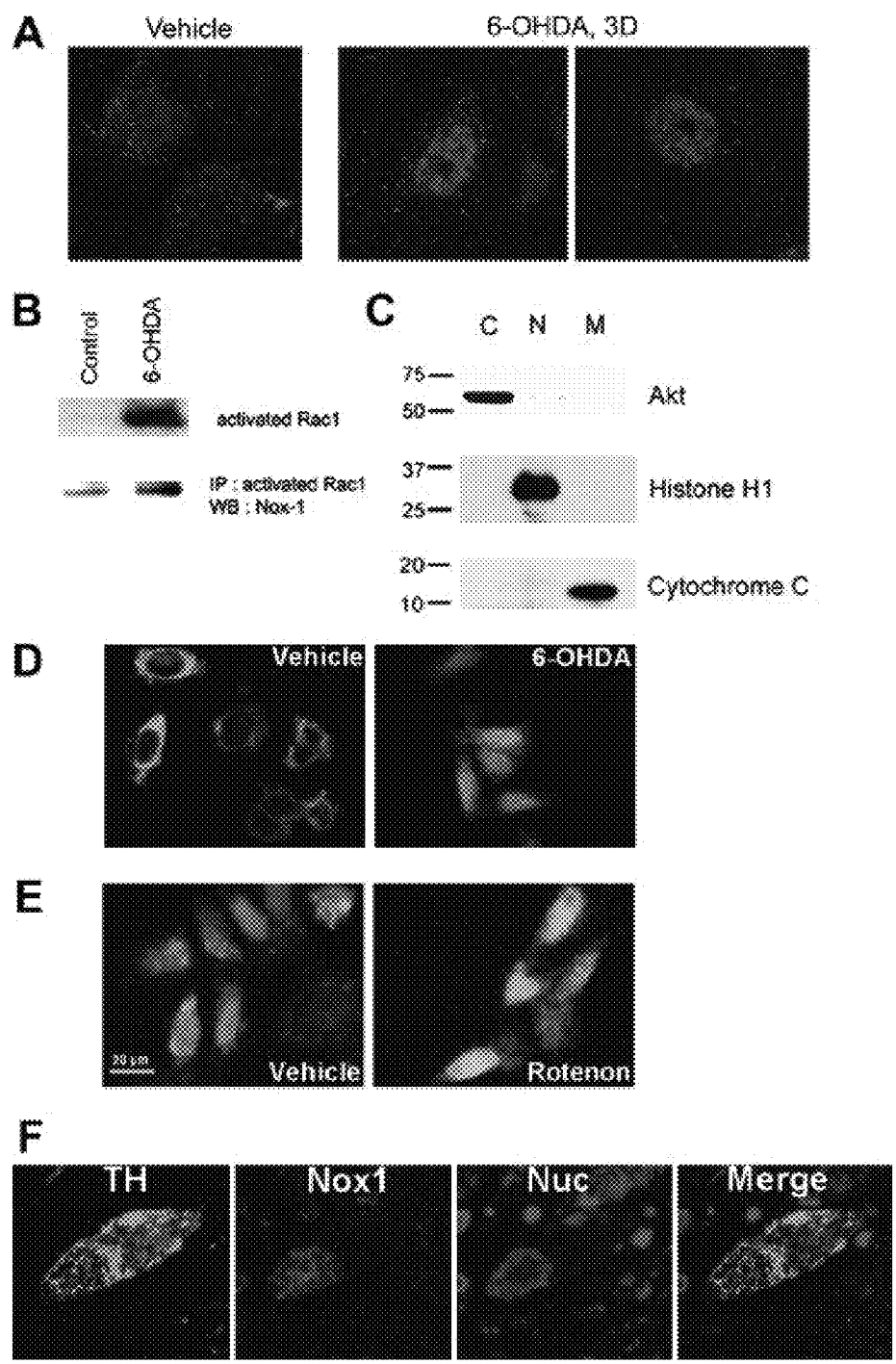
FIG. 4. Nuclear localization of Nox1. (A) Nox1 was visualized in the SN of rats 3 days after treatment with vehicle or 6-OHDA. (B) The nuclear fraction was prepared from N27 cells treated with 6-OHDA (50 lM) overnight. First, GTP bound Rac1 was determined using an active Rac1 pull-down assay (upper panel). Next, Nox1 was detected in the same blot (lower blot). (C) The purity of subcellular fractions was assessed using specific antibodies against Akt, histone H1, and cytochrome C for the cytoplasm (C), nucleus (N), and mitochondria (M), respectively. (D) N27 cells expressing Nox1-EGFP were treated with 6-OHDA (50 lM) for 6 h, and then subcellular localization of Nox1 was investigated by confocal icroscopy. (E) N27 cells expressing Nox1-EGFP were treated with rotenone (5 lM) for 18 h, and then Nox1 nuclear localization was investigated. Nucleus was visualized with DAPI. (F) The SN area of human postmortem PD brain tissue was stained with TH (green), Nox1 (red), and TOTO (blue, nuclear). Nuclear localization of Nox1 was analyzed by confocal microscopy.

The observation that Nox1 was induced by a variety of oxidative stimuli in vitro led one to test Nox1 expression in the rat substantia nigra DA (SNDA) neurons administered with 6-OHDA. In comparison to vehicle treatment, a significant increase of Nox1 expression was observed in the substantia nigra (SN) after 3 days of 6-OHDA striatal injection (FIG. 3A). Neurons immunostained for Nox1 (red) displayed coexpression of tyrosine hydroxylase (TH) (green) in the SN, indicating DA neuron-specific expression of Nox1 (FIG. 3A). Neither astrocytes nor microglia expressed Nox1, as verified by co-immunostaining of Nox1 with GFAP (astrocytes) or CD11b (microglia) (FIG. 3B). Increased Nox1 transcript was found in the SN as shown by in situ hybridization (FIG. 3C). Increased Nox1 expression in the SNDA neurons was also observed in mice treated with 1-methyl-4-phenyl-1,2,3,6-tetrahydropyridine (MPTP), a specific DA neurotoxin. Confocal microscopic analysis showed that constitutively expressed low-level Nox1 in the nucleus of DA neurons was significantly increased by 6-OHDA administration. As early as 3 days post 6-OHDA injection, Nox1 expression was increased in the nucleus and in the cytoplasm of DA neurons (FIG. 4A). About 75% of TH-positive neurons also showed Nox1 nuclear staining after 6-OHDA administration. Nuclear expression of the Nox1/Rac1 complex was further analyzed in N27 cells after treatment with 6-OHDA. First, activated Rac1 was detected by immunoprecipitation of nuclear extracts of N27 cells after a 24 h treatment with 6-OHDA. Increased Nox1 was also observed in the same blot, suggesting that Nox1 in the nucleus forms an active complex with GTP-bound Rac1 (FIGS. 4B and 4C). Next, it was established that N27 cells stably expressing Nox1 tagged with EGFP at the C-terminus. Six h 6-OHDA treatment resulted in the translocation of Nox1-EGFP into the nucleus (FIG. 4D). To examine whether nuclear translocation of Nox1 in dopaminergic cells is observed under different conditions that cause dopaminergic neuronal death, mitochondrial respiratory complex inhibitor, rotenone, was tested. Rotenone also led to nuclear localization of Nox1 (FIG. 4E). The presence of Nox1 in the nucleus of TH-positive DA neurons in the SN of postmortem brains of PD patients was observed in four PD subjects and none of controls (FIG. 4E), further supporting our hypothesis that Nox1 plays a role in degeneration of DA neurons in PD. Our results demonstrate for the first time that an active Nox1/Rac1 complex is formed in the nucleus of oxidatively stressed DA neurons.

Nuclear Nox1/Rac1 Caused DNA Oxidative Damage in DA Cells

Figure 5:
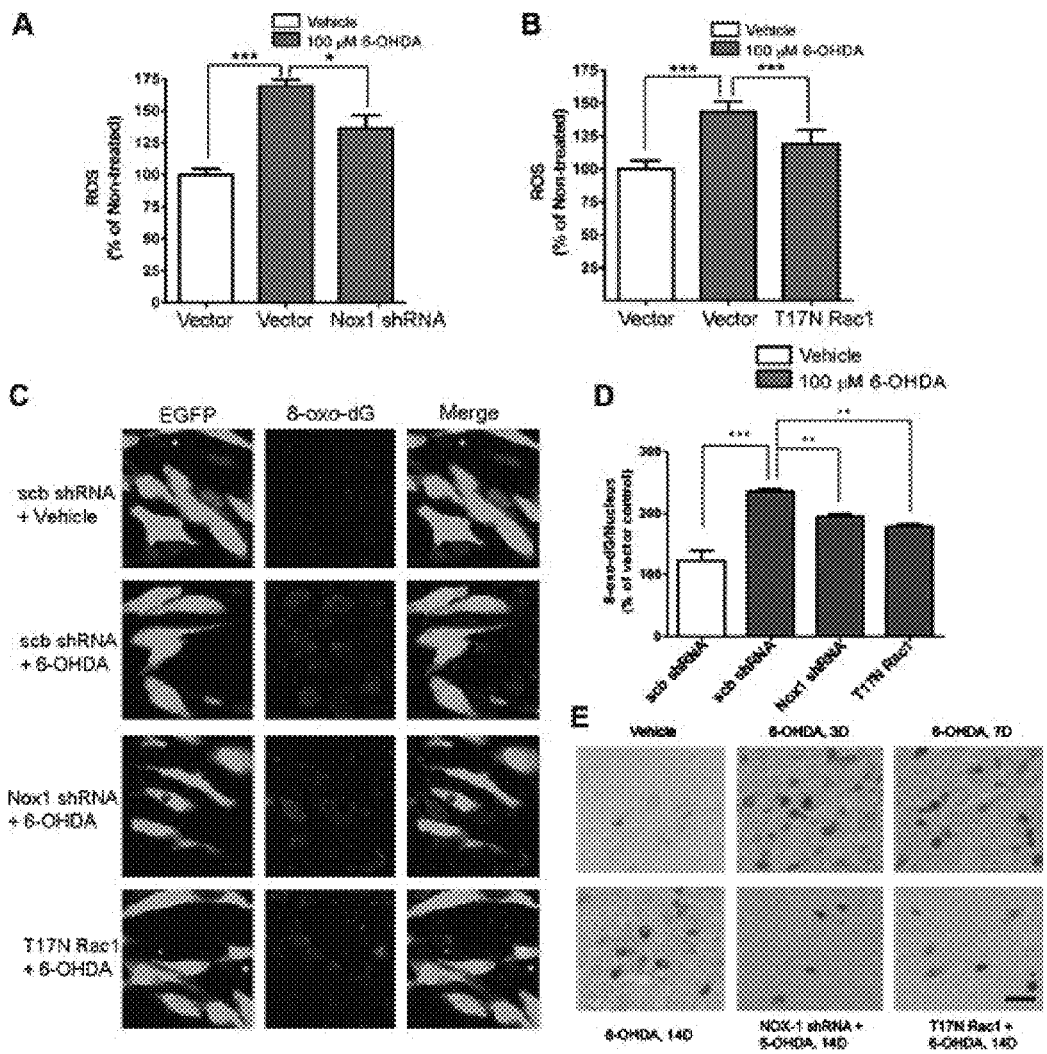
FIG. 5. Nox1 knockdown or Rac1 inhibition decreased 6-OHDA-induced ROS generation and DNA oxidative damage in dopaminergic cells. (A and B) N27 cells were incubated with Nox1 shRNA (A) or T17N Rac1/AAV particles (B) for 36 h and then exposed to 6-OHDA (100 lM) for 6 h. ROS levels were determined by the NBT assay and blue formazan was quantified. Results are presented as the mean+ SEM; n=6. The whole experiment was repeated 4 times with similar results. *p<0.05, *p<0.001. (C) N27 cells were incubated with either scramble shRNA/AAV, Nox1 shRNA/ AAV, or T17N Rac1/AAV particles for 36 h and then exposed to 6-OHDA (100 lM) for 6 h. Oxidative DNA damage was detected by 8-oxo-dG immunostaining (red). Cells expressing GFP (green) represent AAV-transduced cells. scb shRNA, scramble shRNA/AAV. Representative images of four repeated experiments with similar results. (D) Under the same culture conditions described above, nuclear 8-oxo-dG-positive cells were counted. p<0.01, ***p<0.001. (E) 4 weeks after Nox1 shRNA or T17N Rac1/AAV injection into the rat SN, 6-OHDA was administered into the striatum. 14 days after 6-OHDA injection, 8-oxo-dG was detected in the SN (Nox1 shRNA+6-OHDA 14D or T17N Rac1+6-OHDA 14D). Vehicle, vehicle for 14 days; 6-OHDA 3D, 7D, 14D, 3 days, 7 days, or 14 days after 6-OHDA administration, respectively. Scale bar=30 lm.

To substantiate that nuclear Nox1/Rac1 complex produces superoxide, it was investigated whether selective inhibition of the Nox1/Rac1 complex attenuates ROS production. Adeno-associated virus serotype 2 (AAV2) expression cassettes with either Nox1 shRNA or a T17N dominant negative Rac1 variant were used to knockdown Nox1 or inhibit Rac1, respectively. These vectors separately expressed Green Fluorescent Protein (GFP) as a marker for transduction efficiency. Nox1 knockdown by Nox1 shRNA (FIG. 5A) or Rac1 inhibition by T17NRac1 (FIG. 5B) significantly reduced 6-OHDA-mediated ROS generation in N27 cells. The increased levels of active Nox1/Rac1 complex (FIG. 4B) in the nucleus, and increased ROS (FIGS. 5A and 5B) of DA cells in the presence of 6-OHDA, led one to investigate whether oxidative DNA damage occurs in the nucleus. In fact, 6-OHDA treatment increased DNA oxidative damage as determined by increased 8-oxo-dG immunoreactivity in the nucleus of both N27 cells and DA neurons in the rat SN (FIGS. 5C-5E). Increased 8-oxo-dG immunoreactivity in the presence of 6-OHDA was significantly reduced by pre-incubation of N27 cells with either Nox1 shRNA or T17NRac1/AAV2 viral particles. However, scramble shRNA failed to reduce 8-oxo-dG staining in the nucleus (FIG. 5C). As early as 3 days after striatal injection of 6-OHDA, 8-oxo-dG staining was increased in the SN (FIG. 5E). In vivo targeting of Rac1 or Nox1 was achieved by stereotaxic delivery of AAV2 particles harboring either T17NRac1 or Nox1 shRNA into the rat SN. 6-OHDA was injected at 4 weeks post AAV2 injection which pointed out that, around 70% of TH+SNDA neurons were transduced with AAV2 particles as indicated by GFP. Immunostaining with 8-oxo-dG in the SN was reduced by either Nox1 knockdown or Rac1 inhibition (FIG. 5E), suggesting that Nox1/Rac1-derived superoxide generation is responsible for 6-OHDA-induced oxidative DNA damage. The fact that increased Nox1 expression is observed in the nucleus as early as 3 days post 6-OHDA (FIG. 4A) and increased nuclear 8-oxo-dG immunostaining (FIG. 5D) occurs concurrently, suggests that oxidative DNA damage is caused by Nox1/Rac1 activation. The results also suggest that Nox1-generated superoxide may play a critical role in oxidative damage to genomic DNA, which is frequently observed during both aging and in PD (Nakabeppu et al. 2007).

Inhibition of Rac1 or Nox1 Reduced DA Cell Death Induced by 6-OHDA

Figure 6:
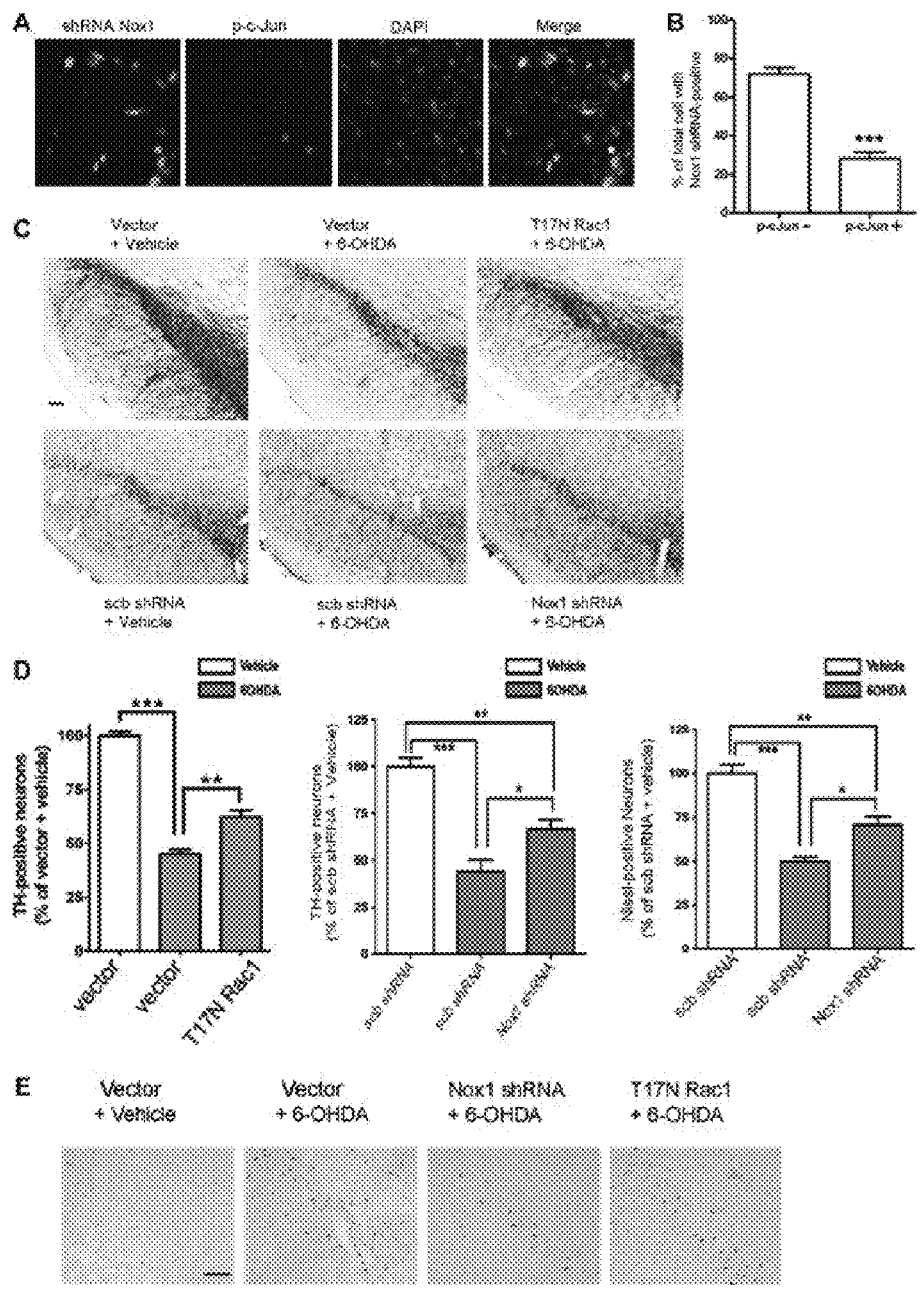
FIG. 6. Decreased DA cell death by Nox1 knockdown or Rac1 inhibition. (A and B) N27 cells were incubated with Nox1 shRNA/AAV particles for 36 h and then exposed to 6-OHDA (100 lM) for 6 h. Cultures were stained with phospho-c-Jun (pc-Jun, red). Cells expressing GFP (green) represent AAV-transduced cells. DAPI staining (blue) was used to visualize nucleus (A). GFP-positive and p-c-Jun-negative cells (p-c-Jun-, green) and GFP-positive and p-c-Jun-positive cells (p-c-Jun+, yellow) cells were counted. Total 726 GFP-positive cells were counted. Data represent three independent experiments with similar results. *p<0.001 (B). (C and D) Representative photomicrographs of TH staining in the rat SN sections. AAV particles containing empty vector, scramble shRNA, Nox1 shRNA, or T17NRac1 were stereotaxically injected into the rat SN. After 4 weeks incubation, vehicle or 6-OHDA were injected into the striatum. Two weeks later, DA neurons in the SN were visualized with TH immunostaining (upper panel) for T17N Rac1. For Nox1 shRNA, the SN was stained both TH and Nissl. Vector, injection of vector/AAV particles into the SN; T17N Rac1, injection of T17NRac1/AAV particles into the SN; scb shRNA, injection of scramble shRNA/AAV into the SN; Nox1 shRNA, injection of Nox1 shRNA/AAV particles into the SN; +vehicle, striatal injection of vehicle 4 weeks after AAV; +6-OHDA, striatal injection of 6-OHDA 4 weeks after AAV. Scale bar=150 lm (C). Stereologic counts of TH-positive neurons in the SN shown as percentage of vector+vehicle or scb shRNA+vehicle (left and middle panel). Nissle-positive neurons in the SN shown as percentage of scb shRNA+vehicle. Results are presented as the mean+SEM. n=6-7. Significance is indicated by *p<0.001 and **p<0.01 (D). (E) p-c-Jun was also detected in the SN by immunohistochemistry. Scale bar=100 lm.

The next series of studies investigated the mechanism by which Nox1/Rac1-mediated DNA damage results in oxidative stress-induced DA neuronal death. c-Jun N-terminal kinase (JNK)-mediated signaling has been implicated as a final common pathway of DA neuronal apoptosis (Silva et al. 2005). Immunostaining of nuclear phospho c-jun (p-c-jun) was used as markers of 6-OHDA-induced apoptosis of DA cells. GFP-positive N27 cells expressing Nox1 shRNA lacked p-c-jun immunostaining (FIGS. 6A and 6B), suggesting that Nox1 knockdown blocked 6-OHDA-mediated apoptosis in N27 cells. In vivo, a 4-week pre-injection with either Nox1 shRNA or T17NRac1/AAV2 viral particles in the SN area, significantly diminished SN DA neuronal loss produced by intrastriatal administration of 6-OHDA ($p<0.01$) as determined by stereologic cell counting of tyrosine hydroxylase (TH)-immunostained DA neurons (FIG. 6C). Nox1 knockdown efficiency in the SN was verified by Western blot analysis. The number of Nissl-stained SNDA neurons also showed a similar protective effect. Direct injection of 6-OHDA into the rat SN resulted in a 90%-95% loss of TH-positive SNDA neurons in 2 weeks. Either Nox1 knockdown or Rac1 inhibition also significantly reduced DA neuronal death elicited by 6-OHDA ($p<0.01$). In similar experiments, the number of p-c-jun positive neurons in the SN of T17N Rac1- or Nox1 shRNA-expressing animals were significantly less than those in nontransduced animals, indicating that inhibition of Nox1/Rac1 activation attenuated 6-OHDA-elicited DA neuronal apoptosis in the SN (FIG. 6D). DA neuron-specific staining of p-c-jun was confirmed by co-immunostaining with TH.

Discussion

We present convincing evidence to support our hypothesis that the ROS produced by the Nox1/Rac1 complex play a pivotal role in the degeneration of nigrostriatal dopaminergic neurons in an animal model of PD. The accumulation of the Nox1 complex, production of ROS, and nuclear DNA damage are all found in the nucleus of degenerating dopaminergic neurons. In addition to these results, nuclear 8-oxo-dG staining precedes other signs of neuronal degeneration. These results strongly indicated that Nox1-mediated oxidative damages may serve as critical upstream processes in neurodegeneration. Oxidative damage to DNA is the central issue in neurodegeneration. It is widely accepted that mitochondrial ROS causes oxidative damage to nuclear DNA; nonetheless, the mechanism underlying nuclear DNA damage is still elusive. Presented in this current study is critical evidence that ROS produced by the Nox1/Rac1 complex that accumulates in the nucleus, damages nuclear DNA which could be responsible for dopaminergic neurodegeneration. The evidences are: a) accumulation of the Nox1/Rac1 complex in the nucleus of both SN dopaminergic neurons in the 6-OHDA-treated rat model and dopaminergic cell cultures in presence of 6-OHDA; b) Nox1 expression in TH-positive neurons in the SN of the postmortem brain of PD patients; c) increased 8-oxo-dG staining in the nucleus, and subsequent attenuation of dopaminergic neurodegeneration either by chemical inhibition of Nox1 through apocynin, or by and genetic interventions targeting Nox1 and Rac1. Thus, our results lead to the new concept that oxidative damage to nuclear DNA occurs through the accumulation of Nox1/Rac1 complex and ROS in the nucleus. This event is deleterious to dopaminergic neurons and to a new direction in the pursuit of an effective therapy for PD.

To selectively target Nox1/Rac1 in SN dopaminergic neurons in vivo, developed was the adeno-associated virus serotype 2 (AAV2)-mediated overexpression or knockdown system. Increasing reports including our recent study (Choi et al. 2011, Van der Perren et al. 2011) have shown that the AAV2-mediated gene transfer provides an effective means of achieving long-term expression of target genes in nondividing cells such as neurons (Bjorklund et al. 2000) and that AAV-mediated shRNA delivery to the CNS for targeted knockdowns of specific genes can also be achieved successfully (Rodriguez-Bebron et al. 2005). Four weeks after an AAV injection into the rat SN, more than 70% of TH-positive neurons were GFP positive, indicating that our AAV system efficiently works in SN DA neurons. AAV2-mediated delivery of Nox1 shRNA or T17N Rac1 constructs similarly led to reduced DNA oxidative damage and a reduction of about 25%-30% in DA neuronal death induced by 6-OHDA.

It is noteworthy to mention here an important role of mitochondria in neurodegeneration along with Nox1 expression. Array of evidences suggest cross talk between mitochondria and transcriptional activation of Nox1 (Desouki et al. 2005, Katsuyama et al. 2005, Lee et al. 2006). In serum-deprived 293 cells, the early accumulation of mitochondrial ROS contributes to the sequential events of Nox1 induction and then the later phase of ROS accumulation followed by cell death (Lee et al. 2006). Studies of mitochondrial gene knockout osteosarcoma cells)($\rho^0$) revealed that the inactivation of mitochondrial genes leads to downregulation of Nox1 and that the transfer of wild-type mitochondrial genes can restore Nox1 expression (Desouki et al. 2005). Our results also confirmed that mitochondrial respiratory chain inhibitors including rotenone, pyridaben, antimycin A, and FCCP, elevated both mRNA and protein levels of Nox1. 6-OHDA directly generates free radicals by auto-oxidation and also serves as a potent inhibitor for the mitochondrial respiratory chain complexes I and IV (Glinka et al. 1997). A recent study indicates that microglial NOX2-derived ROS synergistically contributes to 6-OHDA-induced DA cell death (Rodriguez-Lebron et al. 2005). ROS generated by 6-OHDA or mitochondrial events may also synergistically act on Nox1 induction and Rac1 activation in dopaminergic neurons and then, in turn, increase the ROS level and DA cell death. Establishing cooperative relationship between mitochondrial activity and Nox1 expression can be an important molecular event occurring in the toxin-elicited degeneration of SN dopaminergic neurons in both animal models of PD and the brain of PD patients.

Chronic exposure to ROS and the effects of ROS are devastating to neurons since damaged cells cannot be replaced by intact ones. Oxidative base modifications including damage and repair of DNA in both nuclear and mitochondria play a key role in the selective neuronal loss associated with mammalian aging and neurodegeneration. There are cell-type specific DNA repair systems and also differential DNA repair systems between mitochondria and the nucleus (Nousipikel 2007). For instance, oxidative base lesions in DNA are mainly repaired by base excision repair (BER) and mitochondrial uracil-DNA glycosylase 1 (UNG1) and nuclear uracil-DNA glycosylase 2 (UNG2) which are differentially regulated (Akbari et al. 2007). Further studies on DNA damage and repair in mitochondria and the nucleus are required to elucidate the mechanisms underlying DNA damage-elicited neuronal degeneration in PD.

Dopaminergic neurons in SN are specific targets of environmental toxins that include toxic herbicides, such as paraquat, and it is suggested that human exposure to environmental toxins leads to sporadic neurodegenerative diseases, especially to PD. Earlier, it was demonstrated that Nox1 is accumulated in SN dopaminergic neurons in paraquat-treated mice (Cristovao et al. 2009). This result, together with our current finding of the occurrence of Nox1 in SN dopaminergic neurons of the postmortem brain of PD patients, further strengthens our extended hypothesis that accumulation of Nox1 in SN dopaminergic neurons is a critical cellular event in developing neurodegeneration in PD.

An increasing number of studies has been identifying the specific localization of the members of the NOX family and their role in the CNS (Sorce 2009), and the dysregulation of the NOX system and ROS overproduction contribute to neuronal death and other diseases, such as cardiovascular diseases (Infanger et al. 2006). Most of the NOX studies in neurodegenerative disease have highlighted microglial NOX2-induced ROS production. These studies include the cases of AD (Qin et al. 2006), ALS (Marden et al. 2007), and PD (Wu et al. 2003). Recent evidence indicates that oxidative stress may be caused directly from NOX in the neuron itself. Glutamate toxicity in SH-SY5Y neuroblastoma cells was largely attenuated by the inhibition of NOX activation (Nikolova et al. 2005). ROS generation and apoptosis of N27 DA cells treated with 1-methyl-4-phenylpyridinium (MPP+), active metabolite of MPTP, was also decreased by NOX inhibition (Anantharam et al. 2007). Nox1 is an inducible member of the NOX enzyme family and the Nox1 expression in cells may reflect the requirement of ROS for cellular homeostasis in quiescent states. Transcriptional activation of Nox1 in response to a variety of stimuli has been described in various tissues (Fan et al. 2005, Geiszt et al. 2003, Kawahara et al. 2005). It was also observed that Nox1 expression was significantly increased after exposure to various toxic insults in N27 rat dopaminergic cells. Both Nox1 mRNA and protein increase under oxidative stressed conditions such as 6-OHDA, rotenone, and $H_2O_2$. Nox1 is constitutively expressed at a low level in vivo in SN dopaminergic neurons. In a parallel culture of N27 cells, both mRNA transcript and protein levels of Nox1 are increased mostly in (or exclusively) SN dopaminergic neurons of 6-OHDA-treated rats. Although Nox4 was constitutively expressed in N27 cells, Nox4 transcript in the rat SN dopaminergic neurons in vivo was not detected.

The most interesting finding here is the nuclear localization of Nox1/Rac1 complex and the subsequent oxidative damage to DNA. Distinct subcellular localizations of Nox1 in non-neuronal cells have been reported (Chamulitrat et al., Desoukie et al. 2005, Hilenski et al. 2004). The aforementioned study using osteosarcoma cells showed the presence of Nox1 in mitochondria (Desouki et al. 2005). While Nox1 is found in the cellular periphery in human vascular smooth muscle cells, it is localized to the nucleus in transformed human keratinocytes (Chamulitrat et al. 2003, Hilenski et al.). Recent study demonstrated that Nox4 is localized to the nucleus and responsible for DNA oxidative damage, as well as MCP-1 expression in hemangioendotheliomas (Gordillo et al. 2010). In N27 cells treated with 6-OHDA, the GTP-bound Rac1 and its binding to Nox1 in the nucleus were increased. In the rat SN dopaminergic neurons, Nox1 expression is increased in the nucleus as early as 3 days post 6-OHDA treatments. At this time point, TH-positive dopaminergic neuronal loss was not observed, but nuclear 8-oxo-dG is densely stained, suggesting that oxidative nuclear DNA damage precedes neuronal degeneration. The low-level nuclear expression of Nox1 under unstressed conditions may contribute to redox-responsive gene expression necessary for cellular homeostasis (Bedard 2007). Nox1 does not contain a putative nuclear localization sequence (NLS), suggesting that its nuclear translocation may be dependent on other molecules which form an enzyme complex with Nox1. Rac1 has a NLS in the C-terminus and thus translocates to the nucleus upon activation (Michaelson et al. 2008). Noxo1 gamma was also found in the nucleus (Ueyama et al. 2007). It needs to be clarified whether Rac1 activation is independently responsible for Nox1/Rac1 translocation into the nucleus or its co-localization in the nucleus. The major pathway responsible for removing oxidative DNA damage and restoring the integrity of the genome is base excision repair (BER), and defective BER processing can promote neuronal cell death and neurodegenerative disease (Akbari et al. 2007). This line of study is required for further understanding of the molecular mechanisms underlying neuronal degeneration through nuclear DNA damage in PD. The mechanism underlying nuclear translocation of Nox1 and active Rac1 in DA neurons also requires further investigation.

Materials and Methods

N27 Cell Culture

N27 cells are derived from rat mesencephalon and express tyrosine hydroxylase and dopamine transporter (Prasad et al. 1994). Cells were grown in RPMI 1640 containing 10% FBS, 100 IU/1 penicillin, and 10 g/ml streptomycin at 37° C. with 5% $CO_2$ supply in humidified atmosphere. For experiments, the cells were plated on polystyrene tissue culture dishes at a density of $2 \times 10^4$ cells/well in 96-well culture plates, $1 \times 10^6$ cells/well in 24-well culture plates, $1 \times 10^6$ cells/well in 6-well culture plates, or $2 \times 10^6$ cells/100 mm plate. After 24 h, the cells were fed with fresh medium and treated with 6-OHDA and/or other drugs.

Total RNA Extraction and RT-PCR Analysis

Total RNA was extracted from N27 cells using Trizol reagent (Invitrogen, Carlsbad, Calif.). Reverse transcription was performed for 1 h at 42° C. with 1 μg of total RNA using 20 unit/μl of AMV reverse transcriptase (Roche Applied Science, Indianapolis, Ind.), and oligo-p(dT)$_{15}$ as a primer. The samples were then heated at 99° C. for 5 min to terminate the reaction. The cDNA obtained from 1 μg total RNA was used as a template for PCR amplification. Oligonucleotide primers were designed based on Genebank entries for rat NOX1 (sense, 5'-TGACAGTGATGTATGCAGCAT-3' SEQ ID NO. 1; antisense, 5'-CAGCTTGTTGTGTGCACGCTG-3' SEQ ID NO. 2), rat NOX2 (sense, 5'-ACTCGAAAACTTCT-TGGGTCAG-3' SEQ ID NO. 3; antisense, 5'-TCCTGTGAT-GCCAGCCAACCGAG-3' SEQ ID NO. 4), rat NOX4 (sense, 5'-GCCGGCGGTATGGCGCTGTC-3' SEQ ID NO. 5; antisense, 5'-CCACCATGCAGACACCTGTCAGG-3' SEQ ID NO. 6), rat NOXA1 (sense, 5'-TCTAGGGGATCA-GATACGGGAC-3' SEQ ID NO. 7; antisense, 5'-CCAAG-GAAATCCATGGGCTCCAG-3' SEQ ID NO. 8), rat NOXO1 (sense, 5'-ACCCAGTATCAGCCCATGCTG-3' SEQ ID NO. 9; antisense, 5'-ATGGAGCATCAGGAAGCT-TGG-3' SEQ ID NO. 10), rat p47 (sense, 5'-GTTAAAG-GAGATGTTCCCCATTG-3' SEQ ID NO 11; antisense, 5'-TTATGAATGACCTCGATGGCTTC-3' SEQ ID NO. 12), rat Duox1 (sense, 5'-AGTAGGGGATTGGGGAT-3' SEQ ID NO. 13; antisense, 5'-TCTATAAGTGGCCCCTGGCT-3'SEQ ID NO. 14), rat Duox2 (sense, 5'-GACCTGGATG-GAAATGGCTT-3' SEQ ID NO. 15; antisense, 5'-ACTCGA-CAGGCATTGCTTTG-3' SEQ ID NO. 16) and rat GAPDH (sense, 5'-ATCACCATCTTCCAGGAGCG-3' SEQ ID NO. 17; antisense, 5'-GATGGCATGGACTGTGGTCA-3' SEQ ID NO. 18). PCR mixes contained 10 μl of 2×PCR buffer, 1.25 mM of each dNTP, 10 pmol of each forward and reverse primer, and 2.5 units of Taq polymerase in the final volume of 20 μl. Amplification was performed in 35 cycles at 60° C., 30 sec; 72° C., 1 min; 94° C., 30 sec. After the last cycle, all samples were incubated for an additional 10 min at 72° C. for final extension step. PCR fragments were analyzed on 1.2% agarose gel in 0.5×TAE containing ethidium bromide. Amplification of GAPDH, a relatively invariant internal reference RNA, was performed in parallel, and cDNA amounts were normalized against GAPDH mRNA levels. The primer set specifically recognized only the gene of interest as indicated by amplification of a single band of expected size.

Western Blot Analysis

Cells were washed with ice-cold PBS and lysed on ice in RIPA buffer (1% PBS, 1% NP-40, 0.5% sodium deoxycholate, 0.1% SDS) containing protease inhibitor mixture (AEBSF, aprotinin, bestatin hydrochloride, E-64-[N-(trans-epoxysuccinyl)-L-leucine 4-guanidinobutylamide], leupeptin, pepstatin A) (Sigma, Saint Louis, Mo.). A total of 30 μg of soluble protein per lane was loaded in SDS-PAGE and electrotransferred onto PVDF membrane. Specific protein bands were detected by using specific anti-Nox1 antibody (Santa Cruz Biotechnology, Santa Cruz, Calif.) and Enhanced Chemiluminescence (Pierce, Rockford, Ill.).

Determination of ROS Using NBT Staining

6-OHDA treated cells were incubated for 1 h at 37° C. with a filtered solution of 0.3 mg/ml of NBT in complete medium. The cells were washed once with PBS and fixed with 0.4% paraformaldehyde for light microscopy. To quantify NBT precipitation, cells were washed twice with 70% methanol and fixed for 5 min in 100% methanol. After the wells were allowed to dry in the air, the formazan is solubilized with 120 μl 2M K OH and 140 μl DMSO. The OD was read in an ELISA plate reader at 590 nm.

Rac1 Activation Assay

Total cellular protein (500 μg) obtained from lysed N27 cells was incubated with 20 μl of agarose beads containing p21-binding domain (PBD) of p21-activated protein kinase 1 (PAK1), an effector of activated Rac, for 1 h at 48° C. The beads were collected by centrifugation and washed two times in the lysis buffer, resuspended in sample buffer, and boiled for 5 min. Proteins were resolved by SDS-PAGE using a 10%-20% Tricine gel, transferred electrophoretically and visualized using anti-rat Rac1 antibody, followed by electrochemoluminescence (ECL) detection. For the positive control, the nonhydrolyzable GTP analog GTPgS was used according to the manufacturer's protocol (Cell Biolabs, New York, N.Y.).

Preparation and Transfection of siRNA

Sense and anti-sense oligonucleotides corresponding to the following cDNA sequences of rat Nox1 were used (5'-CCTTTGCTTCCTTCTTGAAATCTAT-3' SEQ ID NO. 19). The double-stranded siRNAs were synthesized chemically and modified into stealth siRNA (Invitrogen, Carlsbad, Calif.) to enhance the stability in vitro. Negative control stealth RNAi with a similar GC content as Nox1 stealth RNAi was used. The sense and anti-sense oligonucleotides were annealed following the manufacturer's protocol to generate double-stranded siRNAs at the final concentration of 20 μM. N27 cells grown to 80% confluence in 6-well culture plates were subjected to transfection by adding 10 μl of Lipofectamin TM 2000 and 8 μl of 20 μM siRNAs (final concentration 40 nM). After 6 h of incubation, the culture medium was changed and cells were maintained for additional 30 h before analysis.

Lactate Dehydrogenase Assay

Degrees of cell death were assessed by activity of LDH released into the culture medium using the cytotoxic assay kit (Promega Bioscience, San Luis Obispo, Calif.). Aliquots (50 μl) of cell culture medium were incubated with 50 μl of LDH substrates for 15~30 min at room temperature. The rate of $NAD^+$ formation was monitored for 5 min at 2-sec intervals at 340 nm using a microplate spectrophotometer (Spectra Max 340 pc; Molecular Devices, Menlo Park, Calif.).

Animals and Stereotaxic Injection of AAV2 Particles and 6-OHDA

The experiments were carried out on rats, in accordance with the NIH Guide for the Care and Use of Laboratory Animals. All procedures were approved by the local Animal Care and Use Committee. Female Sprague Dawley (SD) rats (Charles River; 8-weeks-old at the time of the beginning of AAV expression or 6-OHDA treatment, 2 or 3 per cage) were maintained in a temperature/humidity-controlled environment under a 12 h light/dark cycle with free access to food and water. All rats were respectively allocated into 2 groups, Nox1 shRNA/AAV, T17N Rac1/AAV, and scramble (scb) shRNA/AAV or empty vector/AAV as control groups. Rats were deeply anesthetized (ketamine and xylazine mixture 30 mg/kg, i.p.) and placed in a rat stereotaxic apparatus, a site in the right substantia nigra (SN) [coordinate: anteroposterior (AP), −5.3 mm; mediolateral (ML), +2.0 mm; dorsoventral (DV), −5.8 mm] was selected to inject scb shRNA/AAV (n=8), Nox1 shRNA/AAV (n=16), T17N Rac1/AAV (n=16), and empty vector/AAV (n=28), respectively, according to the grouping. A total of $1 \times 10^{11}$ genome copy/ml rAAV particles encoding shNox1, T17N rac1, scb, or empty vector diluted in 2 μl ice-cold sterilized phosphate buffered saline (PBS) were used in every animal. Four animals of Nox1 shRNA/AAV, T17N Rac1/AAV, or empty vector group were used for the detection of Nox1 shRNA, T17N Rac1, or empty vector expression at 4 weeks following AAV particle injection. Six animals received ipsilateral injection of 0.02% ascorbic acid while all other rats received ipsilateral injection of freshly prepared 2 μl of 6-hydroxydopamine (6-OHDA, Sigma) at the concentration of 7.5 μg/μl containing 0.02% ascorbic acid at two coordinates in the right striatum (coordinate: AP, +0.7 mm; ML, +2.2 mm and +2.0 mm; DV, −5.0 mm). The injection rate was 0.5 μl/min, and the syringe was kept in place for an additional 5 min before being retracted slowly. Rats were sacrificed after 3, 5, and 14 days (6 rats per time point).

Immunohistochemistry

Rats were deeply anesthetized with sodium pentobarbital (120 mg/kg) and transcardially perfused with saline containing 0.5% sodium nitrite and 10 U/ml heparin sulfate, followed by 4% cold formaldehyde generated from paraformaldehyde in 0.1 M PBS (pH 7.2). Brains were post-fixed in the same solution for overnight and infiltrated with 30% sucrose overnight. Free-floating sections (40 μm) were obtained from the striata and SN using a Cryostat. Sections were washed in 0.1 M PBS, incubated in 0.1 M PBS containing 5% normal goat serum and 0.3% TritonX-100 for 1 h, and subsequently incubated overnight with TH (1:10,000), MDA (1:1000), or p-c-jun (1:1,000) antibodies at 4° C. For 7,8-dihydro-8-oxo-deoxyguanine (8-oxo-dG) staining, brain slides were incubated in 70% ethanol precooled to −20° C. for 10 min on ice followed by 4 N HCl to denature DNA. After rinsing with PBS, the slides were soaked in 37° C. PBS supplemented with 100 μg/ml DNase-free RNase A for 1 h. Blocking for immunostaining was done in PBS containing 5% FBS, 5% horse serum, and 0.05% Triton-X100 for 2 h. The slides were incubated with primary mouse anti-8-oxo-dG antibody (1:300) in PBS containing 2.5% FBS, 2.5% horse serum, and 0.05% Triton-X-100 overnight at 4° C. The sections were then incubated with appropriate secondary IgG (1:200) for 1 h, followed by avidin/biotin/peroxidase staining for 1 h in a humidified chamber. Washing of the sections on slides was done using 0.1 M PBS containing 1.5% bovine serum albumin that was used to wash sections between all steps. The antigen-antibody complexes were visualized by incubation for 5 min in 0.05% 3,3'-diaminobenzidine and 0.003% $H_2O_2$. Nissl staining was performed by incubation of sections in 0.1% Cresyl violet solution for 5-10 min at room temperature and rinsed quickly in distilled water, and dehydrated in serially diluted ethanol, and cleaned in xylene followed by sequential mounting in glass slides using permanent mounting medium. Mounted slices were evaluated on light microscope.

Double-fluorescent Immunostaining of Tissues

Free-floating sections (40 μm) were washed in 0.1 M PBS, incubated in 0.1 M PBS containing 5% normal donkey serum and 0.3% TritonX-100 for 1 h, and subsequently incubated overnight with primary antibodies (TH, 1:2,000; Nox1, 1:200; GFAP, 1:500; CD11b, 1:200) in 2% normal donkey serum in PBS at 4° C. and incubated in a 1:200 dilution of AlexaFluor conjugated donkey anti-rabbit (546) or donkey anti-mouse (488) antibodies for 1 h at room temperature, washed with PBS, incubated in TOTO-3 (1:1,000) in 0.1 M PBS for 5 min, and then mounted sequentially in glass slides using Vectashield. Mounted slices were evaluated for fluorescence under settings for 546, 488, and 660 nm emissions on a confocal microscope (Leica TCS SP5).

TH Immunostaining and TH-positive Cells Counting

A set consisting of six sections, 360 μm apart, were prepared. Sections were used for tyrosine hydroxylase (TH) immunohistochemistry using avidin-biotin peroxidase technique (Vectastain ABC kit from Vector Labs, Burlingame, Calif.). A rabbit anti-TH affinity purified antibody (1: 10,000; from Protos Biotech, New York, N.Y.) was used. Numbers of TH-immunoreactive cells in the substantia nigra (SN) were counted using the optical fractionator (West 1990). Analysis was performed using a system consisting of a Nikon Eclipse E600 microscope (Morrell Instruments Co. Inc., Melville, N.Y.) equipped with a computer-controlled LEP BioPoint motorized stage (Ludl Electronic Products, Hawthorne, N.Y.), a DEI-750 video camera (Meyer Instruments, Houston, Tex.), a Dell Dimension 4300 computer (Dell, Round Rock, Tex.), and the Stereo Investigator (v. 4.35) software program (Microbrightfield, Burlington, Vt.). Tissue sections were examined using a Nikon Plan Apo 100•objective lens with a 1.4 numerical aperture. The size of the x-y sampling grid was 140 μm. The counting frame thickness was 30 μm and the counting frame area was 4900 μm². The coefficient of error and coefficient of variation were also determined.

Immunocytochemistry

For fluorescent immunostaining, N27 cells in the 4-well chamber slide were incubated for 1 h at 37° C. in 2% normal donkey serum containing either a rabbit polyclonal antibody against Nox1 (1:500), or p-c-jun (1:500). For 7,8-dihydro-8-oxo-deoxyguanine (8-oxo-dG) staining, slides were incubated in 70% ethanol pre-cooled to −20° C. for 10 min on ice. After rinsing with PBS, the slides were soaked in 37° C. PBS supplemented with 100 mg/ml RNase A, DNase-free for 1 h. Blocking for immunostaining was done in PBS containing 5% FBS, 5% horse serum, and 0.05% Triton-X100 for 2 h. The slides were incubated with primary mouse anti-8-oxo-dG antibody (1:300) in PBS containing 2.5% FBS, 2.5% horse serum, and 0.05% Triton-X-100 overnight at 4° C. Specific binding was detected by incubation for 60 min at room temperature with a 1:200 dilution of secondary antibodies conjugated to AlexaFluor 546 dyes. For determination of cell death, cells were stained with the TdT-mediated dUTP-X nick end labeling (TUNEL) reaction mixture (Roche Applied Science) that contains TdT and TMR (fluorescein-labeled) -dUTP for 60 min at 37° C. in a humidified atmosphere in the dark. Slides were washed with 0.1 M PBS and then mounted sequentially in glass slides using Vectashield (Vector Labs). Mounted slices were evaluated for fluorescence under settings for 546 and 488 nm emissions on a confocal microscope.

Data Analysis

Data were expressed as means+standard error of the mean (SEM) and were analyzed using one way analysis of variance (ANOVA) and Student-Newman-Keul's test for individual comparisons. P values less than 0.05 were considered statistically significant.

References Related To Example 1

1. Akbari M. Otterlei M. Pena-Diaz J. Krokan H E. Different organization of base excision repair of uracil in DNA in nuclei and mitochondria and selective upregulation of 1. mitochondrial uracil-DNA glycosylase after oxidative stress. Neuroscience. 2007; 145:1201-1212.
2. Alam Z I. Jenner A. Daniel S E. Lees A J. Cairns N. Marsden C D. Jenner P. Halliwell B. Oxidative DNA damage in the parkinsonian brain: An apparent selective increase in 8-hydroxyguanine levels in substantia nigra. J Neurochem. 1997; 69:1196-1203.
3. Anantharam V. Kaul S. Song C. Kanthasamy A. Kanthasamy A G. Pharmacological inhibition of neuronal NADPH oxidase protects against 1-methyl-4-phenylpyridinium (MPP+)-induced oxidative stress and apoptosis in mesencephalic dopaminergic neuronal cells. Neurotoxicology. 2007; 28:988-997.
4. Banfi B. Clark R A. Steger K. Krause K H. Two novel proteins activate superoxide generation by the NADPH oxidase NOX1. J Biol Chem. 2003; 278:3510-3513.
5. Bedard K. Krause K H. The NOX family of ROS-generating NADPH oxidases: Physiology and pathophysiology. Physiol Rev. 2007; 87:245-313.
6. Behrens M M. Ali S S. Dao D N. Lucero J. Shekhtman G. Quick K L. Dugan L L. Ketamine-induced loss of phenotype of fast-spiking interneurons is mediated by NADPH-oxidase. Science. 2007; 318:1645-1647.
7. Bender A. Krishnan K J. Morris C M. Taylor G A. Reeve A K. Perry R H. Jaros E. Hersheson J S. Betts J. Klopstock T. Taylor R W. Turnbull D M. High levels of mitochondrial DNA deletions in substantia nigra neurons in aging and Parkinson disease. Nat Genet. 2006; 38:515-517.
8. Bjorklund A. Kirik D. Rosenblad C. Georgievska B. Lundberg C. Mandel R J. Towards a neuroprotective gene therapy for Parkinson's disease: Use of adenovirus, AAV and lentivirus vectors for gene transfer of GDNF to the nigrostriatal system in the rat Parkinson model. Brain Res. 2000; 886:82-98.
9. Bokoch G M. Diebold B A. Current molecular models for NADPH oxidase regulation by Rac GTPase. Blood. 2002; 100:2692-2696.
10. Chamulitrat W. Schmidt R. Tomakidi P. Stremmel W. Chunglok W. Kawahara T. Rokutan K. Association of gp91 phox homolog Nox1 with anchorage-independent growth and MAP kinase-activation of transformed human keratinocytes. Oncogene. 2003; 22:6045-6053.
11. Cheng G. Cao Z. Xu X. van Meir E G. Lambeth J D. Homologs of gp91 phox: Cloning and tissue expression of Nox3, Nox4, and Nox5. Gene. 2001; 269:131-140.
12. Choi D H. Kim Y J. Kim Y G. Joh T H. Beal M F. Kim Y S. Role of matrix metalloproteinase 3-mediated alpha-synuclein cleavage in dopaminergic cell death. J Biol Chem. 2011; 286:14168-14177.
13. Cristovao A C. Choi D H. Baltazar G. Beal M F. Kim Y S. The role of NADPH oxidase 1-derived reactive oxygen species in paraquat-mediated dopaminergic cell death. Antioxid Redox Signal. 2009; 11:2105-2118.
14. Daiber A. Redox signaling (cross-talk) from and to mitochondria involves mitochondrial pores and reactive oxygen species. Biochim Biophys Acta. 2010; 1797:897-906.
15. De Deken X. Wang D. Many M C. Costagliola S. Libert F. Vassart G. Dumont J E. Miot F. Cloning of two human thyroid cDNAs encoding new members of the NADPH oxidase family. J Biol Chem. 2000; 275:23227-23233.
16. Desouki M M. Kulawiec M. Bansal S. Das G M. Singh K K. Cross talk between mitochondria and superoxide generating NADPH oxidase in breast and ovarian tumors. Cancer Biol Ther. 2005; 4:1367-1373.
17. Edens W A. Sharling L. Cheng G. Shapira R. Kinkade J M. Lee T. Edens H A. Tang X. Sullards C. Flaherty D B. Benian G M. Lambeth J D. Tyrosine cross-linking of extracellular matrix is catalyzed by Duox, a multidomain oxidase/peroxidase with homology to the phagocyte oxidase subunit gp91 phox. J Cell Biol. 2001; 154:879-891.
18. Fan C Y. Katsuyama M. Yabe-Nishimura C. PKCdelta mediates up-regulation of NOX1, a catalytic subunit of NADPH oxidase, via transactivation of the EGF receptor: Possible involvement of PKCdelta in vascular hypertrophy. Biochem J. 2005; 390:761-767.
19. Geiszt M. Lekstrom K. Brenner S. Hewitt S M. Dana R. Malech H L. Leto T L. NAD(P)H oxidase 1, a product of differentiated colon epithelial cells, can partially replace glycoprotein 91 phox in the regulated production of superoxide by phagocytes. J Immunol. 2003; 171:299-306.
20. Geiszt M. Lekstrom K. Witta J. Leto T L. Proteins homologous to p47phox and p67phox support superoxide production by NAD(P)H oxidase 1 in colon epithelial cells. J Biol Chem. 2003; 278:20006-20012.
21. Glinka Y. Gassen M. Youdim M B. Mechanism of 6-hydroxydopamine neurotoxicity. J Neural Transm Suppl. 1997; 50:55-66.
22. Gordillo G. Fang H. Park H. Roy S. Nox-4-dependent nuclear H2O2 drives DNA oxidation resulting in 8-OHdG as urinary biomarker and hemangioendothelioma formation. Antioxid Redox Signal. 12:933-943.
23. Hilenski L L. Clempus R E. Quinn M T. Lambeth J D. Griendling K K. Distinct subcellular localizations of Nox1 and Nox4 in vascular smooth muscle cells. Arterioscler Thromb Vasc Biol. 2004; 24:677-683.
24. Infanger D W. Sharma R V. Davisson R L. NADPH oxidases of the brain: Distribution, regulation, and function. Antioxid Redox Signal. 2006; 8:1583-1596.
25. Katsuyama M. Fan C. Arakawa N. Nishinaka T. Miyagishi M. Taira K. Yabe-Nishimura C. Essential role of ATF-1 in induction of NOX1, a catalytic subunit of NADPH oxidase: Involvement of mitochondrial respiratory chain. Biochem J. 2005; 386:255-261.
26. Kawahara T. Kohjima M. Kuwano Y. Mino H. Teshima-Kondo S. Takeya R. Tsunawaki S. Wada A. Sumimoto H. Rokutan K. *Helicobacter pylori* lipopolysaccharide activates Rac1 and transcription of NADPH oxidase Nox1 and its organizer NOXO1 in guinea pig gastric mucosal cells. Am J Physiol Cell Physiol. 2005; 288:C450-457.
27. Kuroda J. Nakagawa K. Yamasaki T. Nakamura K. Takeya R. Kuribayashi F. Imajoh-Ohmi S. Igarashi K. Shibata Y. Sueishi K. Sumimoto H. The superoxide-producing NAD(P)H oxidase Nox4 in the nucleus of human vascular endothelial cells. Genes Cells. 2005; 10:1139-1151.
28. Lee S B. Bae I H. Bae Y S. Um H D. Link between mitochondria and NADPH oxidase 1 isozyme for the sustained production of reactive oxygen species and cell death. J Biol Chem. 2006; 281:36228-36235.
29. Marden J J. Harraz M M. Williams A J. Nelson K. Luo M. Paulson H. Engelhardt J F. Redox modifier genes in amyotrophic lateral sclerosis in mice. J Clin Invest. 2007; 117:2913-2919.
30. Michaelson D. Abidi W. Guardavaccaro D. Zhou M. Ahearn I. Pagano M. Philips M R. Rac1 accumulates in the nucleus during the G2 phase of the cell cycle and promotes cell division. J Cell Biol. 2008; 181:485-496.
31. Migliore L. Petrozzi L. Lucetti C. Gambaccini G. Bernardini S. Scarpato R. Trippi F. Barale R. Frenzilli G. Rodilla V. Bonuccelli U. Oxidative damage and cytogenetic analysis in leukocytes of Parkinson's disease patients. Neurology. 2002; 58:1809-1815.
32. Nakabeppu Y. Tsuchimoto D. Yamaguchi H. Sakumi K. Oxidative damage in nucleic acids and Parkinson's disease. J Neurosci Res. 2007; 85:919-934.

33. Nikolova S. Lee Y S. Kim J A. Rac1-NADPH oxidase-regulated generation of reactive oxygen species mediates glutamate-induced apoptosis in SH-SY5Y human neuroblastoma cells. Free Radic Res. 2005; 39:1295-1304.

34. Nouspikel T. DNA repair in differentiated cells: Some new answers to old questions. Neuroscience. 2007; 145:1213-1221.

35. Prasad K N. Carvalho E. Kentroti S. Edwards-Prasad J. Freed C. Vernadakis A. Establishment and characterization of immortalized clonal cell lines from fetal rat mesencephalic tissue. In Vitro Cell Dev Biol Anim. 1994; 30A:596-603.

36. Qin B. Cartier L. Dubois-Dauphin M. Li B. Serrander L. Krause K H. A key role for the microglial NADPH oxidase in APP-dependent killing of neurons. Neurobiol Aging. 2006; 27:1577-1587.

37. Rodriguez-Lebron E. Denovan-Wright E M. Nash K. Lewin A S. Mandel R J. Intrastriatal rAAV-mediated delivery of anti-huntingtin shRNAs induces partial reversal of disease progression in R6/1 Huntington's disease transgenic mice. Mol Ther. 2005; 12:618-633.

38. Rodriguez-Pallares J. Parga J A. Munoz A. Rey P. Guerra M J. Labandeira-Garcia J L. Mechanism of 6-hydroxydopamine neurotoxicity: The role of NADPH oxidase and microglial activation in 6-hydroxydopamine-induced degeneration of dopaminergic neurons. J Neurochem. 2007; 103:145-156.

39. Rossi F. Zatti M. Biochemical aspects of phagocytosis in polymorphonuclear leucocytes. NADH and NADPH oxidation by the granules of resting and phagocytizing cells. Experientia. 1964; 20:21-23.

40. Schapira A H. Cooper J M. Dexter D. Jenner P. Clark J B. Marsden C D. Mitochondrial complex I deficiency in Parkinson's disease. Lancet. 1989; 1:1269.

41. Sherer T B. Greenamyre J T. Oxidative damage in Parkinson's disease. Antioxid Redox Signal. 2005; 7:627-629.

42. Silva R M. Kuan C Y. Rakic P. Burke R E. Mixed lineage kinase-c-jun N-terminal kinase signaling pathway: A new therapeutic target in Parkinson's disease. Mov Disord. 2005; 20:653-664.

43. Sorce S. Krause K H. NOX enzymes in the central nervous system: From signaling to disease. Antioxid Redox Signal. 2009; 11:2481-2504.

44. Stolk J. Hiltermann T J. Dijkman J H. Verhoeven A J. Characteristics of the inhibition of NADPH oxidase activation in neutrophils by apocynin, a methoxy-substituted catechol. Am J Respir Cell Mol Biol. 1994; 11:95-102.

45. Suh Y A. Arnold R S. Lassegue B. Shi J. Xu X. Sorescu D. Chung A B. Griendling K K. Lambeth J D. Cell transformation by the superoxide-generating oxidase Mox1. Nature. 1999; 401:79-82.

46. Ueyama T. Lekstrom K. Tsujibe S. Saito N. Leto T L. Subcellular localization and function of alternatively spliced Nox1 isoforms. Free Radic Biol Med. 2007; 42:180-190.

47. Van der Perren A. Toelen J. Carlon M. Van den Haute C. Coun F. Heeman B. Reumers V. Vandenberghe L H. Wilson J M. Debyser Z. Baekelandt V. Efficient and stable transduction of dopaminergic neurons in rat substantia nigra by rAAV 2/1, 2/2, 2/5, 2/6.2, 2/7, 2/8 and 2/9. Gene Ther. 2011; 18:517-527.

47a. West M J. Gundersen H J. Unbiased stereological estimation of the number of neurons in the human hippocampus. J Comp Neurol. 1990; 296:1-22.

48. Wosniak J J. Santos C X. Kowaltowski A J. Laurindo F. Cross-talk between mitochondria and NADPH oxidase: Effects of mild mitochondrial dysfunction on angiotensin II mediated increase in Nox isoform expression and activity in vascular smooth muscle cells. Antioxid Redox Signal. 2009; 11:1265-1278.

49. Wu D C. Teismann P. Tieu K. Vila M. Jackson-Lewis V. Ischiropoulos H. Przedborski S. NADPH oxidase mediates oxidative stress in the 1-methyl-4-phenyl-1,2,3,6-tetrahydropyridine model of Parkinson's disease. Proc Natl Acad Sci USA. 2003; 100:6145-6150.

50. Zekry D. Epperson T K. Krause K H. A role for NOX NADPH oxidases in Alzheimer's disease and other types of dementia? IUBMB Life. 2003; 55:307-313.

Example 2

Introduction

α-Synuclein, the principal component of Lewy bodies, has been reported as a cause of PD (Beyer et al., 2009; Cookson, 2009). The encoding gene of α-synuclein, SNCA, is the first gene where a strong correlation between its functional mutations and familial form of PD was demonstrated (Polymeropoulos et al., 1997; Krüger et al., 1998; Zarranz et al., 2004). While the molecular mechanism underlying its toxic effects on the nigrostriatal system is largely unknown, the aberrant expression and aggregation of α-synuclein have been considered as potential causes involved in neuronal toxicity (Vekrellis et al., 2011).

Evidence suggested that paraquat (PQ) is a specific neurotoxin for dopaminergic neurodegeneration in the substantia nigra (SN) (Brown et al., 2006; Gatto et al., 2010), and the structure of PQ suggests that increased oxidative stress might be the reason of its toxicity. The SN of PD patients' postmortem brain tissues showed high oxidative stress with an increase in lipid peroxidation (Dexter et al., 1989), oxidative damages in DNA (Zhang et al., 1999) and protein (Alam et al., 1997), and decreased glutathione levels (Sofic et al., 1992). Evidence has demonstrated that the NADPH oxidase (Nox) complexes also play a role in generating reactive oxygen species (ROS) beside mitochondria, and are implicated in several pathologic conditions in CNS (Sorce and Krause, 2009). Our previous results showed that Nox1, an isoform of the Nox family, has a role in PQ-mediated dopaminergic neuronal cell death both in vivo and in cell cultures (Cristovao et al., 2009). Recently, it was demonstrated that Nox1/Rac1 is activated in dopaminergic neurons following 6-hydroxydopamine (6-OHDA) treatment as well, causing oxidative stress and consequential neuronal death (Choi et al., 2012). Since oxidative stress is generally considered as a factor affecting α-synuclein aggregation (Krishnan et al., 2003), PQ-mediated oxidative stress was also shown to increase α-synuclein aggregation and expression levels in the SN of mice (Manning-Bog et al., 2002). Halting the expression levels of α-synuclein in a mouse model of PD was shown to be beneficial with reduced progression of neurodegeneration (Nuber et al., 2008). Understanding how α-synuclein expression and aggregation is regulated will provide one with targets that ultimately may be used to control and reduce the progression of certain aspects of the disease phenotype.

In the present example, the effect of Nox1-derived ROS on the expression and aggregation of α-synuclein in the SN of rats exposed to PQ is examined. It was demonstrated that PQ-treated rats show noticeable α-synuclein increased expression and aggregation, which were clearly reduced in Nox1 knockdown.

Materials and Methods

Cell Cultures

ReNcell VM Culture Method.

For the in vitro experiments on human dopaminergic neurons, human mesencephalic neuronal progenitor cell line available from Millipore (catalog number SCC008) was used. The specialty of these cells is that they are isolated from fetal human ventral mesencephalic region and subsequently immortalized by introduction of v-myc. The cells can readily differentiate into dopaminergic neurons upon withdrawal of growth factors (Millipore). The culture method was followed as indicated by the company with little modifications. Briefly, the cells were allowed to grow on laminin-coated (20 μg/ml) dishes in DMEM/F12-containing medium with B27 supplement, glutamax, heparin (10 U/ml), and gentamicin (50 μg/ml). This medium is called maintenance medium. Cell division was allowed by addition of the two growth factors in the medium viz., basic fibroblast growth factor (bFGF) and epidermal growth factor (EGF), both at a concentration of 20 ng/ml. To induce differentiation, both growth factors were removed from the media and the cells were allowed to differentiate for 14 d with changing medium every alternate day before harvesting or any treatment. After differentiation, cells were treated with 800 μM or 1000 μM PQ for 8 and 24 h.

Immortalized Rat Mesencephalic Dopaminergic Cell (N27 Cells) Culture.

The N27 cells were grown in RPMI 1640 medium containing 10% fetal bovine serum (FBS), 100 U penicillin, and 50 μg/ml streptomycin, in a humidified atmosphere of 5% $CO_2$ at 37° C. N27 cultures were prepared for experiments by plating the cells on polystyrene tissue culture dishes at a density of $0.5 \times 10^5$ cells/well in 24-well culture plates with glass coverslip and at $1.5 \times 10^5$ cells/well in 6-well culture plates.

Animals and Treatment Paradigm.

Figure 13:
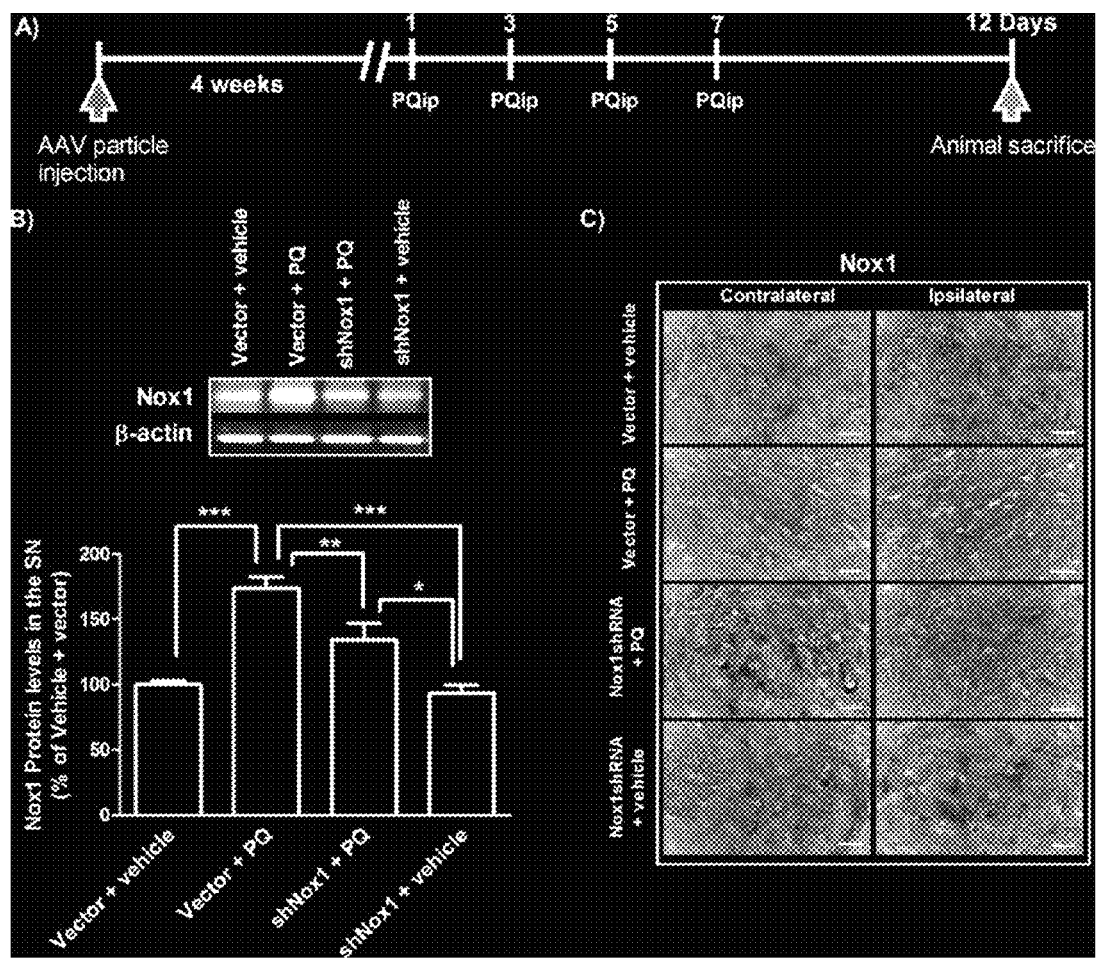
FIG. 13 Selective Nox1 targeting by AAV-mediated Nox1 knockdown in the rat SN. A, AAV2 viral particles and PQ injection paradigm diagram. To knockdown Nox1 in the SN, AAV2 particles harboring Nox1 sh RNA were stereotaxically injected into the SN. PQ intraperitoneal injections were performed 4 weeks after AAV2 delivery. Rats were divided into four groups. Group vector+vehicle: stereotaxic injection of AAV2 particles containing GFP vector and then vehicle (saline) intraperitoneal injection; group vector+PQ: stereotaxic injection of AAV2 particles containing GFP vector and then PQ intraperitoneal injection; group shNox1+PQ: stereotaxic injection of AAV2 particles harboring Nox1 shRNA-GFP and then PQ intraperitoneal injection; and group shNox1+vehicle: stereotaxic injection of AAV2 particles harboring Nox1 shRNA-GFP and then vehicle intraperitoneal injection. Animals were given a total of four intraperitoneal injections of either vehicle or PQ (10 mg/kg b.w.) every 2 d. All groups were killed 5 d post last injection. B, Representative immunoblot and quantitative analysis of Nox1 protein determined in total lysates of rat ipsilateral SN tissues. β-Actin was used as an internal control. Nox1 protein levels were quantified using Quantity One software and normalized against β-actin. The results are expressed as percentage of vector+vehicle. Data are shown as the mean±SEM. Statistical analysis was performed using one-way ANOVA followed by Bonferroni's multiple-comparison test; *p<0.05, p<0.01, and *p<0.001. (C) Representative photomicrographs of Nox1-immunoreactivity in the SN sections of the contralateral and ipsilateral sides of brain sections. Scale bars, 50 µm.

The experiments were performed on rats, in accordance with the National Institutes for Health Guide for the Care and Use of Laboratory Animals. All procedures were approved by the local Animal Care and Use Committee. Male Wistar rats (8-10 weeks; Charles River) were maintained in a temperature/humidity-controlled environment under a 12 h light/dark cycle with ad libitum access to food and water. As depicted in FIG. 13A, each animal received four intraperitoneal injections, separated by 1 d, of either vehicle (saline) or PQ (10 mg/kg body weight; b.w.), according to a previously published dose (Manning-Bog et al., 2002; Harraz et al., 2008; Cristovao et al., 2009). All animals were weighed at day 1 and 12. In the studies using the paradigm depicted in FIG. 13A, 4 weeks before starting PQ intraperitoneal injection, animals were stereotaxically injected with various viral constructs at the right SN using the following coordinates: mediolateral, +2.0; anteroposterior, −5.3; dorsoventral, −6.8. Animals were organized into four groups: vector+vehicle: stereotaxically injected with adeno-associated virus (AAV) particles containing a green fluorescent protein (GFP) vector (vector) and then intraperitoneally injected with saline (vehicle) (n=10); vector+PQ: stereotaxically injected with vector and then intraperitoneally injected with PQ (n=10); shNox1+PQ: stereotaxically injected with AAV particles harboring Nox1 shRNA and then intraperitoneally injected with PQ (n=10); shNox1+vehicle: stereotaxically injected with Nox1 shRNA and then intraperitoneally injected with vehicle (n=8). AAV containing GFP vector was used as a negative control. Five days after the last PQ intraperitoneal injection, animals were killed. For Western blot analysis, brains were collected and total protein lysates from SN were prepared. For immunohistochemical analysis, animals were intracardially perfused before collecting the brains.

Construction of shRNA Delivery Vector U6-CMV-EGFP/pAAV (AAV-Nox1 shRNA) and Preparation of rAAV2 Containing Nox1 shRNA U6 promoter-driven shRNA expression system was established in AAV serotype 2 (AAV2) vector. Enhanced GFP (EGFP) expression is separately controlled by a cytomegalovirus (CMV) promoter as a marker for the transduction efficiency. Rat Nox1 shRNA was designed based on the siRNA sequence, which efficiently knocked down Nox1 expression in N27 cells (Cristovao et al., 2009).

The plasmid DNA vector only or AAV-Nox1 shRNA was cotransfected with plasmids pHelper and pAAV-RC to HEK293 AAV cells using a standard calcium phosphate method. After 72 h, the cells were harvested and crude rAAV vector solutions were obtained by repeated freeze/thaw cycles. The cleared crude lysate was then applied on a heparin column. After the total lysate pass through the column, the matrix was washed twice with 25 ml of PBS with low NaCl (pH7.4, 0.1 M NaCl). The virus was then eluted with 15 ml of PBS with high NaCl (PBS; pH 7.4, 0.4 MNaCl). The elute was concentrated to ~1 ml with a Millipore Biomax-100K NMWL filter device (UFV2BHK40) by centrifugation 4000 rpm, 15-40 min. To adjust the NaCl concentration to physiological levels, the filter device was refilled with PBS, pH 7.4, and the virus was concentrated to 250-300 μl. After removal of the virus-containing solution, the membrane of the filter device was washed three times with PBS, pH 7.4, which was added to the main part of the recombinant AAV2. The fractions containing high-titer rAAV vectors were collected and used for injection into animals. The number of rAAV genome copies was semiquantified by PCR within the CMV promoter region using primers 5'-GACGTCAATAATGACGTATG-3' SEQ ID NO. 20 and 5'-GGTAATAGCGATGACTAATACG-3' SEQ ID NO. 21. The final titers were $6.4 \times 10^{11}$ genomes/μl (rAAV2-vector) and $5.5 \times 10^{11}$ genomes/μl (rAAV2-NOX-1 shRNA). Each animal received $16.5 \times 10^{11}$ genomes of the respective rAAV-vector.

Construction of shRNA Delivery Vector pLVX-shRNA2-zsGreen1/LVX (Lenti-Nox1 shRNA) and Preparation of Lentivirus Containing Nox1 shRNA The same Nox1 shRNA used for AAV2 construct was cloned into a pLVX-shRNA2 vector containing zsGreen1 (Clontech). To make lentiviral particles, ViraPower Lentiviral Expression System (Invitrogen) was used. The three packaging plasmids pLP1, pLP2, and pLP/VSVG, were individually purified from the mixture based on the pattern of restriction enzyme digestion. pLVX-shRNA2-rNox1 and the three packaging plasmids were cotransfected to Lenti-X 293T cells (Clontech) according to the Xfect transfection reagent protocol (Clontech). For 6-well plates, 8 μg of each plasmid was mixed in a 1:1:1:1 ratio in 100 μl of Xfect polymer buffer and then added to the cells. After 48 h, the viral-containing medium was harvested and centrifuged briefly at 500×g for 10 min to remove cellular debris and supernatant recovered and kept at −80° C. until used.

Transient Transfection of α-Synuclein Tagged with FLAG (N Terminal) and Myc (C Terminal)

Human α-synuclein was cloned into the p3xFLAG-myc-CMV-23 expression vector (Sigma) for N- and C-terminal tagging with FLAG and Myc, respectively. For transient overexpression of tagged α-synuclein, N27 cells were plated onto 24-well plates with coverslips at $0.5 \times 10^5$ cells per well 1 d before transfection. The next day, cells were transiently transfected with FLAG-WTsyn-myc. Briefly, 1 μg of plasmid DNA was mixed with 6 µl of Lipofectamine 2000 (Invitrogen) in 100 µl of Opti-MEM for 20 min before addition in the culture. After 6 h of incubation, the culture medium was changed and 100 µl of Nox1 shRNA/LVX viral particle was added to each well. Cells were maintained for an additional 36 h before treatment with 800 µM or 1000 µM PQ for 8 and 24 h.

Western Blot

For Western blot, brain tissues were lysed on ice in radio-immunoprecipitation assay buffer containing 50 mMTris/HCl, pH 8.0, 150 mM NaCl, 2 mM sodium orthovanadate, 1% Nonidet-P40 (NP-40), 0.5% sodium deoxycholate, and 0.1% SDS, containing 1% of a protease inhibitor mixture (AEBSF, pepstatinA, E-64, bestatin, leupeptin, and aprotinin). The soluble fraction was obtained and equal amounts of cell lysate protein were loaded in each lane of a 12% SDS-PAGE or 4/10% to 20% polyacrylamide gel. After electrophoresis and transfer onto a polyvinylidene difluoride (PVDF) membrane, specific protein bands were detected using appropriate primary antibodies (rabbit anti-Nox1, rabbit anti-α-synuclein, mouse anti-Ubiquitin, mouse anti-tyrosine hydroxylase (TH), and mouse anti-β-actin) and secondary antibodies conjugated to alkaline phosphatase or hydrogen peroxidase (anti-rabbit or anti-mouse) followed by Enhanced Chemifluorescence (ECF) detection or Enhanced Chemiluminescence (ECL).

Dot Blot Analysis

For dot blot, brain tissues were homogenized in a buffer containing 0.32 M sucrose, 1 mM $NaHCO_3$, 1 mM $MgCl_2$, 0.5 mM $CaCl_2$, and 1% of a protease inhibitor mixture (AEBSF, pepstatinA, E-64, bestatin, leupeptin, and aprotinin). The soluble fraction was obtained by centrifugation at 1000×g and 5 µl of each sample, containing the same amount of protein, was spotted in a PVDF membrane. Membrane was air dried for 4 h and blocked overnight at 4° C. in 5% nonfat dry milk TBST (10 mM Tris-HCl, pH 7.8, 100 mM NaCl, 0.05% Tween 20) solution. Protein spots were detected using the primary antibody, rabbit anti-A11 oligomer (0.5 µg/ml) from Invitrogen, and secondary antibody conjugated to hydrogen peroxidase (anti-rabbit) followed by ECL detection.

Measurement of Oxidized Proteins

The levels of protein carbonyl were measured in protein extracts from the SN tissues, using the OxiSelect Protein Carbonyl Immunoblot Kit (Cell Biolabs), according to the manufacturer's instructions, with small modifications. Briefly, 5% nonfat dry milk/PBST was used as blocking solution and antibody buffer, and the membrane was blocked for 1 h and incubated with the primary antibody overnight. Detection was performed using ECL.

Immunocytochemistry

After each respective treatment, cells were fixed in 4% paraformaldehyde (PFA) for 20 min and permeabilized with 0.1% Triton X-100 in PBS for 10 min. Blocking was performed by incubation with 20% goat or donkey serum in PBS containing 0.1% Tween 20 for 90 min at room temperature. The cells were then incubated for 120 min at room temperature with the following primary antibodies, according to the aim of the experiment: goat anti-Nox1 (1:50), rabbit anti-TH (1:10,000), mouse anti-Flag (1:150), mouse anti-α-synuclein (1:150), and rabbit anti-A11 (2.5 µg/ml). After washing, cells were incubated for 120 min with the appropriate secondary antibodies conjugated to Alexa Fluor 647 or Alexa Fluor 488 (1:1000). For nuclear visualization coverslips were incubated with 2 µM Hoechst for 10 min. For quantification of Flag+ and α-synuclein+ cells, >30 different fields per coverslip were analyzed on a Nikon inverted fluorescent microscope under a 20× and 40× magnification.

Immunohistochemistry

Following perfusion with saline and 4% PFA in PBS, brains were removed, and forebrain and midbrain blocks were immersion fixed in 4% PFA and cryoprotected in sucrose. Serial coronal sections (40 µm) were cut on a cryostat, collected in cryopreservative solution, and stored at −20° C. For immunolabeling studies, sections were incubated at room temperature with blocking solution for 1 h (5% FBS and 0.3% Triton X-100 in PBS, pH 7.5) and then with primary antibodies overnight. Finally, sections were incubated with secondary antibodies in blocking solution at room temperature for 1 h. The primary antibodies used were mouse anti-TH (1:10,000), rabbit anti-Nox1 (1:500), goat anti-4-HNE (1:700), mouse anti-ubiquitin (1:250), rabbit anti-α-synuclein (1:150), and rabbit anti-A11 oligomers (2.5 µg/ml). The secondary antibodies were biotinylated anti-rabbit IgG, anti-goat IgG, or anti-rat IgG (1:200). The staining procedure was performed as indicated by the manufacturer of the Vectastain ABC kit and the reaction product visualized using 3,3'-diaminobenzidine (DAB) reagent in TBS containing 0.02% $H_2O_2$. The numbers of TH-immunoreactive cells in the SN were counted using an optical fractionator. Analysis was performed using a system consisting of a Nikon Eclipse E600 microscope (Morrell Instruments) equipped with a computer-controlled LEP BioPoint motorized stage (Ludl Electronic Products), a DEI-750 video camera (Meyer Instruments), a Dell Dimension 4300 computer (Dell), and the Stereo Investigator (v. 4.35) software program (Microbrightfield).

Proteinase K Digestion of Cells and Tissues for α-Synuclein Aggregates Detection Immunocytochemistry for proteinase K (PK)-resistant α-synuclein was performed based on a methodology reported previously (Neumann et al., 2002), with some modifications. Briefly, fixed cells were permeabilized with 0.1% Tween 20 and then digested for 30 min at 37° C. with PK (10 µg/ml). PK was inactivated with 3 M guanidine thiocyanate in 10 mM Tris-HCl solution for 10 min. Between each step, cells were washed gently three times with PBS. Cells were then incubated for 60 min with blocking solution containing 10% donkey serum followed by an overnight incubation with mouse anti-α-synuclein antibody (1:150). The day after, cells were incubated with secondary antibodies conjugated to Alexa Fluor 647 donkey anti-mouse for 60 min and with 2 µM Hoechst solution for 10 min. For PK-resistant α-synuclein evaluation in rat SN, 40 µm sections from 4% PFA fixed tissues were washed twice in distilled water with 0.1% Tween 20, and then incubated for 30 min in TBST. The tissues were incubated for 90 min at 55° C. with 50 µg/ml PK in TBST and further washed three times in TBS. PK was denatured by incubating the tissues in a 3 M guanidine thiocyanate in 10 mM Tris-HCl solution for 10 min. Sections were incubated with blocking solution for 1 h (TBST with 0.2% casein) and then with rabbit anti-α-synuclein (1:150) at 4° C. overnight. Finally, sections were incubated with biotinylated anti-rabbit IgG (1:200 blocking solution) at room temperature for 1 h. The staining procedure was performed as indicated by the manufacturer of the Vectastain ABC kit and the reaction product visualized using DAB reagent in TBS containing 0.02% $H_2O_2$.

Data Analysis and Statistics

Statistical analysis was performed with GraphPad Prism v.5 (GraphPad Software). Data are expressed as percentages of values obtained in control conditions, and are presented as mean±SEM of at least four animals (in vivo studies). Statistical analyses were performed using the one-way ANOVA or two-way ANOVA followed by Bonferroni's multiple-comparison test, or using Student's t test. Values of p<0.05 were considered significant.

Reagents

FBS and gentamycin were purchased from Invitrogen BRL. Phenylmethylsulfonyl fluoride, NP-40, SP600125, Brij35, and bupropion were purchased from Sigma Chemicals. Mouse anti-TH was obtained from Transduction Laboratories; rabbit anti-Nox1, rabbit anti-α-synuclein, and mouse anti-ubiquitin were obtained from Santa Cruz Biotechnology; and mouse anti-α-synuclein from BD Transduction Laboratories. Goat anti-4-HNE and EGF were purchased from Millipore Bioscience Research Reagents. Rabbit anti-A11, Alexa Fluor 488 or Alexa Fluor 647, Hoechst 33342, Lipofectamine, ViraPower Lentiviral Expression System, 10-20% SDS polyacrylamide gel and 10-20% tricine gel, laminin, glutamax, DMEM/F12, and B27 supplement were purchased from Invitrogen. ECF Western Blotting kit was obtained from GE Healthcare Bioscience. Vectastain ABC kit, biotinylated anti-rabbit, anti-mouse IgG, or anti-goat IgG were from Vector Laboratories. Taq polymerase was from Roche Applied Science. PQ, protease inhibitor mixture (AEBSF, aprotinin, bestatin hydrochloride, E-64-[N-(trans-epoxysuccinyl)-L-leucine 4-guanidinobutylamide], leupeptin, pepstatin A), heparin, PK, and guanidine thiocyanate were from Sigma-Aldrich. bFGF was purchased from Peprotech. Millipore Biomax-100K NMWL filter device (UFV2BHK40) was purchased from Millipore. CMV-IRES-hrGFP/AAV system was purchased from Stratagene and the p3xFLAG-myc-CMV-23 expression vector from Sigma. pLVX-shRNA2-zsGreen1, Lenti-X 293T cells, and Xfect transfection reagent were purchased from Clontech. OxiSelect Protein Carbonyl Immunoblot Kit was purchased from Cell Biolabs. All other chemicals of reagent grade were from Sigma Chemicals or Merck.

Results

α-Synuclein and Nox1 Increases in Human Dopaminergic Neurons after PQ Treatment

Figure 7:
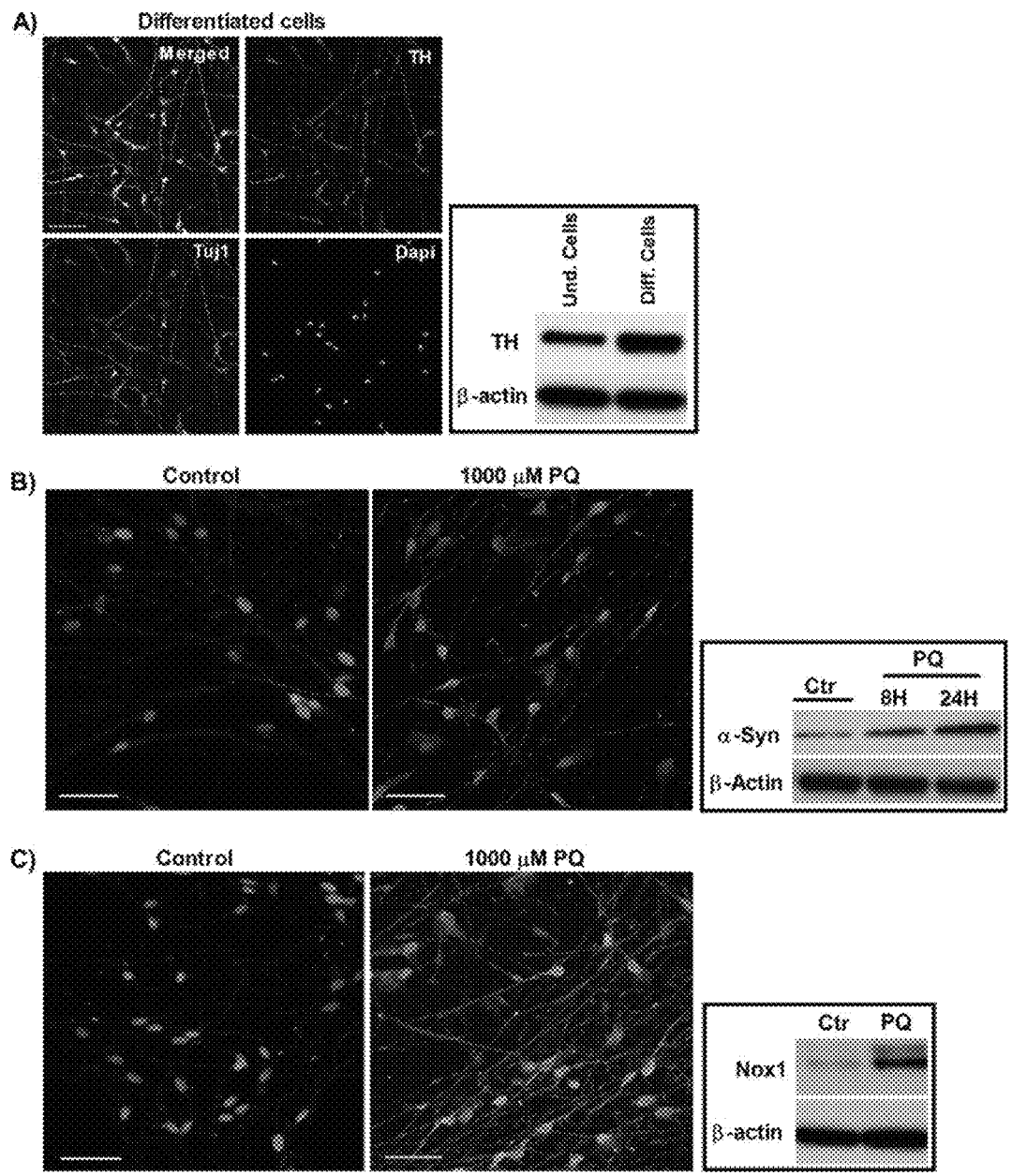
FIG. 7 Increases in α-synuclein and Nox1 in human dopaminergic neurons exposed to PQ. A, Characterization of human ventral mesencephalic neuronal progenitor cell line, ReNcell VM, after differentiation (human dopaminergic neurons). Left, Depicts representative photomicrographs of TH, Tuj1, and DAPI immunostaining of ReNcell VM after 14 days differentiation. Right, Displays the expression of TH protein in ReNcell VM, before and after differentiation. B, α-Synuclein levels in differentiated human dopaminergic cells exposed to PQ. Left, Shows α-synuclein immunoreactivity (red). Right, Represents α-synuclein protein levels in immunoblot. C, Nox1 levels in differentiated human dopaminergic cells exposed 8 h to PQ. Left, Shows Nox1 immunoreactivity (green). Right, Illustrates Nox1 protein levels in immunoblot. β-Actin was used as an internal control. Und, undifferentiated; Diff, differentiated; Ctr, control; PQ, paraquat. Scale bars: 50 μm.

To evaluate the effects of PQ treatment on α-synuclein and Nox1 expression in human dopaminergic neurons, human ventral mesencephalic neuronal progenitor cell line, ReNcell VM, was used (Donato et al., 2007). First differentiated was ReNcell VM into human midbrain neurons. After differentiation for 14 days, the obtained cultures were immunopositive for Tuj-1, a neuron-specific class III β-tubulin. Moreover, the majority (80%) of differentiated cells were TH positive, a specific marker of dopaminergic neuron, with an increased level of TH protein compared with undifferentiated cells (FIG. 7A). The effects of PQ on expression of α-synuclein and Nox1 were evaluated on these differentiated human dopaminergic cells. It was observed that differentiated dopaminergic neurons express α-synuclein, which increases over time under PQ treatment (FIG. 7B). Similarly, low basal level of Nox1 was highly elevated by PQ treatment, as shown by immunocytochemistry and Western blot analyses (FIG. 7C).

Overall, the results indicate that α-synuclein may be a key player in PQ-mediated dopaminergic neuronal toxicity. Moreover, the result also suggests that Nox1 may have an important role in the mechanism of human dopaminergic neurodegeneration as induced by PQ.

Figure 8:
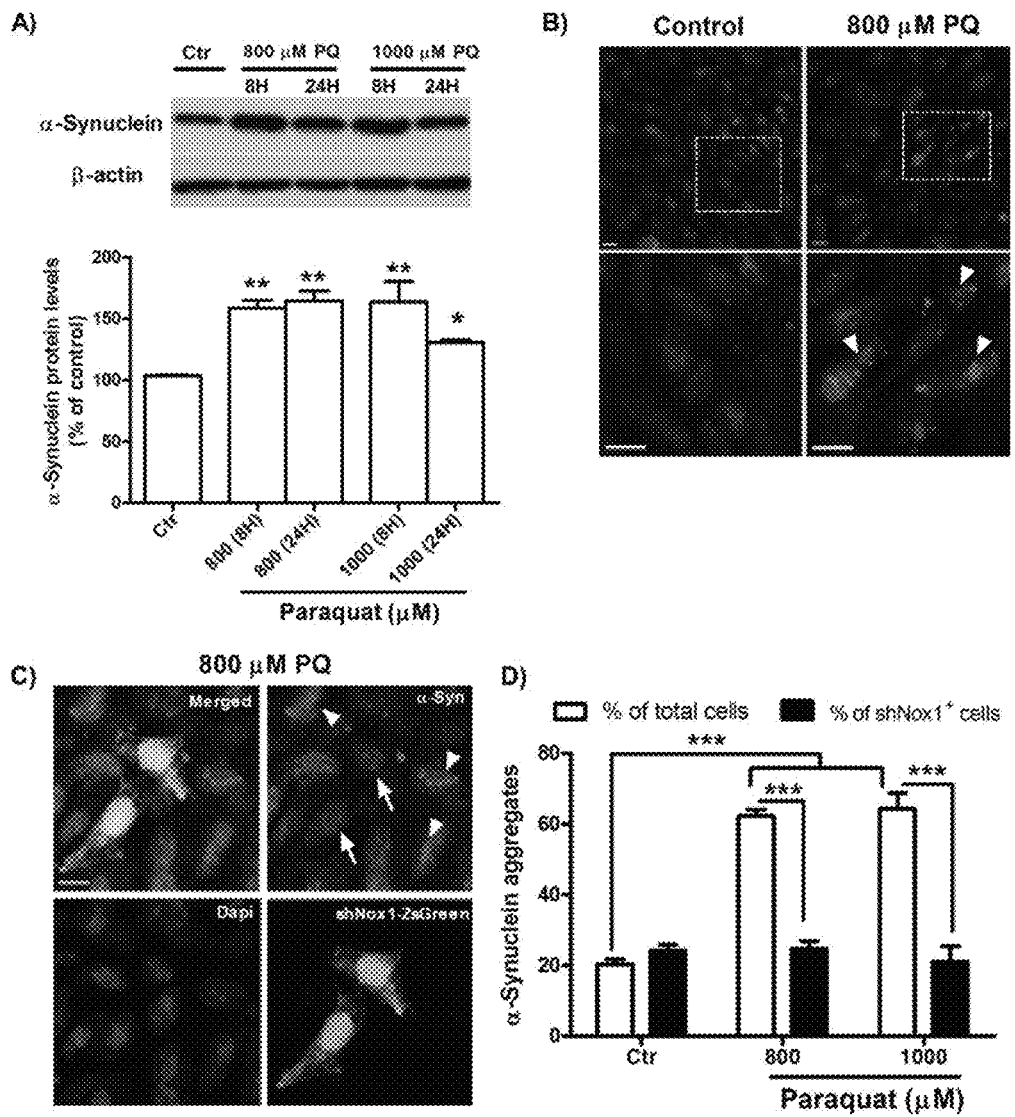
FIG. 8 PQ induces increases of α-synuclein expression and aggregation in N27 cells, an event prevented by Nox1 knockdown. A, Representative immunoblot and quantitative analysis of α-synuclein protein levels. α-Synuclein protein was determined in total lysates of N27 cells exposed to PQ or control. β-Actin was used as an internal control. PQ significantly increased α-synuclein protein levels, which were quantified using Quantity One software and normalized against β-actin. B, Photomicrographs of aggregated α-synuclein immunoreactivity (red) in control and PQ-treated cells. The bottom shows higher magnification of respective boxed areas in the top. C, α-Synuclein fluorescence immunostaining of N27 cells incubated with Nox1 shRNA/LVX (shNox1-ZsGreen) viral particles for 36 h and then exposed to 800 μM PQ. shNox1-ZsGreen-infected cells were identified by green fluorescence (ZsGreen) in cells. D, Quantification of the cells depicting the bright, punctuated fluorescence, like the ones indicated with arrowheads in B and C. More than 30 assigned fields were analyzed in each independent experiment and in average the minimum number of total cells counted per condition was 700 cells. Data are shown as the mean±SEM. Statistical analysis was performed using one-way ANOVA or two-way ANOVA, followed by Bonferroni's multiple-comparison test; *p<0.05, p<0.01, and *p<0.001. Arrowheads specify cells with aggregated α-synuclein pattern, and the arrow indicates N27 cells showing double-staining for shNox1-ZsGreen and α-synuclein. Ctr, control; PQ, paraquat. Scale bars: 10 μm.
Figure 14:
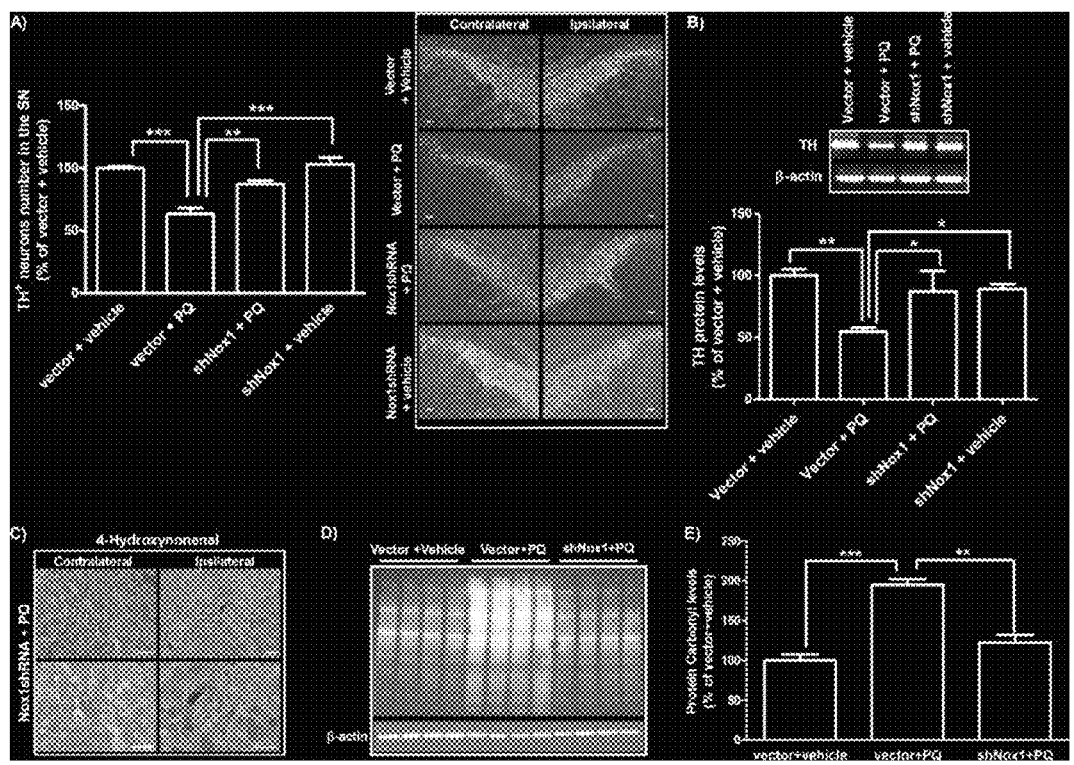
FIG. 14 Nox1 knockdown reduced SN dopaminergic neuronal death induced in rats administered with PQ. A, Representative photomicrographs of TH immunostaining and quantitative analysis of TH-positive dopaminergic neurons in the SN of rats after Nox1 knockdown. Representative photomicrographs of TH immunoreactivity in the SN of the contralateral and ipsilateral sides of brain sections of the four experimental groups. TH-positive neurons in the ipsilateral side were stereologically counted. B, Representative immunoblot and quantitative analysis of TH protein levels. TH protein was determined in total lysates of the rat's SN tissues in the ipsilateral side by immunoblot analysis. β-Actin was used as an internal control. TH protein levels were quantified using Quantity One software and normalized against β-actin. C, Representative photomicrographs of 4-HNE immunostaining in the SN of the contralateral and ipsilateral sides of brain sections of rats from shNox1+PQ group. Scale bars, 50 µm. D, E, Immunoblot (D) and quantitative analysis (E) of protein carbonyl levels determined in total lysates of rats' ipsilateral SN tissues. β-Actin was used as an internal control. The results are expressed as percentage of vector+vehicle. Data are shown as the mean±SEM. Statistical analysis was performed using one-way ANOVA followed by Bonferroni's multiple-comparison test; *p<0.05, p<0.01, and *p<0.001.

Nox1 Knockdown Significantly Reduces PQ-induced α-Synuclein Expression and Aggregation in Dopaminergic Cells To further study the role of Nox1 in α-synucleinopathy caused by PQ in dopaminergic cells, the rat dopaminergic neuronal cell line, N27 cells, was investigated. PQ significantly increased the levels of α-synuclein expression. Observed was 55 and 61% increases of α-synuclein protein levels in N27 cells exposed to 800 μM PQ for 8 and 24 h, respectively. When exposed to a 1000 μM dose of PQ, an increase of 60 and 27%, respectively, for 8 and 24 h incubation times was detected (FIG. 8A). Immunocytochemical evaluation showed that α-synuclein aggregation was also induced by PQ. As shown in FIG. 14B, increased immunoreactivity for α-synuclein in cultures treated with PQ was observed, and, moreover, a pattern of aggregated α-synuclein was observed in treated cultures, which was not detected in the untreated ones (FIG. 8B, arrowheads). The quantification of aggregated α-synuclein-positive cells revealed an increase of α-synuclein aggregation in cultures exposed to PQ compared with the control. As shown in FIG. 14D (open bars), a statistical increase of 62 and 64% in aggregation was found in cultures exposed for 24 h to 800 and 1000 μM PQ, respectively. To confirm the effect of PQ in α-synuclein aggregation, the levels of α-synuclein resistant to PK digestion were further evaluated, since it was previously reported that α-synuclein aggregates are resistant to limited PK digestion (Neumann et al., 2002). As shown in FIG. 15A, N27 cells exposed to PQ depict higher PK-resistant α-synuclein immunoreactivity, an indicator of higher α-synuclein aggregation. α-synuclein aggregation was further evaluated by investigating the levels of A11 immunoreactivity in untreated and PQ-treated N27 cell, as the anti-A11 oligomer antibody was previously reported to efficiently detect α-synuclein aggregation (Winner et al., 2011). FIG. 15B shows high A11 immunoreactivity in cultures exposed to PQ when compared with the controls, clearly indicating increased α-synuclein aggregation induced by PQ. As expected, this group of results infers that PQ induces increased levels of α-synuclein expression as well as aggregation.

To explore the contribution of Nox1 in the changes of α-synuclein induced by PQ, Nox1 was knocked down, using lentivirus-mediated Nox1 shRNA overexpression (shNox1-ZsGreen), and exposed N27 cells to PQ. The results showed that PQ-induced α-synuclein aggregation was lower in cells overexpressing Nox1 shRNA (FIG. 8C). After quantifying the number of cells depicting both shNox1-ZsGreen and α-synuclein aggregates, no statistical differences were found between untreated and PQ-treated cultures as shown in FIG. 14D (solid bars). The same result was found when analyzing A11 immunoreactivity in those cells. As shown in FIG. 15C, shNox1-ZsGreen-positive cells clearly had lower immunoreactivity for A11 compared with shNox1-ZsGreen-negative cells.

Figure 10:
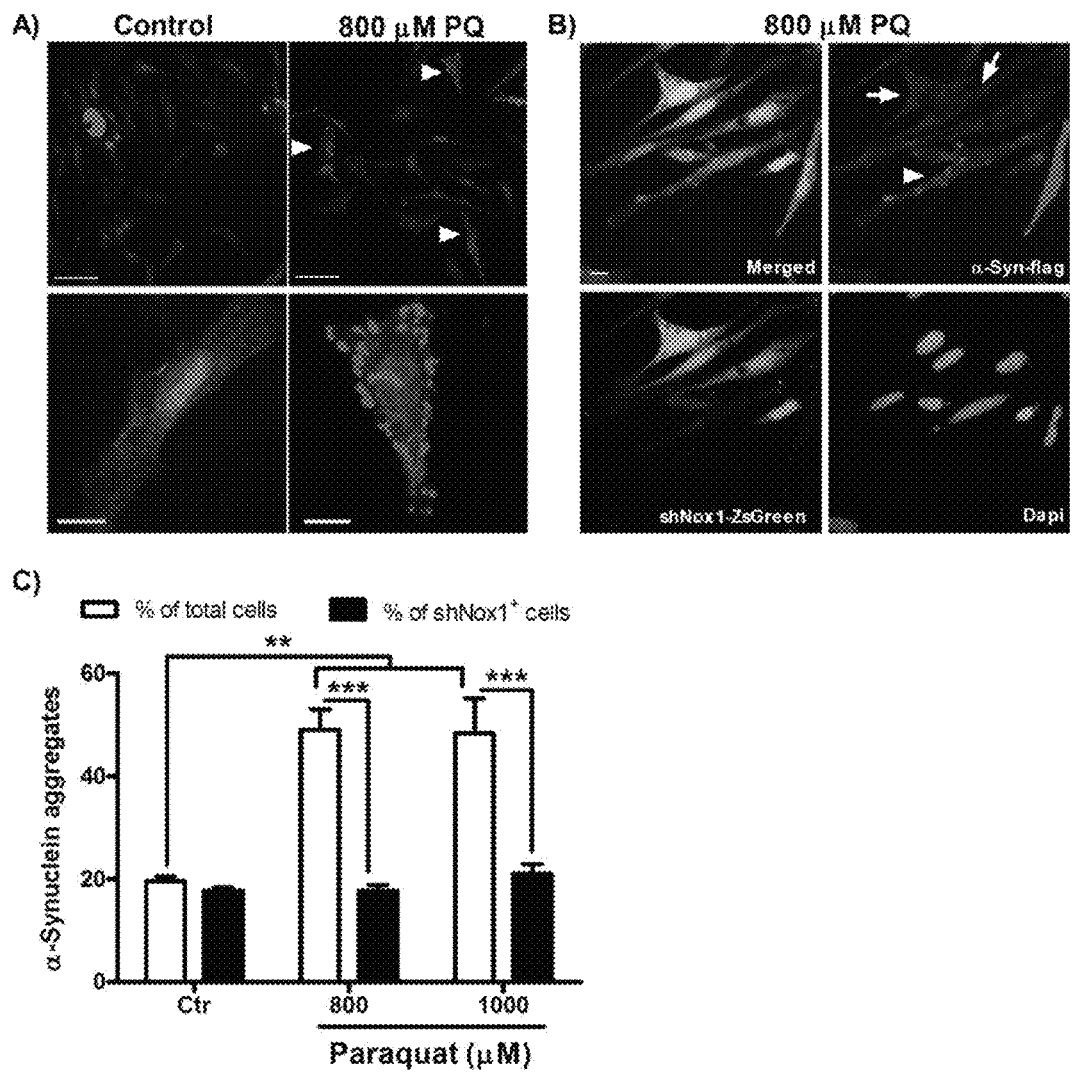
FIG. 10 Nox1 knockdown inhibits aggregation of overexpressed WT α-synuclein in N27 cells induced by PQ. A, Representative pictures of flag-tagged WT α-synuclein immunoreactivity (red) in control and PQ-treated cells. Scale bars: (for top), 50 μm; (for bottom), 10 μm. B, Flag-tagged WT α-synuclein fluorescence immunostaining of N27 cells incubated with Nox1 shRNA/LVX (shNox1-ZsGreen) viral particles and exposed to 800 μM PQ. shNox1-ZsGreen-infected cells were identified by green fluorescence (ZsGreen) in cells. Scale bar, 10 μm. C, Quantification of the bright, punctuated fluorescent cells, indicated with arrowheads in A and B. More than 20 assigned fields were analyzed in each independent experiment and in average the minimum number of total cells counted per condition was 400 cells. Data are shown as the mean±SEM. Statistical analysis was performed using one-way ANOVA or two-way ANOVA, followed by Bonferroni's multiple-comparison test; p<0.01 and *p<0.001. Arrowheads specify cells with aggregated α-synuclein pattern, and arrows indicate N27 cells depicting double-staining for shNox1-ZsGreen and α-synuclein-flag. Ctr, control; PQ, paraquat.

Next, it was sought to understand if Nox1 has a role only in the expression pathway of α-synuclein leading to protein increase and subsequent aggregation, or if it was also acting directly in its aggregation capability. Flag-tagged wild-type (WT) α-synuclein and shNox1-ZsGreen were overexpressed in N27 cells, and then cells were exposed to PQ. Strong cytoplasmic aggregation was induced by PQ treatment as detected by anti-flag immunostaining (FIG. 10A). A significant 2.5-fold increase of aggregation was observed in cells exposed to PQ when compared with control cells (FIG. 10C, open bars). Furthermore, when aggregation was analyzed in shNox1-ZsGreen-positive cells exposed to PQ, aggregation levels were not statistically different from control cells (FIG.

10C, solid bars). Aggregation was decreased by a 2.5-fold in shNox1-ZsGreen-positive cells (FIG. 10B, arrow) when compared with shNox1-ZsGreen-negative cells (FIG. 10B, arrowhead) for both concentrations of PQ (FIG. 10B,C).

Altogether the above results are highly suggestive that Nox1 is an important intermediary in regulation of both expression and the aggregation process of α-synuclein in dopaminergic cells stressed with PQ.

PQ Intraperitoneal Injection Causes Increases in α-Synuclein and Nox1 Protein Level as Well as Oxidative Stress in the Rat SN To validate the significance of our in vitro results, in vivo studies were conducted, using a PQ-inducing rat model of PD. Our first observations showed that PQ injection in rats induced an increase of 50% in α-synuclein protein levels in the SN as determined by Western blot (FIG. 11A). α-Synuclein immunoreactivity in the SN was also increased after PQ administration, as shown in FIG. 11B. The involvement of Nox1 in PQ-mediated dopaminergic cell death in mice was reported in a previous study of our group (Cristovao et al., 2009). In the present study, PQ insult also induced increased Nox1 protein level in the rat SN. As shown in FIG. 12A, animals exposed to PQ showed 58% higher levels of Nox1 protein than the group treated with vehicle. The upregulation of Nox1 in the SN of rats injected with PQ was further confirmed by immunohistochemistry as shown in FIG. 12B.

Nox enzymes are responsible for ROS production; it was then evaluated if increases in Nox1 were also accompanied by increased oxidative stress markers in rat tissues exposed to PQ. As depicted in FIG. 11C, an increase in 4-HNE immunoreactivity, a well established maker for lipid peroxidation, was found in the SN of rats treated with PQ compared with rats treated with vehicle. The above results are in accordance with the ones observed in vitro, and emphasize that under PQ insult, α-synuclein, Nox1, and oxidative stress may act as partners to enhance dopaminergic neurodegeneration.

The establishment of the rat model used in the present work was based on our previous reported results showing in mice the loss of dopaminergic neurons in the SN after PQ exposure (Cristóvão et al., 2009).

The Specific Knockdown of Nox1 Reduced Rat Dopaminergic Neuronal Loss Induced by PQ To investigate the role of Nox1 in oxidative stress, dopaminergic neuronal death, and α-synuclein expression and aggregation changes induced by PQ in rats achieved was Nox1 knockdown in the SN by using AAV-mediated Nox1 shRNA overexpression. Nox1 knockdown was achieved by stereotaxic delivery of AAV2 particles into the rat SN. PQ intraperitoneal injections were performed 4 weeks after the AAV2 injection, as depicted in FIG. 13A. AAV2 containing GFP vector was used as a negative control. To verify Nox1 knockdown efficiency, Nox1 levels in the SN of each group of animals were investigated by Western blot and immunohistochemistry analysis. Nox1 knockdown in the SN significantly reduced PQ-mediated Nox1 increases (FIG. 13B,C). As shown in FIG. 13B, animals treated with vector+PQ showed statistically higher levels of Nox1 protein (70%) compared with animals treated with vector+vehicle. Compared with animals treated with vector+PQ, animals treated with shNox1+PQ showed a 40% decrease in Nox1 protein levels in the SN (FIG. 13B). Nox1 levels in the SN of each group of animals were also investigated by immunohistochemistry, confirming the decrease in Nox1 immunoreactivity in the SN of animals exposed to Nox1 shRNA+PQ compared with the ones exposed to vector+PQ (FIG. 13C). These results confirmed that AAV-mediated Nox1 knockdown in vivo significantly reduced PQ-mediated increase in Nox1 level, validating our knockdown method.

To investigate the contribution of Nox1 to the dopaminergic neurotoxicity induced by PQ in each group of animals, the levels of TH protein in the SN were investigated by Western blot and the numbers of TH-positive dopaminergic neurons in the substantia nigra pars compacta were obtained by stereological analysis. Administration of vector+PQ significantly reduced TH protein levels to 65% compared with the control group injected with vector+vehicle, while TH protein levels were recovered to 87% in the group in which Nox1 was knocked down before PQ exposure (FIG. 14B). The stereological count of TH-positive neurons showed that Nox1 knockdown significantly reduced PQ-elicited dopaminergic neuronal loss from 37% in the group treated with vector+PQ to 13% in the Nox1 shRNA+PQ group (FIG. 14A). In addition, it was found that Nox1 knockdown also reduced oxidative stress levels, as shown by the levels of lipid peroxidation and protein oxidation. Increased immunoreactivity of 4-HNE (FIG. 14C) and protein carbonyl (FIG. 14D,E) in animals treated with PQ was decreased in the Nox1 shRNA+PQ group. Protein carbonyl levels were significantly increased by 95% after PQ exposure when compared with vector+PQ group, and reduced to 22% when Nox1 was knocked down (FIG. 14E). These results have shown that Nox1 knockdown reduced dopaminergic neuronal death and oxidative stress induced by PQ, which was in accordance with our two previous report observations showing that the Nox system plays an important role in PQ- and 6-OHDA-mediated dopaminergic neurotoxicity.

Increased Expression and Aggregation of α-Synuclein Induced by PQ Relies on Nox1 Protein in the Rat SN Herein, it was sought to evaluate the involvement of Nox1 in the effect of PQ on α-synuclein expression levels and aggregation in vivo. α-synuclein, protein aggregation, and ubiquitin levels was investigated in the SN of each group of animals by Western blot, dot blot, and immunohistochemical analyses. Significant increases of 54, 68, and 43% were found, in α-synuclein, A11-positive oligomers and ubiquitin protein levels, respectively, in the vector+PQ-treated group when compared with the vector+vehicle group (FIGS. 15A, 16A,C). Moreover, Nox1 knockdown reduced by 37, 50, and 43% the PQ-mediated α-synuclein, A11 oligomers, and ubiquitin levels, respectively, compared with the vector+PQ (FIGS. 15A, 16A,C). To further evaluate in vivo the effect of Nox1 knockdown on PQ-induced α-synuclein aggregation also investigated were the levels of α-synuclein resistant to PK digestion. An increase in PK-resistant α-synuclein immunoreactivity was observed in the rat SN exposed to vector+ PQ, but not in the vector+vehicle group. A significant reduction in PK-resistant α-synuclein staining was observed in the group in which Nox1 was knocked down before PQ injection (Nox1 shRNA+PQ) (FIG. 15B). Immunohistochemistry evaluations revealed a significant increase in the immunoreactivity of A11 oligomers in the SN of rats exposed to PQ, which was decreased in the group exposed to PQ in which Nox1 was knocked down (FIG. 16B). The involvement of Nox1 in PQ-induced changes in ubiquitin in the SN was also evaluated and the significant increase in ubiquitin immunoreactivity observed in the rat SN exposed to vector+PQ was reversed by Nox1 knockdown (Nox1 shRNA+PQ) (FIG. 16D). Together our results are highly suggestive of an active role of Nox1 in α-synucleinopathy induced by PQ at transcriptional levels as well as post-translational aggregation mechanism.

Discussion

Figure 11:
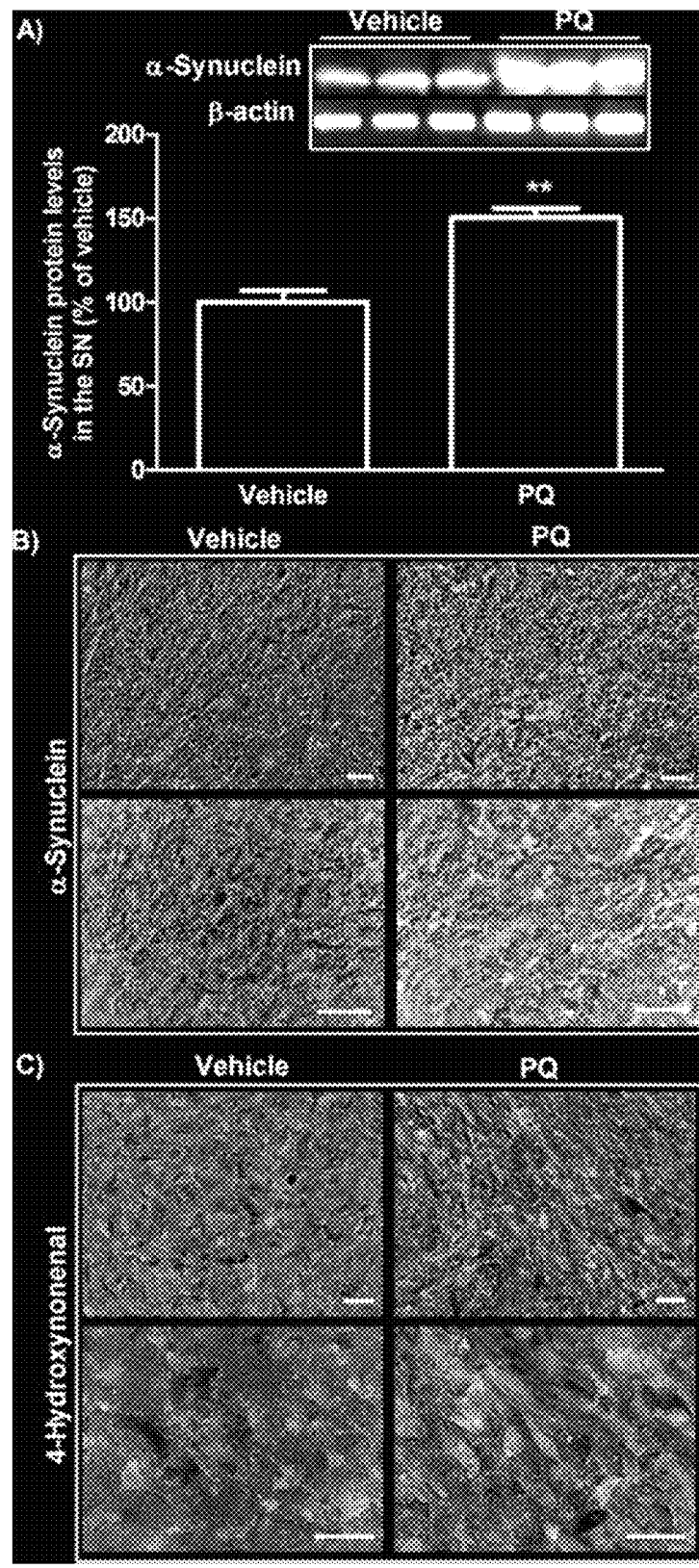
FIG. 11 Increase in α-synuclein and lipid peroxidation in the SN of rats administered with PQ. A, Representative immunoblot and quantitative analysis of α-synuclein protein levels. α-Synuclein protein was determined in the total lysates of SN tissues of rats injected with vehicle or PQ by immunoblot analysis. β-Actin was used as an internal control. PQ significantly increased α-synuclein protein levels, which were quantified using Quantity One software and normalized against β-actin. B, C, Representative photomicrographs of α-synuclein (B) and 4HNE (C) immunostaining in the SN of rats treated with vehicle or PQ. Data are shown as the mean±SEM. Statistical analysis was performed using the Student's t test; **p<0.01. Scale bars: 50 µm.
Figure 12:
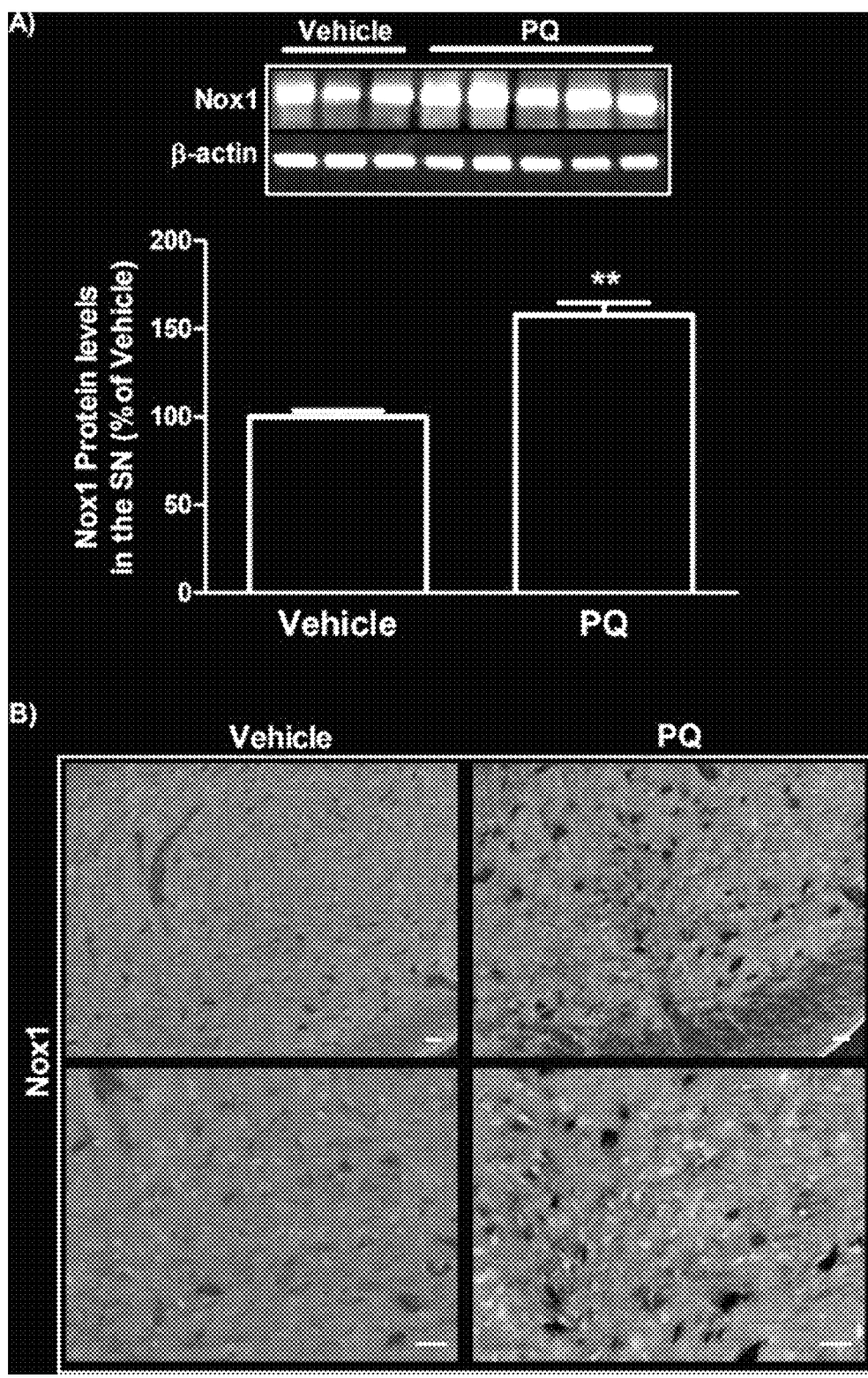
FIG. 12 Increase in Nox1 protein levels in the SN of rats injected with PQ. A, Representative immunoblot and quantitative analysis of Nox1 protein levels. Nox1 protein was determined in the total lysates of SN tissues of rats injected with vehicle or PQ by immunoblot analysis. β-Actin was used as an internal control. PQ significantly increased Nox1 protein, which was quantified using Quantity One software and normalized against β-actin. B, Representative photomicrographs of Nox1-immunoreactivity in the SN sections of rats injected with vehicle or PQ. Nox1 immunoreactivity in the SN was increased in PQ-injected animals compared with vehicle. The result is expressed as percentage of vehicle. Data are shown as the mean±SEM. Statistical analysis was performed using the Student's t test; **p<0.01. Scale bars: 50 µm.

In the present work, Nox1 is demonstrated as a crucial intermediary, between an environmental factor responsible for oxidative stress condition and α-synuclein transcriptional regulation and aggregation. Evidence is provided that suggests, under oxidative stress, as induced by PQ, α-synuclein expression and aggregation levels are increased, which can be ameliorated to normal by Nox1 knockdown. And most important, dopaminergic loss in the SN of rats exposed to PQ can also be recovered by Nox1 knockdown, suggesting that Nox1-derived ROS play a crucial role in α-synuclein pathology as along with dopaminergic neuronal degeneration.

α-Synuclein is a distinctive genetic factor in PD pathogenesis, in which its alterations and mutations were linked to the development of the disease (Beyer et al., 2009; Cookson, 2009). Oxidative stress has also been largely mentioned as a strong contributor to the development of the disease, and it has also been involved in PQ-induced dopaminergic neurodegeneration (Dexter et al., 1994; Alam et al., 1997; Zhang et al., 1999). Physiologically, ROS are generated as a byproduct of several biological reactions from organelles like mitochondria, and Nox is the specialized system that produces ROS, but not as a byproduct (Sorce and Krause, 2009), and our recent studies demonstrated that Nox1 serves as a major contributing factor in dopaminergic neuronal degeneration in both 6-OHDA and PQ-mediated PD rodent models (Cristovao et al., 2009; Choi et al., 2012). Our results using ReNcell VM cultures, which have been previously validated as an in vitro model of human dopaminergic neurons (Donato et al., 2007; Wood-Kaczmar et al., 2008), showed an increase in Nox1 level following PQ exposure (7C). Nox1 and the oxidative stress marker were also found increased in rats exposed to PQ (FIGS. 11, 12). The involvement of Nox1 in the mechanism of PQ-induced neurotoxicity was first demonstrated by our study, suggesting that Nox1 is involved in oxidative stress and consequent dopaminergic neuronal death (Cristovao et al., 2009). More recently, it was reported that Nox1-induced ROS also contributes to dopaminergic neurodegeneration induced by 6-OHDA (Choi et al., 2012), a well known toxin used to mimic PD pathogenesis in vitro and in vivo (Javoy et al., 1976; Terzioglu and Galter, 2008). It was shown that the nuclear localization of Nox1 is responsible for nuclear DNA damage and degeneration of dopaminergic neurons after 6-OHDA treatment. Altogether this evidence emphasizes the importance of Nox1 as a crucial participant in dopaminergic neurodegeneration.

α-Synuclein point mutations, A30P, A53T, and E46K, were found in the familial forms of early onset PD and they are responsible for the changes in α-synuclein aggregation properties (Hardy et al., 2009). Interestingly, elevated expression of WT α-synuclein due to the multiplications of SNCA has also been identified in early onset familiar PD (Singleton et al., 2003; Chartier-Harlin et al., 2004), leading to the view that WT protein could cause PD in a dose-dependent manner. Although this fact fortifies the importance of the transcriptional regulation of α-synuclein, relatively few studies have focused on the role of oxidative stress in the expression level and transcriptional control of α-synuclein. This is at least partly due to the lack of proper in vitro and in vivo model systems that successfully demonstrate the increased endogenous α-synuclein level. Importantly, in the current work, both in vitro and in vivo models showed significant changes in α-synuclein expression under PQ exposure. The levels of α-synuclein in ReNcells and N27 cells cultures exposed to PQ were prominently increased with time (FIGS. 7B, 8A), and significant increase in α-synuclein was also observed in the rat SN exposed to PQ as well (FIG. 11). Previous observations have shown that PQ increases α-synuclein expression levels and aggregation (Uversky et al., 2001; Manning-Bog et al., 2002), and that could be directly related to PQ-derived ROS generation (Krishnan et al., 2003). However, the molecular mechanism behind this effect is still elusive. Altogether these findings are suggestive of a possible relationship between increased ROS and the transcriptional regulation of α-synuclein, consistent with studies showing that toxic insults involving ROS production induce increased α-synuclein levels in the SN (McCormack et al., 2005). In PC12 cells as well as in primary cortical neurons from rat, it was demonstrated that α-synuclein expression in response to neurotrophins is regulated by the MAP/ERK and PI3-K pathways (Clough and Stefanis, 2007; Clough et al., 2011), which are also known to be activated under oxidative stress conditions (Miller et al., 2009). This suggests a possible relationship between increased ROS and transcriptional regulation of α-synuclein through these pathways. The above idea reinforces our hypothesis that Nox1-ROS generation might be a key regulator controlling α-synuclein expression. Nevertheless, the effects of ROS in transcriptional regulation are broad, including epigenetic alterations (Zawia et al., 2009), transcription factors binding regulation (Clough et al., 2009), or DNA damage (Turk et al., 1995). How Nox1-derived ROS regulates the transcription of α-synuclein remains to be investigated.

Figure 9:
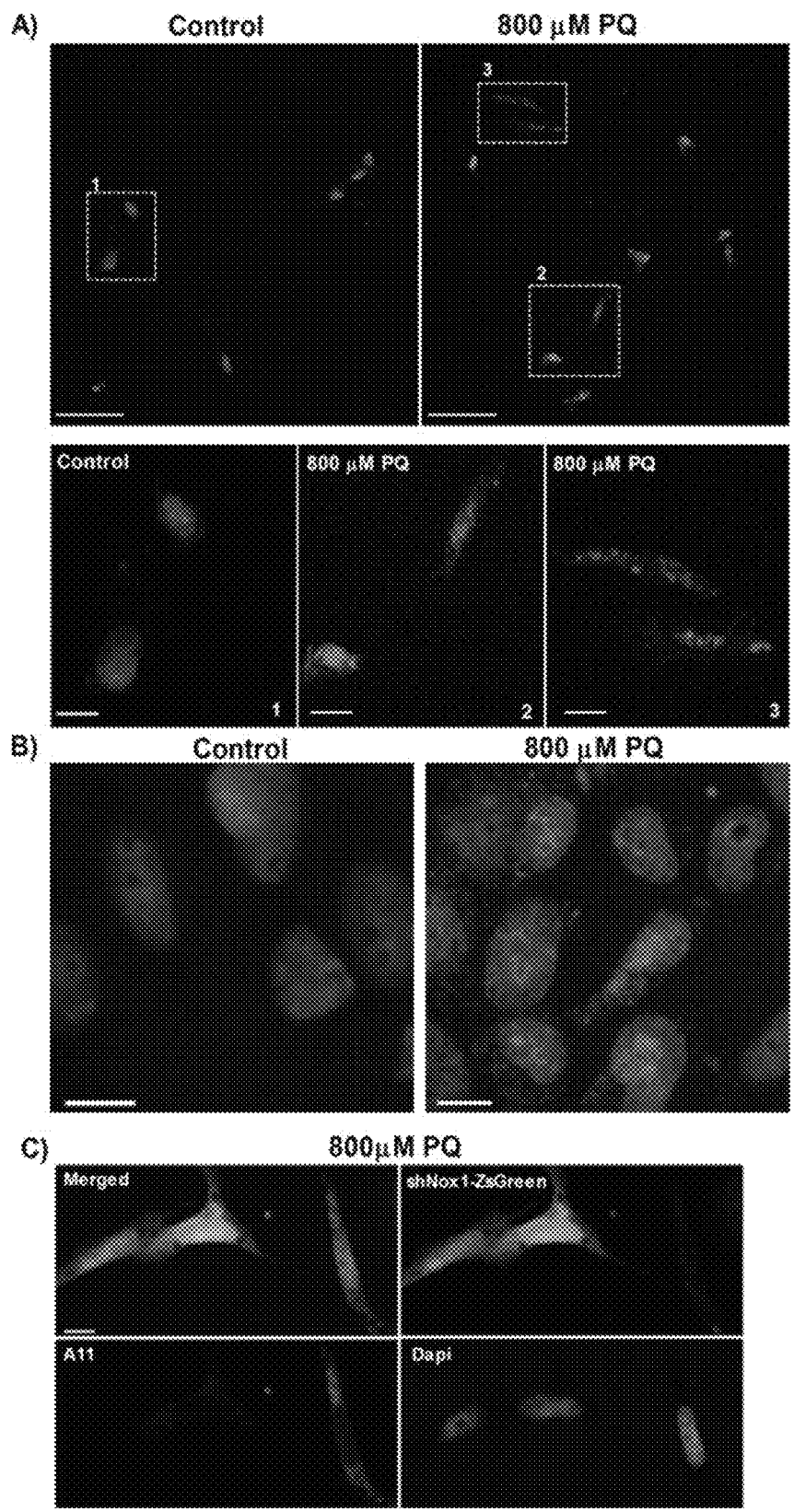
FIG. 9 PQ increases levels of PK-resistant α-synuclein and A11 oligomer formation in N27, which is reversed by Nox1 knockdown. A, PK-resistant α-synuclein immunoreactivity in control and PQ-treated N27 cells. The bottom (scale bars: 10 μm) shows higher magnification of respective boxed areas shown in the top (scale bars: 50 μm). B, C, A11 immunoreactivity of control or PQ-treated N27 cells (B) and in N27 cells incubated with Nox1 sh RNA/LVX (shNox1-ZsGreen) viral particles for 36 h exposed to 800 μM PQ (C). Scale bars: (for B, C), 10 μm.
Figure 15:
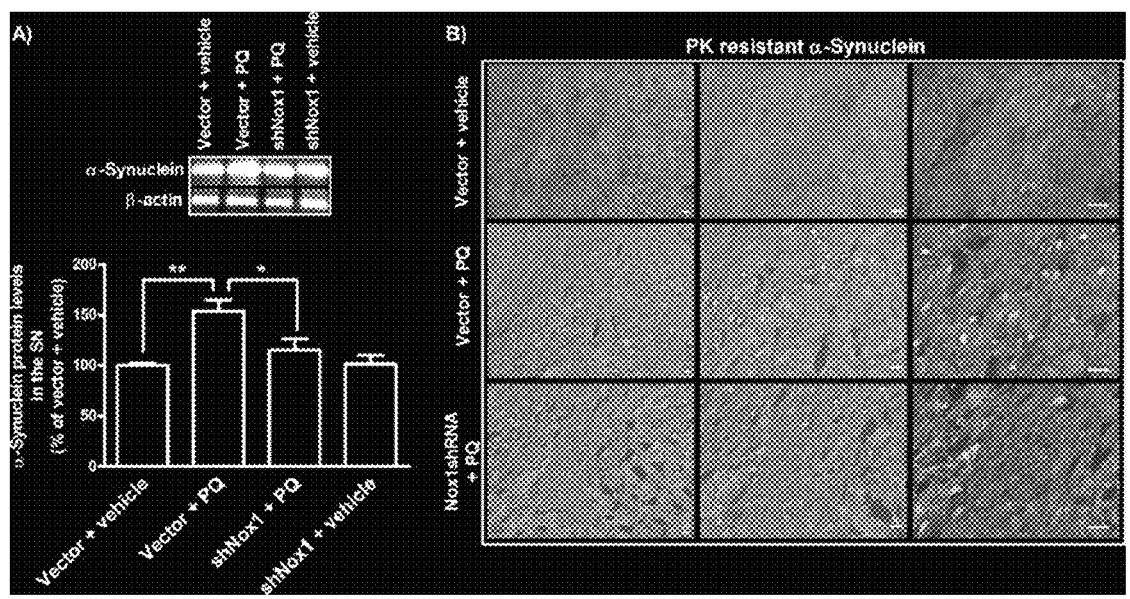
FIG. 15 Nox1 knockdown reduced PQ-mediated α-synuclein increase in the SN dopaminergic neurons. A, Representative immunoblot and quantitative analysis of α-synuclein protein levels. α-Synuclein protein was determined in total lysates of the rats SN tissues in the ipsilateral side by immunoblot analysis. β-Actin was used as an internal control. α-Synuclein protein levels were quantified using Quantity One software and normalized against β-actin. The results are expressed as percentage of vector+vehicle. Data are shown as the mean±SEM. Statistical analysis was performed using one-way ANOVA followed by Bonferroni's multiple-comparison test; *p<0.05 and **p<0.01. B, Representative photomicrographs of PK-resistant α-synuclein immunoreactivity in the ipsilateral SN of brain sections of the four experimental groups. Increased PK-resistant α-synuclein immunostaining observed in the vector+PQ group was significantly decreased by Nox1 knockdown as observed in shNox1+PQ group. Scale bars, 50 µm.
Figure 16:
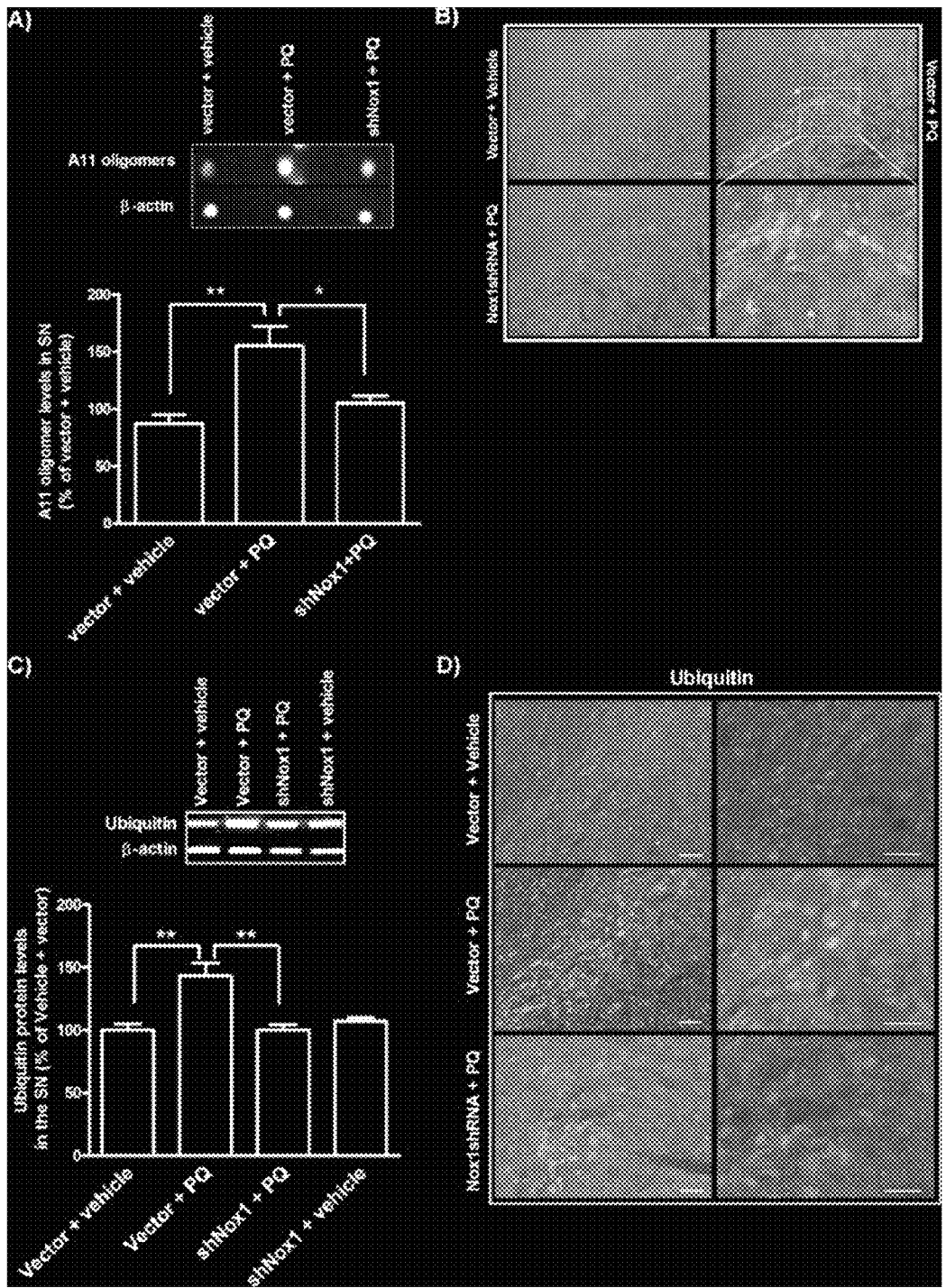
FIG. 16 Nox1 knockdown reduced PQ-mediated A11 oligomers and ubiquitin increase in the SN dopaminergic neurons. Representative immunoblot and quantitative analysis of A11 oligomers (A) and ubiquitin (C) levels determined in total lysates of the rats SN tissues in the ipsilateral side by immunoblot analysis. β-Actin was used as an internal control. All oligomer levels were quantified using Quantity One software and normalized against β-actin. The results are expressed as percentage of vector+vehicle. Data are shown as the mean±SEM. Statistical analysis was performed using one-way ANOVA followed by Bonferroni's multiple-comparison test; *p<0.05, **p<0.01 Representative photomicrographs of A11 oligomers (B) and ubiquitin (D) immunoreactivity in the ipsilateral SN of brain sections of the three experimental groups. B, Bottom right shows higher magnification of the respective boxed area shown in the right top. Scale bars, 50 µm.

In addition to the effect of PQ in α-synuclein expression levels, it was also found that PQ increased the aggregation of α-synuclein (FIGS. 8-10) in N27 cells as well as in the rat SN, accompanied with increased levels of ubiquitin (FIGS. 15, 16C,D). These findings are in agreement with previous reports showing increased α-synuclein aggregation in mice exposed to PQ (Manning-Bog et al., 2002). Based on this, it was sought to enlarge our view of the disease paradigm and search for a potential relationship between Nox1 and α-synuclein aggregation. Nox1 knockdown achieved by viral delivery of shRNA against Nox1 significantly reduced α-synuclein aggregation in both in vitro and in vivo. A large number of reports have similarly shown that AAV-mediated shRNA delivery to the CNS for targeted knockdowns of specific genes can be achieved (Harper et al., 2005), including two of our recent works (Choi et al., 2011, 2012). On the other hand, the lentivirus system that delivers genes to cells showed higher infection efficiency then AAV2, but with less specificity, and was able to infect divided and nondivided cells. In that sense this system is more suitable for in vitro gene delivery using a cell culture system containing only one type of cells. Lentivirus-mediated Nox1 knockdown in N27 cells led to significant reduction in PQ-induced α-synuclein aggregation. Several methods were used for this evaluation and clear evidence was that Nox1 is involved in the aggregation process of α-synuclein induced by PQ (FIGS. 14C,D, 15C, 16B,C). Importantly, Nox1 knockdown also prevented aggregation of WT α-synuclein overexpressed, suggesting that along with its involvement in the transcriptional regulation, Nox1-induced ROS may also play a role in stabilizing the protein, leading to aggregation of α-synuclein.

AAV2-mediated Nox1 knockdown in the rat SN was shown to be effective not only in reducing Nox1 protein levels in the SN (FIG. 13B,C), but also in reducing oxidative stress (FIG. 14C) and dopaminergic neuronal death (FIG. 14A) induced by PQ. Nox1 knockdown induced a significant decrease in the total levels of α-synuclein expression (FIG. 15A) after PQ treatment, as well as a decrease in α-synuclein aggregation, as demonstrated by a decrease in PK-resistant α-synuclein (FIG. 15B). A11 oligomers (FIG. 16A,B) and ubiquitin (FIG. 16C,D) levels were also decreased, indicating that PQ-mediated α-synuclein aggregation is partially regulated by Nox1-derived ROS. These results are in agreement with other studies, which demonstrate that cytoplasmic α-synuclein aggregations can be induced by various ROS generators, such as hydroxyl radicals and peroxynitrite (Butterfield and Kanski, 2001; Matsuzaki et al., 2004). These metabolites are strong oxidants that can promote not only nitration but also oxidation of α-synuclein, favoring the stabilization of the protein polymer by forming stable cross-linked α-synuclein aggregates (Alvarez et al., 1999; Hashimoto et al., 1999; Souza et al., 2000).

In summary, our study provides strong evidence that Nox1 is involved in the mechanism responsible for generation of PQ-mediated oxidative stress conditions implicated in increased α-synuclein expression and aggregation, and dopaminergic neurodegeneration in the PQ-treated rat model of PD. This work also strengthens the possible relationship between oxidative stress and α-synuclein pathology in PD, introducing Nox1 as a key molecule that could serve as a good therapeutic target for PD and others α-synucleinopathies.

References Related to Example 2

1. Alam Z I, Daniel S E, Lees A J, Marsden D C, Jenner P, Halliwell B. A generalised increase in protein carbonyls in the brain in Parkinson's but not incidental Lewy body disease. J Neurochem. 1997; 69:1326-1329.
2. Alvarez B, Ferrer-Sueta G, Freeman B A, Radi R. Kinetics of peroxynitrite reaction with amino acids and human serum albumin. The Journal of biological chemistry. 1999; 274:842-848.
3. Beyer K, Domingo-Sabat M, Ariza A. Molecular pathology of lewy body diseases. Int J Mol Sci. 2009; 10:724-745.
4. Brown T P, Rumsby P C, Capleton A C, Rushton L, Levy L S. Pesticides and Parkinson's disease—is there a link? Environ Health Perspect. 2006; 114:156-164.
5. Butterfield D A, Kanski J. Brain protein oxidation in age-related neurodegenerative disorders that are associated with aggregated proteins. Mech Ageing Dev. 2001; 122:945-962.
6. Chartier-Harlin M C, Kachergus J, Roumier C, Mouroux V, Douay X, Lincoln S, Levecque C, Larvor L, Andrieux J, Hulihan M, Waucquier N, Defebvre L, Amouyel P, Farrer M, Destee A. Alpha-synuclein locus duplication as a cause of familial Parkinson's disease. Lancet. 2004; 364:1167-1169.
7. Choi D H, Cristovao A C, Guhathakurta S, Lee J, Joh T H, Beal M F, Kim Y S. NADPH Oxidase 1-Mediated Oxidative Stress Leads to Dopamine Neuron Death in Parkinson's Disease. Antioxidants & redox signaling. 2012
8. Choi D H, Kim Y J, Kim Y G, Joh T H, Beal M F, Kim Y S. Role of matrix metalloproteinase 3-mediated alpha-synuclein cleavage in dopaminergic cell death. The Journal of biological chemistry. 2011; 286:14168-14177.
9. Clough R L, Dermentzaki G, Haritou M, Petsakou A, Stefanis L. Regulation of alpha-synuclein expression in cultured cortical neurons. J Neurochem. 2011; 117:275-285.
10. Clough R L, Dermentzaki G, Stefanis L. Functional dissection of the alpha-synuclein promoter: transcriptional regulation by ZSCAN21 and ZNF219. J Neurochem. 2009; 110:1479-1490.
11. Clough R L, Stefanis L. A novel pathway for transcriptional regulation of alpha-synuclein. FASEB J. 2007; 21:596-607.
12. Cookson M R. alpha-Synuclein and neuronal cell death. Mol Neurodegener. 2009; 4:9.
13. Cristovao A C, Choi D H, Baltazar G, Beal M F, Kim Y S. The role of NADPH oxidase 1-derived reactive oxygen species in paraquat-mediated dopaminergic cell death. Antioxidants & redox signaling. 2009; 11:2105-2118.
14. Dexter D T, Carter C J, Wells F R, Javoy-Agid F, Agid Y, Lees A, Jenner P, Marsden C D. Basal lipid peroxidation in substantia nigra is increased in Parkinson's disease. J Neurochem. 1989; 52:381-389.
15. Dexter D T, Holley A E, Flitter W D, Slater T F, Wells F R, Daniel S E, Lees A J, Jenner P, Marsden C D. Increased levels of lipid hydroperoxides in the parkinsonian substantia nigra: an HPLC and ESR study. Mov Disord. 1994; 9:92-97.
16. Donato R, Miljan E A, Hines S J, Aouabdi S, Pollock K, Patel S, Edwards F A, Sinden J D. Differential development of neuronal physiological responsiveness in two human neural stem cell lines. BMC neuroscience. 2007; 8:36.
17. Gatto N M, Rhodes S L, Manthripragada A D, Bronstein J, Cockburn M, Farrer M, Ritz B. alpha-Synuclein gene may interact with environmental factors in increasing risk of Parkinson's disease. Neuroepidemiology. 2010; 35:191-195.
18. Hardy J, Lewis P, Revesz T, Lees A, Paisan-Ruiz C. The genetics of Parkinson's syndromes: a critical review. Curr Opin Genet Dev. 2009; 19:254-265.
19. Harper S Q, Staber P D, He X, Eliason S L, Martins I H, Mao Q, Yang L, Kotin R M, Paulson H L, Davidson B L. RNA interference improves motor and neuropathological abnormalities in a Huntington's disease mouse model. Proc Natl Acad Sci USA. 2005; 102:5820-5825.
20. Harraz M M, Marden J J, Zhou W, Zhang Y, Williams A, Sharov V S, Nelson K, Luo M, Paulson H, Schoneich C, Engelhardt J F. SOD1 mutations disrupt redox-sensitive Rac regulation of NADPH oxidase in a familial ALS model. J Clin Invest. 2008; 118:659-670.
21. Hashimoto M, Hsu L J, Xia Y, Takeda A, Sisk A, Sundsmo M, Masliah E. Oxidative stress induces amyloid-like aggregate formation of NACP/alpha-synuclein in vitro. Neuroreport. 1999; 10:717-721.
22. Javoy F, Sotelo C, Herbet A, Agid Y. Specificity of dopaminergic neuronal degeneration induced by intracerebral injection of 6-hydroxydopamine in the nigrostriatal dopamine system. Brain Res. 1976; 102:201-215.
23. Krishnan S, Chi E Y, Wood S J, Kendrick B S, Li C, Garzon-Rodriguez W, Wypych J, Randolph T W, Narhi L O, Biere A L, Citron M, Carpenter J F. Oxidative dimer formation is the critical rate-limiting step for Parkinson's disease alpha-synuclein fibrillogenesis. Biochemistry. 2003; 42:829-837.
24. Kruger R, Kuhn W, Muller T, Woitalla D, Graeber M, Kosel S, Przuntek H, Epplen J T, Schols L, Riess O. Ala30Pro mutation in the gene encoding alpha-synuclein in Parkinson's disease. Nat Genet. 1998; 18:106-108.
25. Manning-Bog A B, McCormack A L, Li J, Uversky V N, Fink A L, Di Monte D A. The herbicide paraquat causes up-regulation and aggregation of alpha-synuclein in mice: paraquat and alpha-synuclein. The Journal of biological chemistry. 2002; 277:1641-1644.
26. Matsuzaki M, Hasegawa T, Takeda A, Kikuchi A, Furukawa K, Kato Y, Itoyama Y. Histochemical features of stress-induced aggregates in alpha-synuclein overexpressing cells. Brain Res. 2004; 1004:83-90.

27. McCormack A L, Atienza J G, Johnston L C, Andersen J K, Vu S, Di Monte D A. Role of oxidative stress in paraquat-induced dopaminergic cell degeneration. J Neurochem. 2005; 93:1030-1037.
28. Miller R L, James-Kracke M, Sun G Y, Sun A Y. Oxidative and inflammatory pathways in Parkinson's disease. Neurochem Res. 2009; 34:55-65.
29. Neumann M, Kahle P J, Giasson B I, Ozmen L, Borroni E, Spooren W, Muller V, Odoy S, Fujiwara H, Hasegawa M, Iwatsubo T, Trojanowski J Q, Kretzschmar H A, Haass C. Misfolded proteinase K-resistant hyperphosphorylated alpha-synuclein in aged transgenic mice with locomotor deterioration and in human alpha-synucleinopathies. J Clin Invest. 2002; 110:1429-1439.
30. Nuber S, Petrasch-Parwez E, Winner B, Winkler J, von Horsten S, Schmidt T, Boy J, Kuhn M, Nguyen H P, Teismann P, Schulz J B, Neumann M, Pichler B J, Reischl G, Holzmann C, Schmitt I, Bornemann A, Kuhn W, Zimmermann F, Servadio A, Riess O. Neurodegeneration and motor dysfunction in a conditional model of Parkinson's disease. J Neurosci. 2008; 28:2471-2484.
31. Polymeropoulos M H, Lavedan C, Leroy E, Ide S E, Dehejia A, Dutra A, Pike B, Root H, Rubenstein J, Boyer R, Stenroos E S, Chandrasekharappa S, Athanassiadou A, Papapetropoulos T, Johnson W G, Lazzarini A M, Duvoisin R C, Di Iorio G, Golbe L I, Nussbaum R L. Mutation in the alpha-synuclein gene identified in families with Parkinson's disease. Science. 1997; 276:2045-2047.
32. Singleton A B, Farrer M, Johnson J, Singleton A, Hague S, Kachergus J, Hulihan M, Peuralinna T, Dutra A, Nussbaum R, Lincoln S, Crawley A, Hanson M, Maraganore D, Adler C, Cookson M R, Muenter M, Baptista M, Miller D, Blancato J, Hardy J, Gwinn-Hardy K. alpha-Synuclein locus triplication causes Parkinson's disease. Science. 2003; 302:841.
33. Sofic E, Lange K W, Jellinger K, Riederer P. Reduced and oxidized glutathione in the substantia nigra of patients with Parkinson's disease. Neurosci Lett. 1992; 142:128-130.
34. Sorce S, Krause K H. NOX enzymes in the central nervous system: from signaling to disease. Antioxidants & redox signaling. 2009; 11:2481-2504.
35. Souza J M, Giasson B I, Chen Q, Lee V M, Ischiropoulos H. Dityrosine cross-linking promotes formation of stable alpha-synuclein polymers. Implication of nitrative and oxidative stress in the pathogenesis of neurodegenerative synucleinopathies. The Journal of biological chemistry. 2000; 275:18344-18349.
36. Terzioglu M, Galter D. Parkinson's disease: genetic versus toxin-induced rodent models. FEBS J. 2008; 275: 1384-1391.
37. Turk P W, Laayoun A, Smith S S, Weitzman S A. DNA adduct 8-hydroxyl-2'-deoxyguanosine (8-hydroxyguanine) affects function of human DNA methyltransferase. Carcinogenesis. 1995; 16:1253-1255.
38. Uversky V N, Li J, Fink A L. Pesticides directly accelerate the rate of alpha-synuclein fibril formation: a possible factor in Parkinson's disease. FEBS Lett. 2001; 500:105-108.
39. Vekrellis K, Xilouri M, Emmanouilidou E, Rideout H J, Stefanis L. Pathological roles of alpha-synuclein in neurological disorders. Lancet Neurol. 2011; 10:1015-1025.
40. Winner B, Jappelli R, Maji S K, Desplats P A, Boyer L, Aigner S, Hetzer C, Loher T, Vilar M, Campioni S, Tzitzilonis C, Soragni A, Jessberger S, Mira H, Consiglio A, Pham E, Masliah E, Gage F H, Riek R. In vivo demonstration that alpha-synuclein oligomers are toxic. Proc Natl Acad Sci USA. 2011; 108:4194-4199.
41. Wood-Kaczmar A, Gandhi S, Yao Z, Abramov A Y, Miljan E A, Keen G, Stanyer L, Hargreaves I, Klupsch K, Deas E, Downward J, Mansfield L, Jat P, Taylor J, Heales S, Duchen M R, Latchman D, Tabrizi S J, Wood N W. PINK1 is necessary for long term survival and mitochondrial function in human dopaminergic neurons. PloS one. 2008; 3:e2455.
42. Zarranz J J, Alegre J, Gomez-Esteban J C, Lezcano E, Ros R, Ampuero I, Vidal L, Hoenicka J, Rodriguez O, Atares B, Llorens V, Gomez Tortosa E, del Ser T, Munoz D G, de Yebenes J G. The new mutation, E46K, of alpha-synuclein causes Parkinson and Lewy body dementia. Ann Neurol. 2004; 55:164-173.
43. Zawia N H, Lahiri D K, Cardozo-Pelaez F. Epigenetics, oxidative stress, and Alzheimer disease. Free Radic Biol Med. 2009; 46:1241-1249.
44. Zhang J, Perry G, Smith M A, Robertson D, Olson S J, Graham D G, Montine T J. Parkinson's disease is associated with oxidative damage to cytoplasmic DNA and RNA in substantia nigra neurons. Am J Pathol. 1999; 154:1423-1429.

Abbreviations Used
AAV2: adeno-associated virus serotype 2
AD: Alzheimer's disease
CNS: central nervous system
GFP: green fluorescence protein
LDH: lactate dehydrogenase
MPTP: 1-methyl-4-phenyl-1,2,3,6-tetrahydropyridine
NBT: nitroblue tetrazolium
NOX: NADPH oxidase
Noxa1: Nox activator 1
Noxo1: Nox organizer 1
6-OHDA: 6-hydroxydopamine
8-oxo-dG: 7,8-dihydro-8-oxo-deoxyguanine
PAK1: p21-activated protein kinase 1
PBD: p21-binding domain
PD: Parkinson's disease
ROS: reactive oxygen species
SN: substantia nigra
SNpc: substantia nigra pars compacta
TH: tyrosine hydroxylase General Provisions Although more than one route can be used to administer a particular compound, a particular route can provide a more immediate and more effective reaction than another route. Accordingly, the described routes of administration are merely exemplary and are in no way limiting.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A method for treating Parkinson's Disease in a subject, comprising administering to the subject a therapeutically effective amount of a composition that inhibits the expression or action of NADPH oxidase 1 (Nox1) in the subject; wherein the composition comprises an adeno-associated virus (AAV)-mediated RNA interfering molecule targeting Nox1.

2. The method of claim 1, wherein the composition is administered to the substantia nigra (SN) of the subject.

3. The method of claim 1, wherein said composition comprises a compound that inhibits Nox1 expression in the subject whereby dopaminergic neuronal degeneration is reduced.

4. The method of claim 3, wherein the compound is administered to the substantia nigra (SN) of the subject.

5. A method of treating or delaying the onset of a neurodegenerative disease associated with the reactive oxygen species generation associated with Nox1 in a subject, the method comprising administering to the subject a therapeutically effective amount of NADPH oxidase inhibiting (NOI) compound;
wherein the NOI compound comprises an adeno-associated virus (AAV)-mediated RNA interfering molecule targeting Nox1.

6. The method of claim 5, wherein said neurodegenerative disease is Alexander disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington's disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson's disease, Pelizaeus-Merzbacher Disease, Pick's disease, Primary lateral sclerosis, Prion diseases, Refsum's disease, Sandhoff disease, Schilder's disease, Sub-Acute Combined Degeneration of the Cord Secondary to Pernicious Anaemia, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis or Charcot-Marie-Tooth disease.

7. The method of claim 5, wherein said subject exhibits one or more of the following symptoms:
resting tremor, bradykinesia, muscle rigidity, postural instability, freezing of gait, micrographia, "mask-face", or uncontrolled accelerative movements.

8. The method of claim 5, wherein said subject exhibits one or more of the following symptoms:
include memory impairment, disorientation, misinterpreting spatial relationships, impaired speech, personality changes; or impairment of familiar tasks.

9. The method of claim 5, wherein said subject exhibits one or more of the following symptoms:
twitching and cramping of the muscles, muscle weakness in the arms or legs, loss of motor control in the arms or legs, general weakness and fatigue, tripping and falling, dropping things, impaired speech, or difficulty chewing or swallowing.

10. The method of claim 5, wherein said neurodegenerative disease is Parkinson's disease, Alzheimer's disease, Huntington's disease, or Amyotrophic lateral sclerosis.

11. The method of claim 5, wherein the NOI compound is provided in a pharmaceutical composition with a pharmaceutically acceptable carrier.

* * * * *